(12) United States Patent
Djupesland

(10) Patent No.: US 11,291,626 B2
(45) Date of Patent: Apr. 5, 2022

(54) NASAL DELIVERY OF OXYTOCIN

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 0 days.

(21) Appl. No.: 13/823,071

(22) PCT Filed: Sep. 14, 2011

(86) PCT No.: PCT/IB2011/002347
§ 371 (c)(1),
(2), (4) Date: Sep. 17, 2013

(87) PCT Pub. No.: WO2012/035427
PCT Pub. Date: Mar. 22, 2012

(65) Prior Publication Data
US 2014/0018295 A1    Jan. 16, 2014

(51) Int. Cl.
| | | |
|---|---|---|
| A61K 9/00 | (2006.01) | |
| A61K 38/095 | (2019.01) | |
| A61M 15/08 | (2006.01) | |
| A61M 15/00 | (2006.01) | |
| A61K 31/4174 | (2006.01) | |
| A61K 31/551 | (2006.01) | |

(52) U.S. Cl.
CPC ........ *A61K 9/0043* (2013.01); *A61K 31/4174* (2013.01); *A61K 31/551* (2013.01); *A61K 38/095* (2019.01); *A61M 15/0091* (2013.01); *A61M 15/0098* (2014.02); *A61M 15/08* (2013.01); *A61M 2202/0468* (2013.01); *A61M 2202/064* (2013.01); *A61M 2205/59* (2013.01)

(58) Field of Classification Search
CPC .. A61K 31/4174; A61K 31/551; A61K 38/11; A61K 9/0043; A61M 15/0091; A61M 15/0098; A61M 15/08; A61M 2202/0468; A61M 2202/064; A61M 2205/59
USPC ....................................................... 514/11.6
See application file for complete search history.

(56) References Cited

U.S. PATENT DOCUMENTS

| | | | |
|---|---|---|---|
| 605,436 | A | 6/1898 | Kellogg |
| 642,748 | A | 2/1900 | Manners |
| 658,436 | A | 9/1900 | Groth |
| 746,749 | A | 12/1903 | Seidel |
| 902,832 | A | 11/1908 | Philbrook |
| 5,797,392 | A | 8/1998 | Keldmann et al. |
| 6,648,848 | B1 | 11/2003 | Keldmann et al. |
| 6,715,485 | B1 | 4/2004 | Djupesland |
| D530,815 | S | 10/2006 | Murphy et al. |
| 7,347,201 | B2 | 3/2008 | Djupesland |
| 7,377,901 | B2 | 5/2008 | Djupesland et al. |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland et al. |
| 7,975,690 | B2 | 6/2011 | Djupesland |
| 8,047,202 | B2 | 11/2011 | Djupesland |
| 8,146,589 | B2 | 4/2012 | Djupesland |
| 8,171,929 | B2 | 5/2012 | Djupesland et al. |
| 8,198,240 | B2 | 6/2012 | Yeomans et al. |
| 8,327,844 | B2 | 12/2012 | Djupesland |
| 8,511,303 | B2 | 8/2013 | Djupesland |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,590,530 | B2 | 11/2013 | Djupesland et al. |
| 8,596,278 | B2 | 12/2013 | Djupesland |
| 8,800,555 | B2 | 8/2014 | Djupesland |
| 8,875,704 | B2 | 11/2014 | Djupesland et al. |
| 8,899,229 | B2 | 12/2014 | Djupesland et al. |
| 8,910,629 | B2 | 12/2014 | Djupesland et al. |
| D723,156 | S | 2/2015 | Djupesland et al. |
| D725,769 | S | 3/2015 | Djupesland et al. |
| 8,978,647 | B2 | 3/2015 | Djupesland et al. |
| 9,010,325 | B2 | 4/2015 | Djupesland et al. |
| 9,038,630 | B2 | 5/2015 | Djupesland et al. |
| 9,067,034 | B2 | 6/2015 | Djupesland et al. |
| 9,072,857 | B2 | 7/2015 | Djupesland |

(Continued)

FOREIGN PATENT DOCUMENTS

| | | |
|---|---|---|
| GB | 2400565 A | 10/2004 |
| GB | 2437488 A | 10/2007 |

(Continued)

OTHER PUBLICATIONS

Clinical Trial NTC01028677, Dec. 8, 2019.*
http://www.nhlbi.nih.gov/health/health-topics/topics/stroke/treatment.html (Feb. 2011).*
Sporn et al., "Chemoprevention of Cancer," Carcinogenesis, vol. 21 (2000).*
Kovacs et al. Psychoneurodendocrinology, vol. 23, No. 8, pp. 945-962, 1998).*
Epperson et al. (Epperson et al. Biol Psychiatry 1996; 547-549).*
Oxytocin IU (Oxytocin leaflet, updated Sep. 2012).*
Chad Pediatric Otolaryngology (Patient Information Sheet, Nasal Hygiene Dec. 24, 2010).*
Therapeutic Intranasal Drug Delivery (Needless treatment options for medical problems, available Oct. 11, 2008.*

(Continued)

*Primary Examiner* — James H Alstrum-Acevedo
*Assistant Examiner* — Tara L Martinez
(74) *Attorney, Agent, or Firm* — Finnegan, Henderson, Farabow, Garrett & Dunner, LLP

(57) ABSTRACT

A nasal delivery device for and method of delivering a substance, preferably comprising oxytocin, non-peptide agonists thereof and antagonists thereof, preferably as one of a liquid, as a suspension or solution, or a powder, to the nasal airway of a subject, preferably the posterior region of the nasal airway, and preferably the upper posterior region of the nasal airway which includes the olfactory bulb and the trigeminal nerve, and preferably in the treatment of neurological conditions and disorders.

19 Claims, 43 Drawing Sheets

(56) References Cited

U.S. PATENT DOCUMENTS

Figure 1:
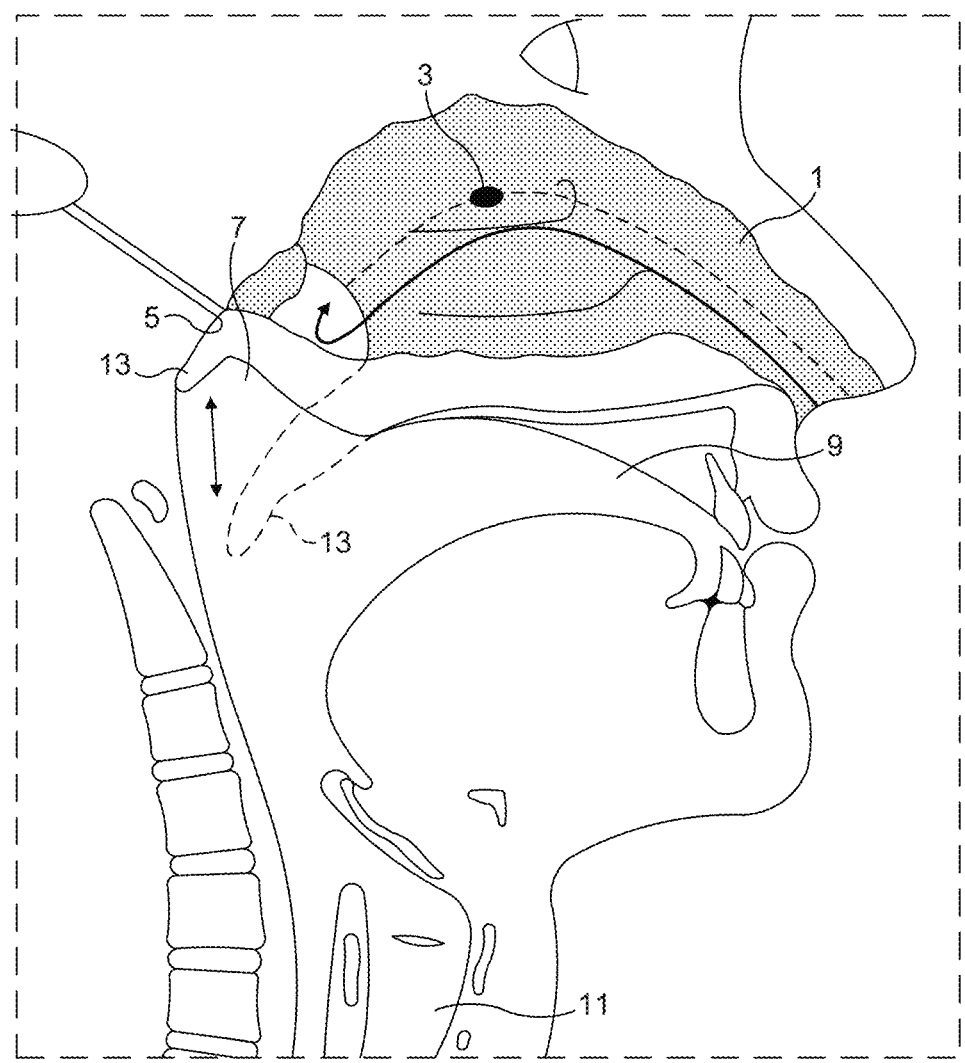

| | | |
|---|---|---|
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| 2002/0068080 A1* | 6/2002 | Lerner .............. A61K 9/0009 424/434 |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2004/0235956 A1 | 11/2004 | Quay |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0054843 A1* | 3/2007 | Yeomans et al. ............ 514/9 |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0181880 A1 | 7/2009 | Yeomans et al. |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0242959 A1 | 9/2010 | Djupesland et al. |
| 2010/0282246 A1 | 11/2010 | Djupesland et al. |
| 2010/0288275 A1* | 11/2010 | Djupesland et al. .... 128/203.15 |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |

FOREIGN PATENT DOCUMENTS

| | | |
|---|---|---|
| GB | 2438834 A | 12/2007 |
| WO | WO 96/22802 | 8/1996 |
| WO | WO 98/53869 | 12/1998 |
| WO | WO 00/51672 | 9/2000 |
| WO | WO 2000/051672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 2003/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO2008042452 | * 4/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |

(56) References Cited

FOREIGN PATENT DOCUMENTS

| | | |
|---|---|---|
| WO | WO 2013/124493 | 8/2013 |
| WO | WO 2014/155192 | 10/2014 |

OTHER PUBLICATIONS

American Family Physician (Dec. 15, 2000; 62(12): 2695-2696).*
Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be An Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using A Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liguid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The Target Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).
Fine et al., "Autism spectrum disorders and symptoms in children with molecularly confirmed 22q11.2 deletion syndrome," J Autism Dev Disord, 35(4):461-470, (2005).
Caradang et al., "Metyrosine in psychosis associated with 22q11.2 deletion syndrome: case report," J Child Adolesc Psychopharmacol, 17(1):115-120, (2007).
Guastella et al., "Intranasal oxytocin improves emotion recognition for youth with autism spectrum disorders," Biol Psychiatry, 67(7):692-694, (2010).
Ross et al., "Oxytocin and the neural mechanisms regulating social cognition and affiliative behavior," Front Neuroendocrinol, 30(4):534-547, (2009).

* cited by examiner

NASAL DELIVERY OF OXYTOCIN

The present invention relates to a nasal delivery device for and a method of delivering a substance comprising oxytocin, non-peptide agonists thereof and antagonists thereof, in particular as one of a liquid, as a suspension or solution, or a powder, to the nasal airway of a subject, in particular the posterior region of the nasal airway, and in particular the upper posterior region of the nasal airway, which includes the olfactory bulb and the trigeminal nerve, in particular in the treatment of neurological conditions and disorders.

Referring to FIG. 1, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

Figure 2:
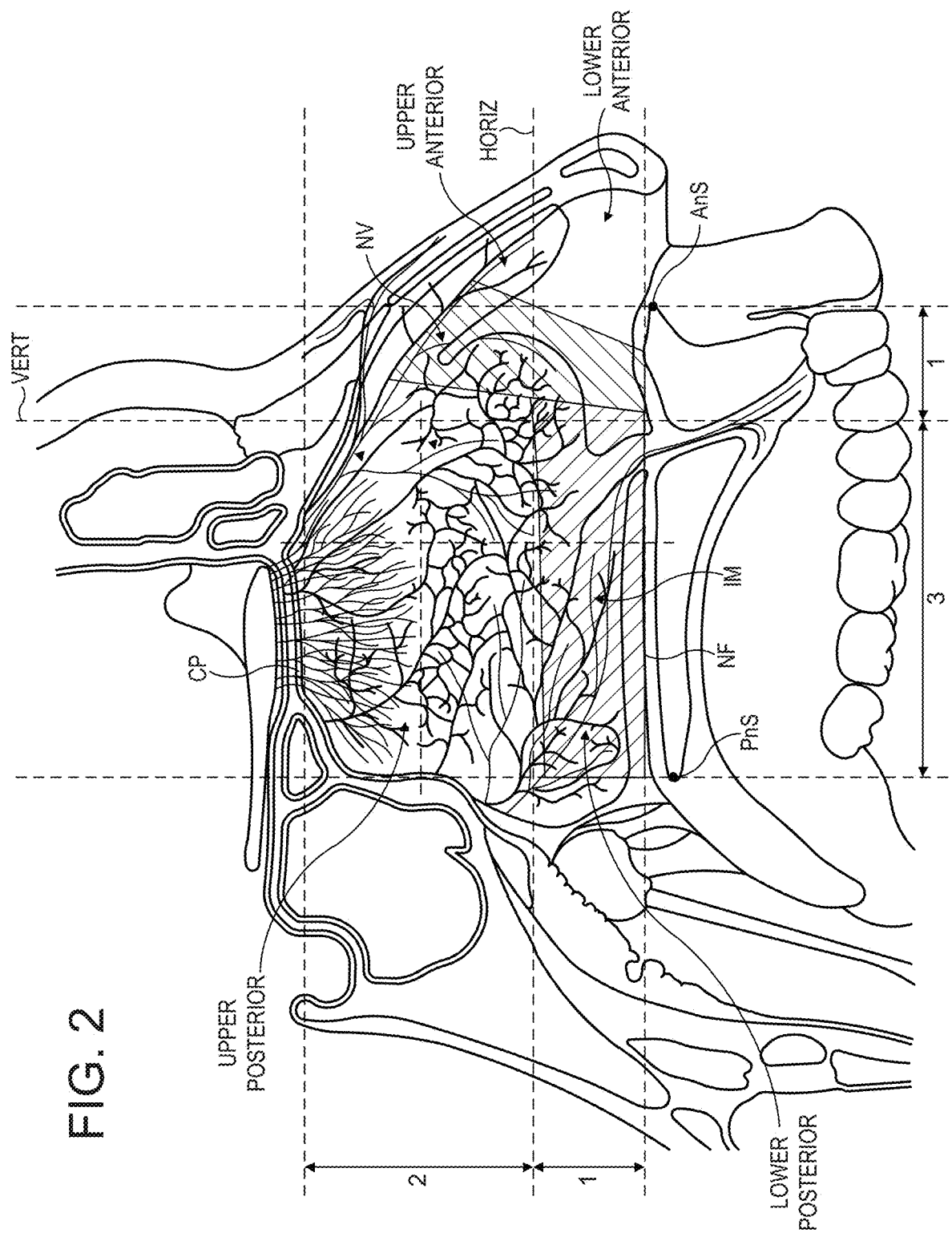

The posterior region of the nasal airway is that region which is posterior of the nasal valve NV, as illustrated in FIG. 2. The nasal valve comprises the anterior bony cavum which contains inferior turbinate erectile tissue and septal erectile tissue, which are supported respectively by compliant ala tissue and the rigid cartilaginous septum (Cole). These elements combine to form a dynamic valve, which extends over several millimetres, that adjusts nasal airflow, and is stabilized by cartilage and bone, modulated by voluntary muscle and regulated by erectile tissue. The lumen of the nasal valve is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve is lined in its anterior part with transitional epithelium, with a gradual transition posterior to respiratory epithelium. The nasal valve and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium. The olfactory epithelium extends on both the lateral and medial sides of the nasal airway, and typically extends downwards about 1.5 to 2.5 cm.

The upper posterior region is the region above the inferior meatus IM, as illustrated in FIG. 2, and encompasses the middle turbinate, the middle meatus, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 2, the posterior region of the nasal airway is the nasal region posterior of an imaginary vertical plane VERT which is located at a position corresponding to the lower angle of the anterior nasal aperture (aperture piriformis), which corresponds substantially to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger defines the distance between the anterior nasal spine AnS and the posterior nasal spine PnS as being 56 mm in eighteen year old boys and 53.3 mm in eighteen year old girls).

As further illustrated in FIG. 2, the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek et al define the distance from the nasal floor NF to the cribiform plate CP as 46+/−4 mm).

The upper posterior region is thus that upper posterior region which is bounded by the above-defined vertical and horizontal planes VERT, HORIZ.

The present invention is directed to the delivery of a substance to the nasal airway of a subject, particularly in the treatment of neurological conditions and disorders, using the delivery technique of WO-A-2000/051672 and WO-A-2003/000310, the contents of which are each herein incorporated by reference.

WO-A-2000/51672 and WO-A-2003/000310 disclose delivery devices for delivering a substance, in particular a medicament, in a bi-directional flow through the nasal cavities, that is, an air flow which passes into one nostril, around the posterior margin of the nasal septum and in the opposite direction out of the other nostril.

The nasal delivery technique of the present invention provides for delivery to the olfactory region, the trigeminal nerve and other structures of the limbic system which interface at the nasal airway, which features are located in the superior region of the nasal cavities and represents the only region where it is possible to circumvent the blood-to-brain barrier (BBB) and enable communication with the cerebrospinal fluid (CSF) and the brain.

In one embodiment the substance is delivered as a powder, preferably containing from about 1 IU to 100 IU, more preferably from about 5 IU to about 80 IU, still more preferably from about 5 IU to about 50 IU, yet more preferably from about 5 IU to about 20 IU, still more preferably from about 20 IU to about 100 IU, yet more preferably from about 40 IU to about 100 IU, and preferably less than about 15 IU or greater than about 50 IU.

In one embodiment the active ingredient is mixed with a bulking agent, such as lactose.

In one embodiment the substance includes a thickening agent, which thickens following delivery and on exposure to a moist environment, such as in the nasal airway, thereby providing for increased residency at the target region.

In one embodiment the thickening agent comprises pectin, agar-agar, lignin, algin, gums, such as vegetable gums, and cellulose.

In one embodiment the substance can be delivered as a powder, followed by application of a liquid, typically as a liquid spray, to promote dissolution and transfer of the active ingredient.

In another embodiment the substance is delivered as a liquid, preferably containing from about 1 IU to about 10 IU, more preferably from 3 IU to 10 IU, still more preferably from about 3 IU to about 5 IU or greater than 5 IU.

In one embodiment the substance is delivered in a once-daily administration.

In another embodiment the substance is delivered in a twice-daily administration.

In one embodiment the active ingredient comprises oxytocin.

In another embodiment the active ingredient comprises a non-peptide oxytocin agonist, such as WAY-267,464.

In one embodiment the active ingredient can comprise both peptide and non-peptide oxytocin.

In a further embodiment the active ingredient comprises an oxytocin antagonist.

In other embodiments the active ingredient can instead be an analogue or derivative or oxytocin, such as carbetocin or demoxytocin.

In one embodiment the administration can be targeted to provide for both N2B and systemic delivery.

In one embodiment the substance can be formulated selectively to provide for greater N2B or systemic delivery.

In another embodiment the substance can comprise two substance components, one formulated for N2B delivery and the other formulated for systemic delivery.

In one embodiment the substance comprises a decongestant, such as oxymetazoline.

The nasal delivery technique of the present invention provides for the treatment of neurological diseases and conditions, including: neurodegenerative diseases and conditions, including Alzheimer's disease, Huntington's disease, Parkinson's disease, dementia and stroke, bi-polar disorder, diabetes, neuropsychiatric disorders, including OCD, autism, eating disorders, addiction, schizophrenia, psychosis, PTSD, depression, chronic depression, disorders associated with abuse and mood disorders, promoting well-being, promoting overall calm, anxiety, including modulating anxiety, increasing trust, reducing fear, hair loss, cancer, obesity, atherosclerotic cardiovascular disease, essential hypertension, polycystic ovary syndrome, syndrome X, ischemia, especially cerebral ischemia, traumatic brain injury, immunodeficiency, sexual dysfunction, promoting an orgasm, regulation of maternal behaviour, including mother-infant bonding, regulation of sexual behaviour, including regulation of female sexual behaviour and regulation of male sexual behaviour, promoting social behaviour, including regulation of social behaviour, including regulation of male and female aggression, promoting social memory, including social recognition, love bonding and pair bonding, promoting social recognition, promoting intelligence, including non-verbal intelligence, promoting learning, promoting memory, promoting cognition, lowering sympathoadrenal tone ("flight and fight response"), enhancing digestive activity, enhancing anabolic activity, decreasing blood pressure, inhibiting salt-appetite, and improving wound healing.

In other embodiments the nasal delivery technique of the present invention provides for suppression of fever, and by way of pain relief, such as in the treatment of breakthrough pain, for example, in cancer patients.

Differently from oral delivery techniques which utilize gastro-intestinal (GI) absorbtion and exhibit a high first-pass metabolism, the delivery technique of the present Invention avoids this effect, thus delivering more substance to the blood.

The delivery technique of the present invention, which provides for nose-to-brain (N2B) delivery, enables the delivery of substances to the brain in an amount significantly higher than other conventional delivery routes, such as that achieved by the oral route.

Finally, it will be understood that the present invention has been described in its preferred embodiments and can be modified in many different ways.

REFERENCES

1. Cole, P, The Respiratory Role of the Upper Airways, a selective clinical and pathophysiological review. 1993, Mosby-Year Book Inc. ISBN.1.55664-390-X.
2. Rosenberger, H, Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, S.C., USA, 1934.
3. Zacharek, M A et al, Sagittal and Coronal Dimensions of the Ethmoid Roof: A Radioanatomic Study, Am J Rhinol 2005, Vol 19, pages 348 to 352.

Nasal Delivery Device

The present invention relates to a delivery device for and a method of delivering a substance, in particular one of a liquid, as a suspension or solution, or a powder containing a medicament, especially a topical pharmaceutical, a cleansing agent, or an irrigating agent, as a liquid, preferably combined with a cleansing agent, to the nasal airway of a subject. In particular, the present invention relates to the delivery of medicament to and the irrigation of the nasal mucosa, the anterior region of nasopharynx, the paranasal sinus ostia, the tubal ostia of the auditory tubes, the sinus tubes, the auditory tubes, the tympanic cavities and the paranasal sinuses.

Figure 3:
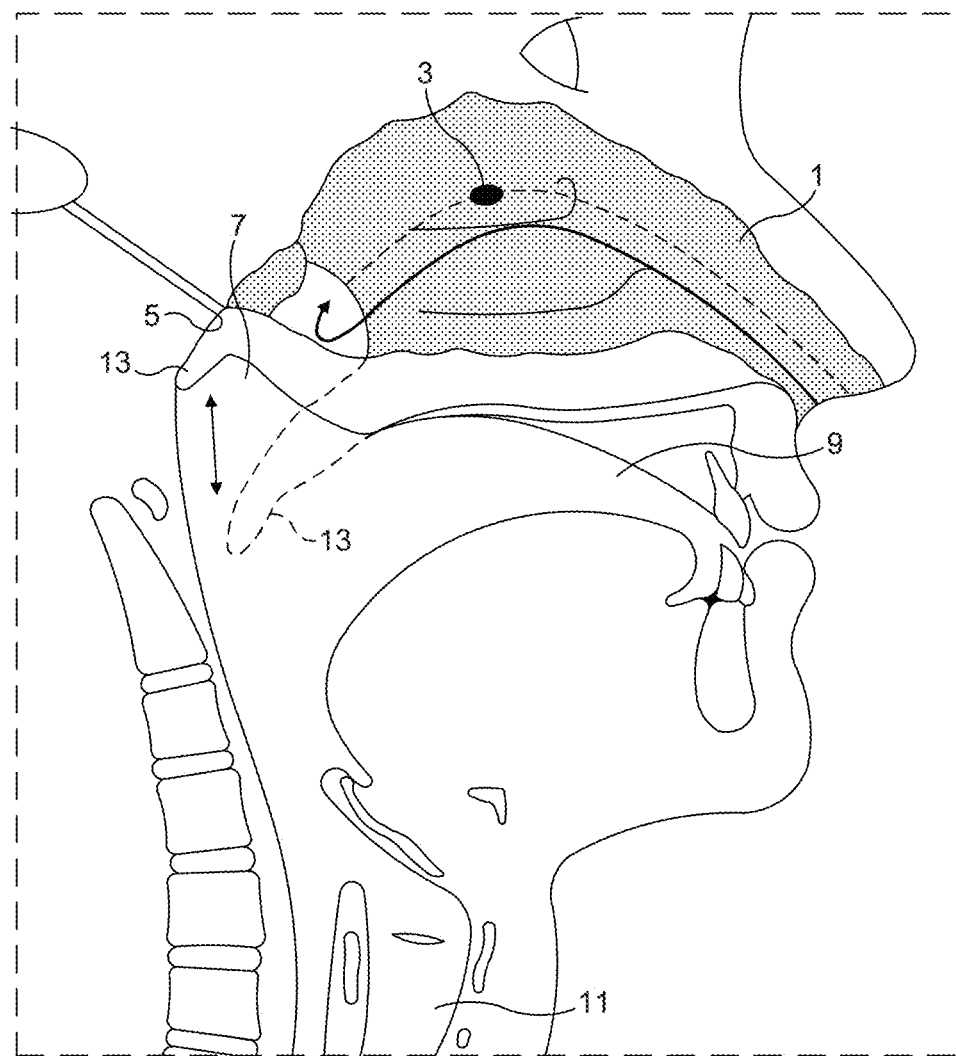

Referring to FIG. 3, the nasal airway 1 comprises the two nasal cavities separated by the nasal septum, which airway 1 includes numerous ostia, such as the paranasal sinus ostia 3 and the tubal ostia 5, olfactory cells and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Worryingly, the incidence of such allergic and non-allergic inflammatory diseases is increasing. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Indeed, topical administration is advantageous in minimising the possible side effects of systemic administration. Medicaments that are commonly topically delivered include decongestants, anti-histamines, cromoglycates, steroids and antibiotics.

There are now an increasing number of adults and children who rely on pharmaceuticals to relieve symptoms associated with nasal conditions. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

Furthermore, medicaments are now increasingly systemically delivered through the nasal pathway, the nasal pathway offering a good administration route for the systemic delivery of pharmaceuticals, such as hormones, for example oxytocin, and anti-migraine compositions, as the high blood flow and large surface area of the nasal mucosa advantageously provides for rapid systemic uptake.

A variety of delivery systems have been developed to deliver substances to the nasal airways of subjects.

Conventionally, spray bottles have been used to deliver a medicament-containing liquid or an irrigating liquid to the nasal airways of subjects. However, the distribution of the delivered substance, in particular to the posterior region of the nasal airway, is less than ideal, especially in the cases of moderate and severe nasal obstruction. This poor distribution is often further exacerbated by a subject inhaling through the nasal airway during delivery, as is often prescribed, in an attempt to deliver the substance to the posterior region of the nasal airway. Indeed, an amount of the substance can be drawn into the lungs or swallowed in each delivery, which could be problematic in paediatric subjects if the medicament is a potent pharmaceutical, such as a steroid, which has to be administered frequently. In addition, the spray is frequently directed against the nasal septum which can undesirably lead to localised deposition. Further, the mechanical action of the delivery mechanism of the spray bottles can cause irritation and bleeding.

GB-A-408856 discloses a delivery device, which in one mode of use, apparently allows for the delivery of two separate air flows entraining medicament into respective ones of the nasal cavities of a subject. This delivery device comprises a chamber containing a sponge saturated with medicament, a mouthpiece connected to the chamber and first and second nosepieces connected to the chamber. In one mode of use, the mouthpiece is taken in the mouth of a subject and the nosepieces fitted into respective ones of the nostrils of the subject, and on exhalation through the mouthpiece separate air flows entraining medicament are apparently driven into the nasal cavities of the subject.

It is not seen, however, how this delivery device could function properly in this mode of use, since, as is now understood, the velum of the subject would close on exhalation through his or her mouth and hence close the nasal airway, thereby preventing any significant air flow into the nasal cavities.

WO-A-98/53869 discloses a delivery device for delivering a powder containing a medicament to the nasal mucosa in one of the nasal cavities of a subject. This device comprises a tubular section which contains a metered dose of powdered medicament. In use, the ends of the tubular section are respectively located in the nostril of one of the nasal cavities and the mouth of a subject, and on exhalation by the subject through his or her mouth the exhaled air entrains the powdered medicament and delivers the same into the one nasal cavity, with the exhaled air backflowing out of the one nostril around the tubular section. In one embodiment the tubular section includes a flexible portion upstream of the dose of powdered medicament. The provision of this flexible portion allows the subject to close the tubular section at a point upstream of the medicament, such that, on release of the closed flexible portion during exhalation, a short explosive air flow entraining medicament is delivered into the one nasal cavity. In another embodiment the end of the tubular section located in the nostril can be shaped to act to locate the tubular section in a position in the nostril which allows for the deposition of the powdered medicament on the nasal mucosa.

Whilst this delivery device is simple in construction, the operation of the device still does not provide for the effective delivery of substances, in particular one of a liquid or powder containing medicament, to the posterior region of the nasal airway, since medicament is delivered separately to each of the nasal cavities and the air flow into and out of each nasal cavity is through the same opening, namely the respective nostril, with the closed posterior region of the respective nasal cavity acting as a pressure reflecting surface which causes the exhaled air to backflow out of the one nostril before ever adequately reaching the posterior region of the respective nasal cavity. Further, in providing a short explosive burst of air flow into one of the nasal cavities, it is not possible to achieve a sustained and controlled bi-directional air flow through the nasal cavities which has been found necessary to deliver a substance effectively to the posterior region of the nasal airway.

For any substance to be delivered effectively to the nasal airway, it is highly desirable that the administration is efficient and simple. However, there can be problems in attempting to achieve this goal. In particular, the pathological changes observed with nasal inflammation make administration of substances, such as liquids or powders, tricky, particularly to the posterior region of the nasal airway and the posterior margins of the nasal structures. Indeed, as a consequence of the complex geometry of the narrow slit-like passages in the nasal airway, these passages become partially occluded when the nasal mucosa is inflamed and congested, making the distribution of topical pharmaceuticals to the nasal airway difficult.

It is thus an aim of the present invention to provide a delivery device for and a method of achieving a more optimally distributed deposition of a substance, especially topical pharmaceuticals, in the nasal airway, particularly the posterior region of the nasal airway, and in particular the anterior region of the nasopharynx where the adenoid and tubal ostia are located.

Accordingly, the present invention provides a delivery device for delivering a substance to the nasal airway of a subject, comprising: a closure unit for causing the closure of the oropharyngeal velum of the subject; and a delivery unit for delivering a gas flow entraining a substance to one of the nostrils of the subject at such a driving pressure as to flow around the posterior margin of the nasal septum and out of the other nostril of the subject, wherein the delivery unit comprises a nosepiece which includes an outlet through which the gas flow is in use delivered to the one nostril and a sealing member for sealing the one nostril to the outlet such as in use to prevent the escape of the gas flow through the one nostril.

In one embodiment the substance comprises a dry powder.

In another embodiment the substance comprises liquid droplets.

Preferably, the particle size distribution of the substance is principally in the range of about 1 to 10 μm.

In one embodiment the substance contains a medicament, particularly for the treatment of a nasal condition. In a preferred embodiment the particle size distribution of the substance can include a smaller fraction of larger particles, typically in the range of about 10 to 30 μm, and preferably in the range of about 20 to 30 μm.

In other embodiments the substance can be a cleansing agent, as a powder or liquid, for cleansing the nasal airway, or a liquid, which may preferably contain a cleansing agent, for irrigating the nasal airway. By way of example, the delivery device could be used to administer saline or other solutions to the nasal airway to remove particles and secretions, in particular from the posterior region of the nasal airway, which resulting solution could be analysed for diagnostic or research purposes. In a preferred embodiment the particle size distribution of the cleansing or irrigating agents can include a fraction of larger particles, particularly in relation to the mechanical action of the particles.

The present invention also provides a method of delivering a substance to the nasal airway of a subject, comprising the steps of: sealing one of the nostrils of a subject to an outlet of a delivery unit such as to prevent the escape of a gas flow through the one nostril; closing the oropharyngeal velum of the subject; and delivering a gas flow entraining a substance through the outlet at such a pressure as to flow around the posterior margin of the nasal septum and out of the other nostril of the subject.

In one embodiment the closure of the velum is achieved directly by the use of an instrument for pressing against the velum to close the same or a bung for temporarily closing the opening behind the velum between the nasal airway and the oral cavity.

In a preferred embodiment the closure of the velum is achieved indirectly by the creation of a positive pressure in the oral cavity, or more correctly a positive pressure differential between the oral cavity and the nasal airway, such as achieved on exhalation.

Preferably, the velum is closed simultaneously with the onset of the delivery of the substance to the nasal airway.

In a preferred embodiment closure of the velum is achieved automatically by the subject exhaling against a flow resistor, which flow resistor may be operably connected to a tubular section held between the lips of the subject. The flow resistor can be configured to provide the required intra-oral positive pressure.

It has been established that flow rates of about 1 to 20 litres per minute, and particularly about 3 to 15 litres per minute, can be easily achieved by a subject and that and a fairly constant air flow can be maintained for up to 20 seconds depending on the flow rate. For some treatment regimes, it is important that a stable flow of relatively high flow rate be maintained for a period of a few seconds, preferably 3 to 10 seconds, in order to enable the substance to penetrate to the more remote parts of the nasal airway.

In one embodiment the air flow of exhalation by a subject is used to power a mechanism which disperses the substance into a volume of air and delivers that dispersed substance into the nasal airway.

Preferably, the mechanism is so arranged that the substance is delivered into the nasal airway after the velum has been closed or simultaneously with velum closure. In this respect, it will be understood that bi-directional flow through the nasal cavities is possible only when the velum is closed and that any substance delivered prior to closure of the velum would undesirably be delivered to the lower airway or the gut.

Preferably, the release of the substance into the nasal airway is triggered by the air flow created on exhalation.

In a preferred embodiment a pressure-sensitive valve is utilised to trigger release of the substance when a predetermined flow rate has been developed. It should be understood that control of the flow rate of the gas in which the substance is delivered is important, as this flow rate, along with the particle size distribution of the substance, are the significant factors determining the particle deposition efficiency.

In a preferred embodiment the pressure-sensitive valve is not opened until the subject has maintained a predetermined flow rate, and can be closed when the flow rate drops below the predetermined flow rate so as to stop the delivery of the substance.

In a preferred embodiment, where medicament is delivered in a driving gas, one or both of the timing and duration of the opening of the pressure-sensitive valve and the dose released are carefully controlled to ensure a standardised dosage.

In one embodiment, where the substance is released into a chamber and a gas flow, in one embodiment the exhalation flow, is provided to induce the mixing of a metered dose of the substance, the delivery of the gas flow can be prolonged to flush the nasal airway as this prolonged flushing does not effect the delivered dose. A mechanical device powered by a hand-chargeable spring, pressurised air or similar, may be used to provide the driving gas.

Regardless of the system employed, the flow characteristics can be optimised to improve the deposition of the substance and the comfort factor, such as to avoid an abrupt onset which is likely to induce withdrawal reflexes.

Preferably, a metered dose of the substance is dispensed into a delivery chamber by a dosing mechanism. This dosing mechanism can be constructed in such a way as to allow for a gradual release of the substance. This gradual release will better enable the substance to be entrained by the gas flow and thereby improve delivery to all ventilated parts of the nasal airway, in particular in the contralateral nasal cavity.

In a preferred embodiment the exhalation air flow developed by the subject, which closes the velum, provides the gas flow for entraining the substance and providing the bi-directional flow. This configuration is advantageous in that a separate driving gas flow need not be developed.

Preferably, the nosepiece is configured to extend about 1 cm into the one nasal cavity so as to expand the valve region, a region located about 2 to 3 cm within a nasal cavity which is usually the flow limiting region, and reduce the resistance which may be high in the case of nasal inflammation.

The shape of the nosepiece can be tailored to suit specific needs. For example, the internal shape of the nosepiece may be optimised to promote turbulence and achieve a more optimal dispersion of the substance.

The nosepiece may include a tight fitting nasal olive, which can aid the creation of a suitable physiological gas flow. The olive may be detachable such as to allow for other olives of the same or different dimensions to be fitted. In the case of severe nasal obstruction, a nasal olive can be introduced into the other nostril to reduce resistance and facilitate flow therethrough.

As mentioned above, a gas flow of at least 20 litres per minute can easily be achieved by the delivery device. By providing a sufficiently high gas flow, all parts, or at least a larger part, of the complex nasal airway can be penetrated by the substance. In one embodiment the delivery device can include an indicator for indicating the magnitude of the gas flow.

The dimensions of the posterior passage and opening behind the nasal septum are almost always larger than the opening in the flow resistor. Thus, it is only in very rare cases of complete occlusion of the outlet nostril that the pressure in the posterior region of the nasal airway will approach the positive pressure in the oral cavity and jeopardise the velum closure. In the case of severe obstruction, insertion of the nosepiece in the occluded nostril may reduce the resistance and allow successful flushing.

After having flushed the nasal airway in one direction, the same procedure can be repeated from the other nostril. In this way both nasal cavities are irrigated in both directions. This is a unique feature of this device. This embodiment secures an improved distribution of the substance to all parts of the nasal mucosa, and in particular to the posterior region which is difficult to access using current techniques.

In a preferred embodiment, where the substance is in solid form, such as a powder, then a filter can be employed if high humidity represents a problem for administration of the solid.

The substance can be a single compound or a mixture of compounds, which compounds can be in any suitable form, such as a powder form, a solution, or a suspension.

The substance can be any suitable substance for delivery to a human or in some cases an animal. The substance may be for delivery for action in any part of the nasal airway, or in any of the surrounding tissues or organs. Also, the substance may be for delivery for action in a region remote from the nasal airway.

Preferably, the substance is for delivery for subsequent action in any part of the nasal airway, or in any of the surrounding tissues or organs.

The substance may have a beneficial medical effect, which can include a diagnostic effect, a therapeutic effect, a prophylactic effect, and a cleansing effect such as the removal of particles, crusts, secretions, debris, etc. Preferably, the substance has a therapeutic effect.

Preferably, the substance is a pharmaceutical. The pharmaceutical can be admixed with any suitable carrier, diluent, excipient or adjuvant.

Preferably, the pharmaceutical is for the treatment of any one or more of the above-mentioned conditions. By way of example, the pharmaceutical may be for the treatment of any allergic and non-allergic inflammatory disease.

Typical pharmaceuticals for administration include, but are not limited to, steroids, anti-histamines, cromoglycates, anti-allergic pharmaceuticals, anti-inflammatory pharmaceuticals, anti-leucotriens, lactation promoters such as oxytocin, and anti-migraine pharmaceuticals.

By achieving a more optimal delivery, the delivery device of the present invention improves the effect of topical pharmaceuticals in the treatment of upper airway pathologies, such as hypertrophic adenoids and chronic secretory otitis media.

Aside from pharmaceuticals, the device can also be used to irrigate or cleanse the nasal airway with saline or other solutions, preferably containing oils or herbs.

The device of the present invention can be tailored to suit particular needs. For example, balloons or pop-up figures can easily be integrated to provide a semi-quantitaive indication of the flow rate and to improve the acceptability and ease of administration in small children.

Only in the rare circumstances when the nasal resistance is too high to achieve a gas flow through the nasal airway, even after attempting to expand the nasal cavities, would insufflation be jeopardised. In those cases, pre-treatment with decongestants may be necessary.

The delivery device may also be used as a nasal lavage means in the collection of mediators and cells that originate from the nasal mucosa for, for example, diagnostic analysis or research purposes. In this respect, the mediators and cells can be expelled into a suitable collecting vessel after the nasal airway has been exposed to a suitable solution, such as a saline solution, for a sufficient period of time to ensure sufficient transfer of the mediators and cells into the solution. This use of the device may require the use of a gas flow separate to the exhaled air flow as the flow used to flush the nasal airway. For this lavage purpose, use of the exhaled air may not be possible as the lower airways may contain mediators, secretions and cells originating from the lower airways which would contaminate the nasal sample. For this particular use, and as indicated, the fluid escaping from the outlet nostril may be collected in a vessel. Alternatively, the fluid escaping from the outlet nostril may be absorbed onto a filter for direct or delayed analysis. Indeed, such filters and the like may even yield an almost immediate detection result of certain organisms, such as bacteria, viruses or mediators.

The delivery device of the present invention is advantageous for a number of reasons.

Notably, the delivery device provides a very simple and efficient means of delivering substances, such as pharmaceuticals, saline solutions, etc, into the nasal airway. In this respect, the device utilises very simple technology with few movable parts, making the device relatively inexpensive to mass produce. In addition, the device of the present invention can be made in a disposable form, thus avoiding the need for the delivered substance to include any preservatives.

The present invention also eliminates the need for the subsequent flushing or spraying methods that are associated with some of the prior art devices. However, for some applications it may still be desirable to perform a subsequent flushing or spraying operation.

The delivery device of the present invention is advantageous as, in use, the tight seal between the nosepiece and the one nostril ensures a prolonged penetration of the complex nasal airway, a bi-directional gas flow through the nasal cavities and deposition of the substance in the contralateral nasal passage.

In accordance with the present invention, closure of the velum will normally be maintained. The delivered gas flow enters one nasal cavity, passes beyond the posterior margin of the nasal septum, making a 180 degree turn behind the posterior margin of the nasal septum, and passes out the other nasal cavity. This re-direction of the gas flow results in a better deposition of substance, notably pharmaceuticals, to the posterior regions of the nasal turbinates and the nasal mucosa.

In addition, the bi-directional deposition of substances, typically pharmaceuticals, and irrigation will also better reach all sinus ostia due to the anatomic locations and orientation of the sinus ostia, which can improve sinus ventilation and drainage which is essential to treat sinusitis and frequently accompanies inflammation of the nasal mucosa. In this respect, the ostia and tubes to the ethmoidal and sphenoidal sinuses are located in the posterior region of the nasal airway and the uncinate projections covering the infundibulum, housing the maxillary, frontal and anterior ethmoid ostia, are tilted backwards. Furthermore, the driving positive pressure used will increase the deposition of pharmaceuticals at the sinus ostia, the sinus tubes leading into the sinuses and even in the sinuses themselves.

In addition, the 180 degree re-direction of the flow behind the nasal septum particularly increases the deposition of substance on the roof of the nasopharynx where the adenoid is located and in proximity to the location of the tubal ostia to the auditory tubes connecting the nasopharynx and the middle ears. By way of example, steroids have been shown to reduce the size of hypertrophic adenoids which are commonly found in paediatric subjects and can have a positive effect on secretory otitis media. Deposition of topical decongestants closer to the tubal ostia may also more efficiently decongest the auditory tubes and relieve the negative pressure in the middle ears which accompanies rhinitis and predisposes paediatric subjects to secretory otitis media and the consequential reduced hearing. Surgery for enlarged adenoids is frequently performed in children and the improved medical therapy of the present invention should reduce the necessity for surgery.

A further advantage is that possible surplus substance, that is, substance which is not deposited, will be expelled out of the contralateral nostril, where it may be collected, if desired, and consequently not continue to the oral cavity and down into the gut as is the case with many other delivery techniques. In this way, the discomfort, and more importantly, the undesirable systemic exposure to the substance, where the substance is a medicament, will be reduced.

Also, with the present invention, irrigation by saline or other solutions can be performed more efficiently and with less spill and discomfort than the current techniques used for irrigation and flushing of the nasal airway.

Further, the present invention provides for simple and comfortable irrigation of the nasal mucosa with solutions, such as saline solutions, and other oils to remove secretions from the nasal mucosa and promote mucocilary function.

Still further, the present invention provides a simple and effective means for the lavage of the nasal mucosa, such as to collect and diagnose mucosal entities, such as bacteria, viruses, cell components and inflammatory mediators.

Still yet further, the exposure of the nasal mucosa to a positive pressure, particularly a dynamic positive pressure, will open the narrow, and sometimes occluded, parts of the nasal passages, rather than cause a dynamic collapse which may happen during sniffing and inhalation. The dynamic positive pressure is at least 5 cm $H_2O$, preferably at least 50 cm $H_2O$, more preferably at least 100 cm $H_2O$, still more preferably at least 200 cm $H_2O$, yet more preferably 400 cm $H_2O$ and still yet more preferably 500 cm $H_2O$. The dynamic positive pressure achieved by the present invention can be contrasted with the static pressure provided by the Valsalva procedure where there is no flow through the nasal airway.

In addition, the use of warm and humid air as the gas flow is likely to be better tolerated and cause less irritation than room air or outdoor air, especially in cold climates.

Where the substance is a dry powder, then the humidity of the exhaled air may, in some instances, cause agglomeration of the powder. Naturally, this will depend on the properties of the powder and the construction of the device, in particular the dispersion chamber. In order to alleviate this specific problem, the surface properties of the powder could be modified, or the device could include a moisture-absorbing element, typically containing a desiccant such as silica, disposed upstream of the dispersion chamber. In a preferred embodiment the moisture-absorbing element could be provided as a filter which acts as the flow resistor.

In a preferred embodiment, in order to ensure that agglomeration of powder would not impede the use of direct insufflation of warm, humid exhaled air, the delivery device comprises transfer means which creates a gas flow of drier air, such as atmospheric air, as the delivery flow to the nasal airway. Such transfer means, which could be mechanical in nature, utilises the energy of the exhaled air to drive the atmospheric room air at the required flow rate, if necessary, to disperse the substance in the delivered air flow. In this embodiment agglomeration will be prevented or at least reduced to the same level as currently exhibited by dry powder inhalers.

If desired, the distribution of the substance delivered to the nasal airway could be studied using standard techniques. By way of example, use could be made of acoustic rhinometry or coloured fluids. The distribution of the delivered substance could even be determined by video endoscopy. In addition, or in the alternative, distribution studies could also be performed by using appropriate radioactive materials and following the passage in the nasal cavities. The results of these studies could be used to optimise the flow rate, the shape or dimension of the device, in particular the nosepiece geometry, and the particle size distribution of the substance. The results of these studies could even be used to optimise subject acceptance.

As already indicated, the delivery device may include a balloon or a similar pop-up device for indicating that the desired positive pressure has been attained, which balloon or pop-up device may improve the compliance in small children who are reluctant to use the device.

Alternatively, for particularly young children, the entraining gas flow can be provided by the exhalation air flow of another person, such as a parent, or even by the use of a pump or the like, while the child creates the required positive pressure in the oral cavity by inflating a balloon or pop-up device.

Figure 5:
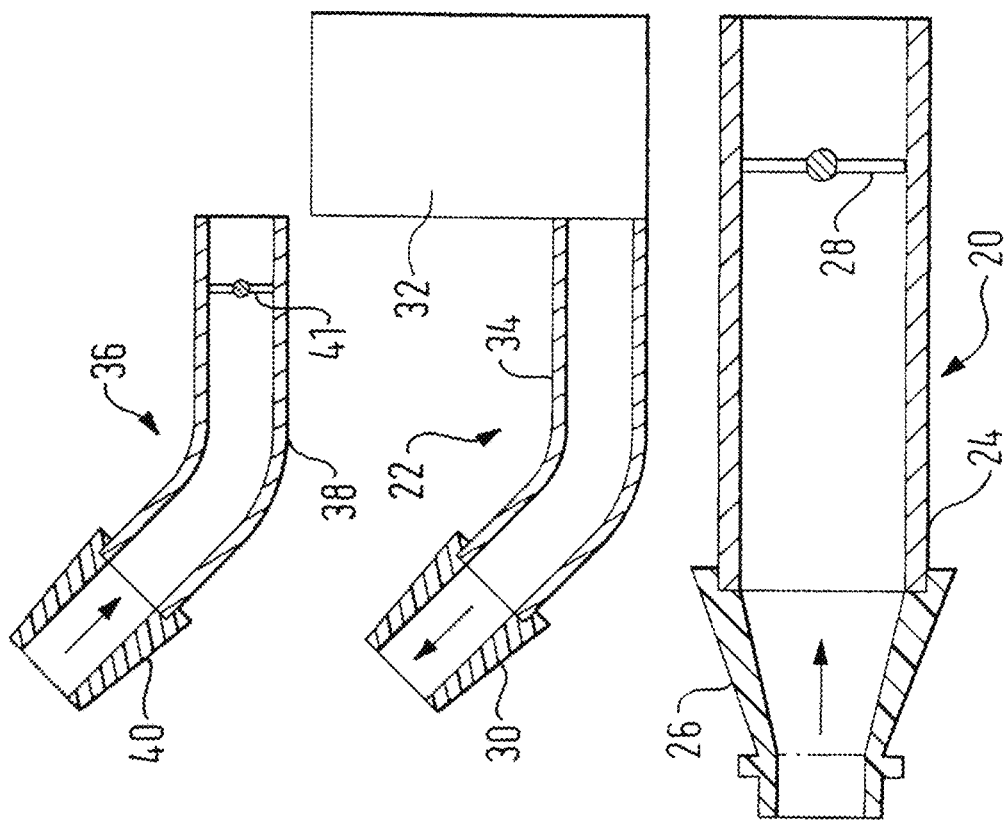
Figure 4:
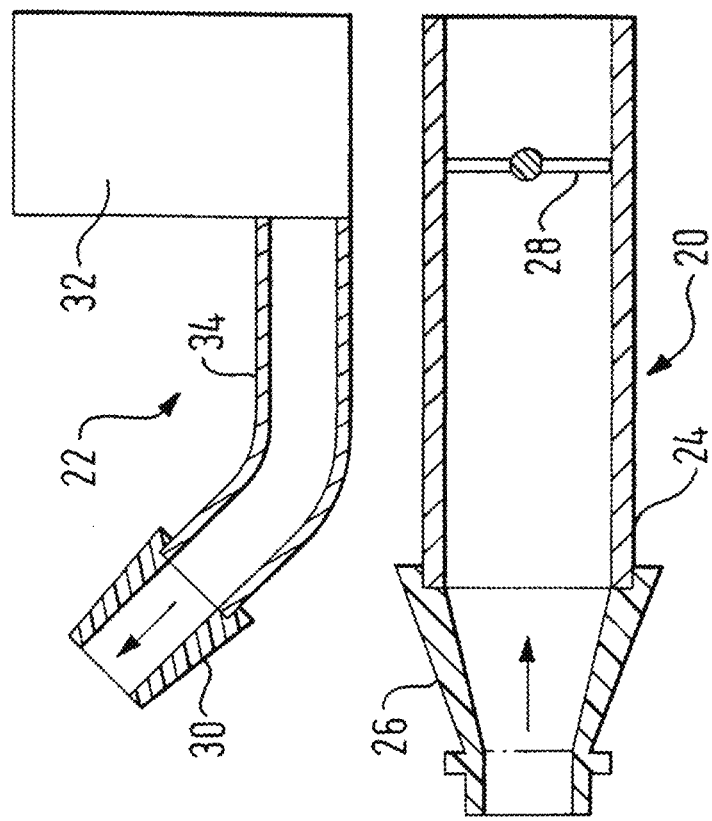
Figure 7:
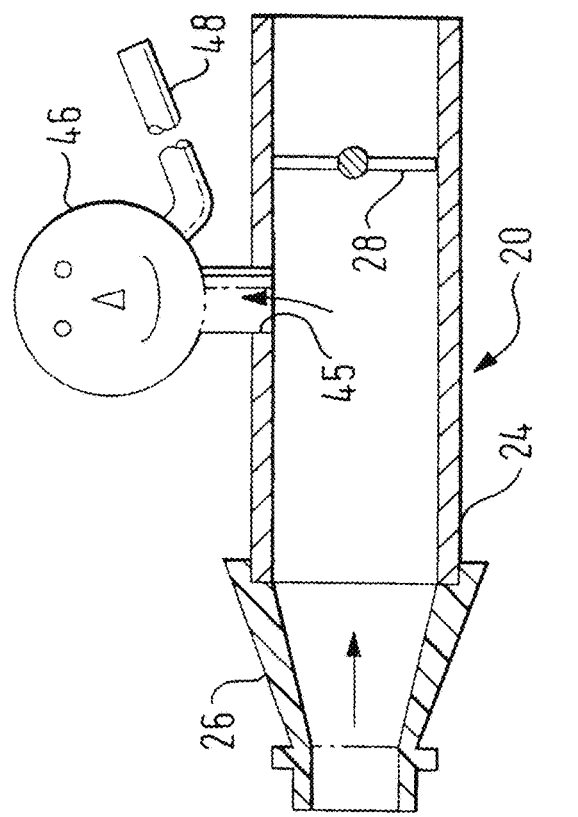
Figure 6:
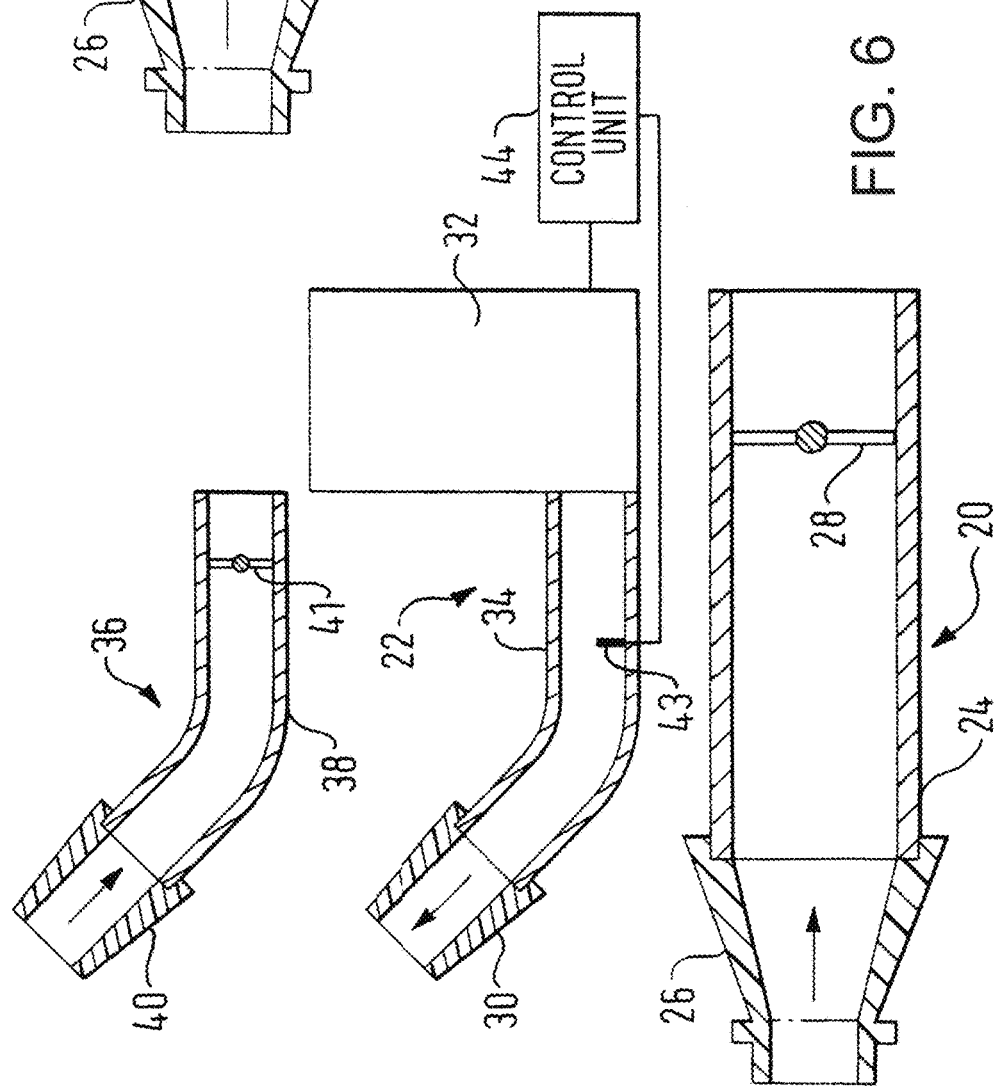
Figure 8:
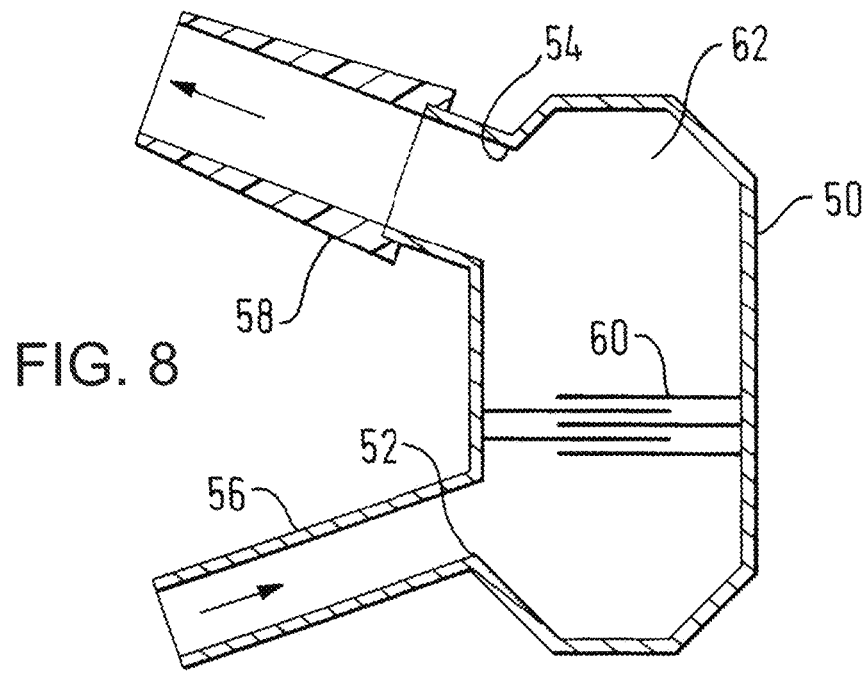
Figure 9:
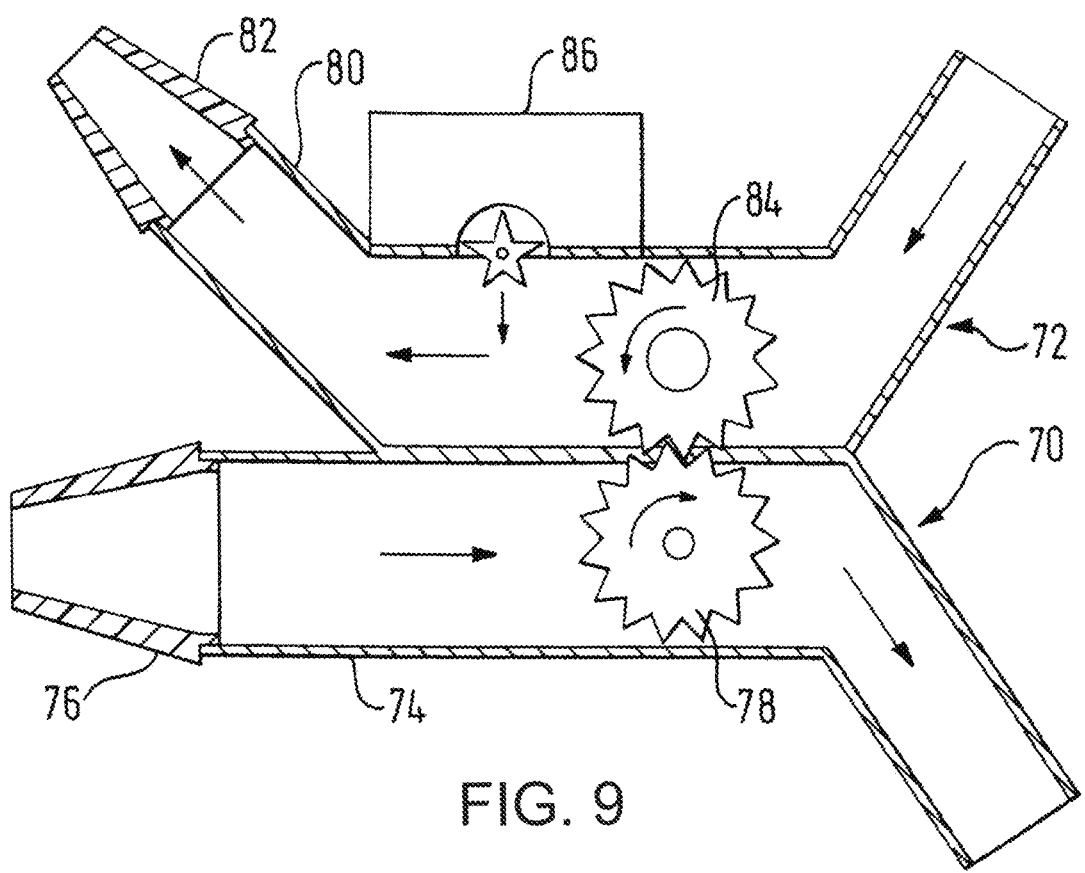
Figure 11:
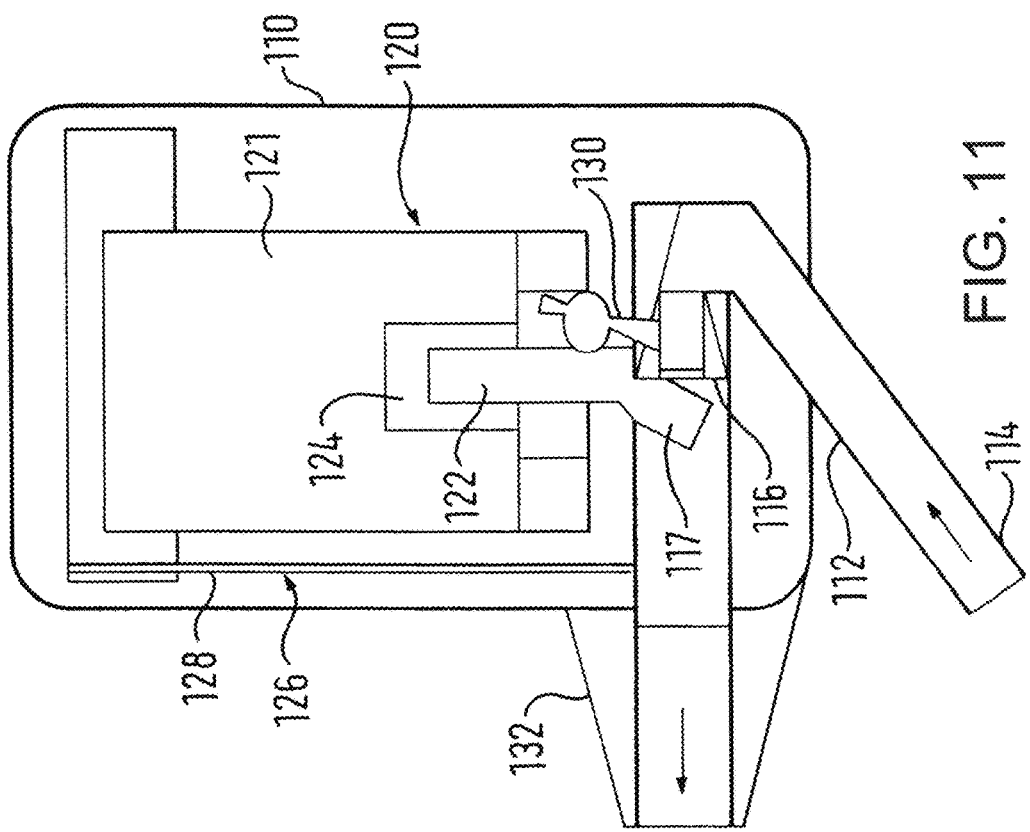
Figure 10:
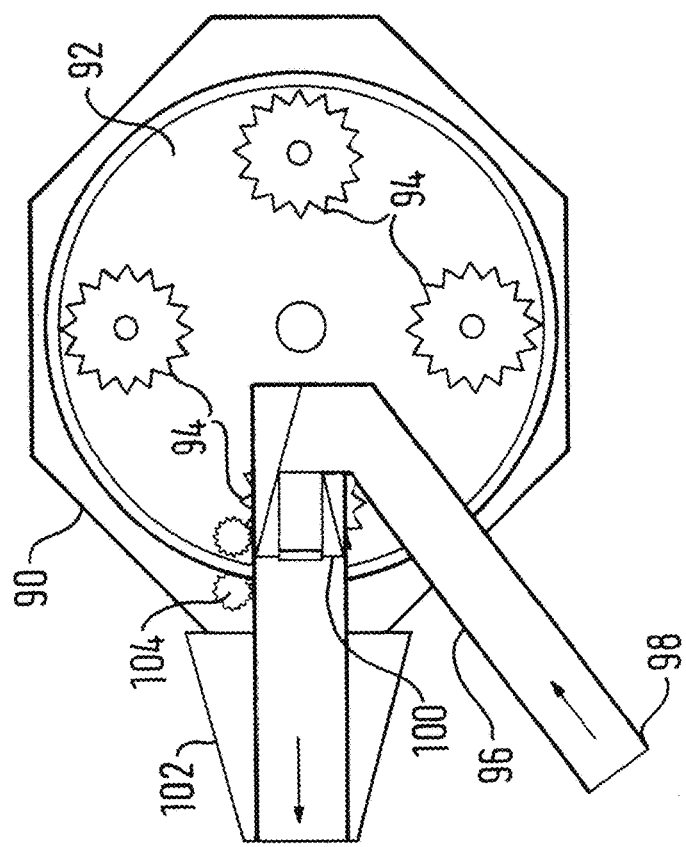

Preferred embodiments of the present invention will now be described hereinbelow by way of example only with reference to the accompanying drawings, in which:

FIG. 3 schematically illustrates the anatomy of the upper respiratory tract of a human subject;

FIG. 4 schematically illustrates a delivery device in accordance with a first embodiment of the present invention;

FIG. 5 schematically illustrates a delivery device in accordance with a second embodiment of the present invention;

FIG. 6 schematically illustrates a delivery device in accordance with a third embodiment of the present invention;

FIG. 7 schematically illustrates a modified delivery unit for the above-described first to third embodiments of the present invention;

FIG. 8 schematically illustrates a delivery device in accordance with a fourth embodiment of the present invention;

FIG. 9 schematically illustrates a delivery device in accordance with a fifth embodiment of the present invention;

FIG. 10 schematically illustrates a delivery device in accordance with a sixth embodiment of the present invention; and FIG. 11 schematically illustrates a delivery device in accordance with a seventh embodiment of the present invention.

FIG. 4 illustrates a delivery device in accordance with a first embodiment of the present invention.

The delivery device comprises an oral exhalation unit 20 and a substance delivery unit 22. In this embodiment the oral exhalation unit 20 and the delivery unit 22 are provided as separate components, but alternatively could be detachably coupled, for example by means of Velcro™ fasteners, connected, for example by means of screws and/or rivets, or even integrally formed.

The oral exhalation unit 20 comprises a tubular section 24 and a mouthpiece 26 attached to one end of the tubular section 24. The mouthpiece 26, which in use is gripped in the lips of a user, is formed separately of the tubular section 24 to allow for replacement, but could alternatively be integrally formed. In this embodiment the mouthpiece 26 is a snap fit on the tubular section 24, but could equally be a screw fit. The tubular section 24 includes a flow resistor 28, in this embodiment a fixed baffle plate, configured to provide a sufficient resistance to exhalation therethrough by a subject as to cause the generation of a positive pressure in the oral cavity of the subject and the closure of the velum on exhalation by the subject. In alternative embodiments the flow resistor 28 could be a movable member, such as a biased flap, a resilient membrane or a damped wheel.

The delivery unit 22 comprises a nosepiece 30, in this embodiment formed of a resilient material such as a polymeric material, for providing a tight sealing fit in one of the nostrils of the subject, a medicament supply unit 32 for supplying a gas flow entraining medicament at a predetermined pressure sufficient to open a flow path beyond the posterior margin of the nasal septum when delivered into one of the nasal cavities of the subject, and a tubular section 34 coupling the nosepiece 30 and the medicament supply unit 32. In a preferred embodiment the nosepiece 30 can include an external olive or be shaped to cause the anterior region of the nasal cavity into which the nosepiece 30 is inserted to be enlarged. In a particularly preferred embodiment the nosepiece 30 can be shaped, for example by including swirl-inducing projections, to provide the exiting gas flow with an optimal flow pattern and particle size distribution. The nosepiece 30 is formed separately of the tubular section 34 to allow for replacement, but could alternatively be integrally formed. In this embodiment the nosepiece 30 is a snap fit on the tubular section 34, but could equally be a screw fit. The medicament supply unit 32 can comprise an aerosol spray generator for generating an aerosol spray of liquid droplets containing medicament, such as provided by a pressurised metered dose inhaler, or a pressurised gas source for entraining a metered dose of a dry powder containing medicament loaded thereinto, which powder could alternatively be loaded into a compartment in the tubular section 34.

In use, a subject grips the mouthpiece 26 in his or her lips and fits the nosepiece 30 into one of his or her nostrils. The subject then exhales through the mouthpiece 26, the flow of which exhaled air is resisted by the flow resistor 28 in the tubular section 24 such as to develop a positive pressure in the oral cavity of the subject, with the positive pressure being such as to develop a pressure differential across the velum sufficient to cause closure of the velum of the subject. The applicant has established that a positive pressure differential between the oral cavity and the nasal airway of about 5 cm $H_2O$ is required to maintain the velum in the closed position. The applicant has further established that a subject should be able to maintain a flow rate of about 3 to 30 litres per minute for about 1 to 20 seconds, with flow rates of about 10 to 20 litres per minute and delivery times of about 2 to 5 seconds being considered as optimal. After closure of the velum, the medicament supply unit 32 is then actuated to deliver a gas flow entraining medicament through the nosepiece 30 and into the nasal airway of the subject. As mentioned above, this gas flow is at such a pressure as to open a communication path beyond the posterior margin of the nasal septum such that the gas flow flows through the one nasal cavity, around the posterior margin of the nasal septum, in effect being re-directed through an angle of 180 degrees, and out of the other nasal cavity. Again, as already described, this bi-directional flow provides for a much enhanced deposition of the medicament in the posterior region of the nasal airway.

In one modification, the medicament supply unit 32 can be omitted from the delivery unit 22, and instead a metered dose of dry powder loaded into a compartment in the tubular section 34, with the delivery air flow being provided by another person, such as the parent of a paediatric subject, blowing into the distal end of the tubular section 34.

FIG. 5 illustrates a delivery device in accordance with a second embodiment of the present invention.

The delivery device comprises the oral exhalation unit 20 and the delivery unit 22 of the above-described first embodiment, and an outlet unit 36 for fitting to the other nostril of a subject to which the delivery unit 22 is fitted.

The outlet unit 36 comprises a tubular section 38 and a nosepiece 40, in this embodiment formed of a resilient material such as a polymeric material, attached to one end of the tubular section 38 for providing a tight sealing fit in the other nostril of the subject. The nosepiece 40 is formed separately of the tubular section 38 to allow for replacement, but could alternatively be integrally formed. In this embodiment the nosepiece 40 is a snap fit on the tubular section 38, but could equally be a screw fit. As with the nosepiece 30 of the delivery unit 22, in a preferred embodiment the nosepiece 40 can include an external olive or be shaped to cause the anterior region of the other nasal cavity into which the nosepiece 40 is inserted to be enlarged. The tubular section 38 includes a flow resistor 41, in this embodiment a baffle plate, configured to provide a sufficient flow resistance to an exhalation flow therethrough as to cause the generation of a dynamic positive pressure in the nasal airway. In a preferred embodiment the flow resistor 41 is adjustable to allow for adjustment of the level of the resistance and hence provide control of the dynamic pressure in the nasal airway. In alternative embodiments the flow resistor 41 could be a movable member, such as a biased flap, a resilient membrane or a damped wheel.

In a preferred embodiment the outlet unit 36 includes an indicator for providing at least one of a visual or audible signal on achieving a predetermined positive pressure upstream thereof, that is, in the nasal airway. Preferably, the indicator comprises a whistle. In this way, the subject is provided with positive feedback of proper use of the device.

Use of the delivery device of this embodiment is the same as for the above-described first embodiment. However, as mentioned above, by the provision of the flow resistor 41 in the outlet unit 36 downstream of the outlet nostril of the subject, a positive dynamic pressure is maintained in the nasal airway. This positive pressure advantageously acts to dilate the various ostia in the nasal airway, such as the sinus ostia and the tubal ostia, and the associated tubes, namely the sinus tubes and the auditory tubes, so as to promote the delivery of medicament thereto. Further, this positive pressure acts to improve deposition on the adenoid which can often obstruct the tubal ostia, the middle meatus which is a common location of nasal polyps, and the cleft to the olfactory cells.

FIG. 6 illustrates a delivery device in accordance with a third embodiment of the present invention.

The delivery device is very similar to that of the delivery device of the above-described second embodiment, and thus, in order to avoid unnecessary duplication of description, only the differences will be described in detail, with like parts being designated by like reference signs. This delivery device differs only in further comprising a pressure sensor 43, in this embodiment a pressure-sensitive spring or membrane, located in the tubular section 34 of the delivery unit 22 downstream of the medicament supply unit 32, and a control unit 44 coupled to the sensor 43 and the medicament supply unit 32.

The control unit 44 is configured to control the flow rate of the delivery gas supplied by the medicament supply unit 32 in order to optimise the particle deposition efficiency in the nasal airway regardless of the degree of nasal congestion. As mentioned hereinabove, by maintaining an optimum flow rate in the nasal airway, the deposition efficiency of the medicament-containing particles is increased, referred to as the particle deposition efficiency. If, ordinarily, a flow rate of about 15 litres per minute is required to maximise the particle deposition efficiency, then in a congested nasal airway a lower flow rate, possibly 10 litres per minute, would be required and in an open nasal airway a higher flow rate, possibly 20 litres per minute, would be required.

Operation of this delivery device is otherwise the same as that of the above-described second embodiment.

FIG. 7 illustrates a modified oral exhalation unit 20 for the delivery devices of the above-described embodiments.

Figure 46:
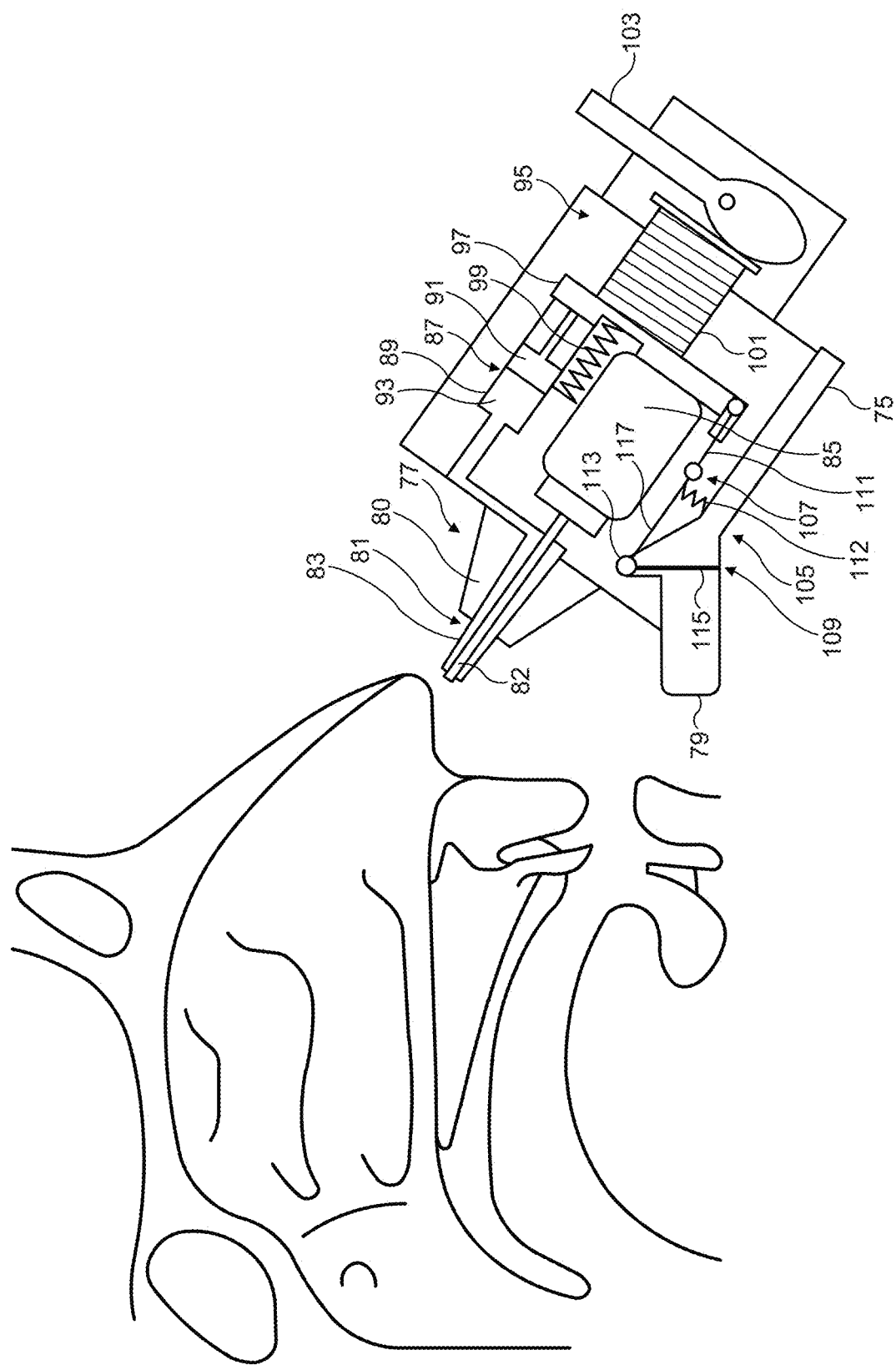

This modified oral exhalation unit 20 differs in that the tubular section 24 includes a lateral opening 45 upstream of the flow resistor 28 and in further comprising, as an indicator, an inflatable FIG. 46 connected to the lateral opening 45, which FIG. 46 when inflated assumes a prominent position in the field of vision of the subject. In FIG. 6, the FIG. 46 is shown inflated. By providing such a display feature, subject compliance, particularly in paediatric subjects, should be improved. The oral exhalation unit 20 further comprises an inflation line 48 connected to the FIG. 46 which allows the FIG. 46 to be further inflated by another person, typically the parent of a paediatric subject, or a pump. In an alternative embodiment, instead of being inflatable, the FIG. 46 could be of any kind which is brought into a prominent position on exhalation by the subject, typically a mechanically or electrically-operated figure. In a preferred embodiment the FIG. 46 can be configured so as to be inflated on the subject achieving an optimum exhalation flow rate. In this way, the FIG. 46 acts as an indicator.

Use of the delivery device of this embodiment is the same as that of the above-described first embodiment. However, on exhaling through the mouthpiece 26, the developed pressure causes the FIG. 46 to be inflated and assume a prominent position in the field of vision of the subject. This appearance of the FIG. 46 is particularly appealing for paediatric subjects as the fun element of inflating the FIG. 46 can alleviate any unnecessary anxiety.

FIG. 8 illustrates a delivery device in accordance with a fourth embodiment of the present invention.

The delivery device comprises a chamber 50 which includes an inlet 52 and an outlet 54, a mouthpiece 56 connected to the inlet 52 and a nosepiece 58 connected to the outlet 54. The nosepiece 58 is configured to provide a tight sealing fit in one of the nostrils of a subject. The chamber 50 includes a flow resistor 60, in this embodiment a plurality of baffle plates, and a medicament-receiving compartment 62 downstream of the flow resistor 60 for containing a metered dose of a dry powder containing medicament to be delivered to the nasal airway of a subject. In this embodiment the nosepiece 58 is formed of a resilient material such as a polymeric material. In a preferred embodiment the chamber 50 may include a desiccant. In a preferred embodiment the flow resistor 60 can be provided by a moisture-absorbing filter.

In use, a subject grips the mouthpiece 56 in his or her lips and fits the nosepiece 58 into one of his or her nostrils. The subject then exhales through the mouthpiece 56, the flow of which exhaled air is resisted by the flow resistor 60 in the chamber 50 and the resistance of the nasal airway such as to develop a positive pressure in the oral cavity of the subject sufficient to cause closure of the velum. The exhaled air, after passing the flow resistor 60, then entrains the powdered medicament in the medicament-receiving compartment 62, and this air flow entraining medicament then passes through the nosepiece 58 into the nasal airway of the subject. The exhaled air entering the nasal airway is at a pressure sufficient to open a communication path beyond the posterior margin of the nasal septum such that the air flow flows through the one nasal cavity, around the posterior margin of the nasal septum, in effect being re-directed through an angle of 180 degrees, and out of the other nasal cavity. Again, as already described, this bi-directional flow provides for a much enhanced deposition of the medicament in the posterior margin of the nasal airway.

In a preferred embodiment the delivery device includes a pressure-triggered valve, preferably located in the mouthpiece 56, which is configured to open only when a predetermined positive pressure has been developed by the exhalation of the subject, typically at a positive pressure of about 10 cm $H_2O$. This configuration advantageously avoids the possibility of medicament being delivered to the nasal airway with the velum in the open position and thereby reduces the risk of undesirably depositing medicament outside the nasal airway.

In another preferred embodiment, similarly to third-described embodiment, the delivery device can include an outlet unit for providing a flow resistor downstream of the other nostril of the subject such as to maintain a positive dynamic pressure in the nasal airway.

FIG. 9 illustrates a delivery device in accordance with a fifth embodiment of the present invention.

The delivery device comprises an oral exhalation unit 70 through which a subject exhales to close his or her velum and a medicament delivery unit 72 for supplying an air flow entraining medicament to the nasal airway of the subject.

The oral exhalation unit 70 comprises a tubular section 74 and a mouthpiece 76 attached to one end of the tubular section 74. The mouthpiece 76, which is gripped in the lips of the subject, is formed separately of the tubular section 74 to allow for replacement, but could alternatively be integrally formed therewith. In this embodiment the mouthpiece 76 is a snap fit on the tubular section 74, but could equally be a screw fit. The tubular section 74 includes a flow resistor 78, in this embodiment a gearwheel, configured to rotate on exhalation by the subject and yet provide sufficient resistance to the exhalation flow as to cause the generation of a positive pressure in the oral cavity of the subject sufficient to maintain the required positive pressure differential between the oral cavity and the nasal airway and thereby maintain the velum in the closed position.

The delivery unit 72 comprises a tubular section 80 and a nosepiece 82, in this embodiment formed of a resilient material such as a polymeric material, for providing a tight sealing fit in one of the nostrils of the subject, attached to one end of the tubular section 80. The nosepiece 82 is formed separately of the tubular section 80 to allow for replacement, but could alternatively be integrally formed therewith. In this embodiment the nosepiece 82 is a snap fit on the tubular section 80, but could equally be a screw fit. In a preferred embodiment the nosepiece 82 can include an external olive or be shaped to cause the anterior region of the nasal cavity, into which the nosepiece 82 is inserted, to be enlarged. In a particularly preferred embodiment the nosepiece 82 can be shaped, for example by including swirl-inducing projections, to provide the exiting air flow with an optimal flow pattern and particle size distribution. The tubular section 80 includes an impeller 84 coupled to the gearwheel 78 in the tubular section 74 of the oral exhalation unit 70, such as to be rotated on rotation of the gearwheel 78 to draw air into the tubular section 80 and provide an air flow therethrough at a pressure sufficient to open the flow path beyond the posterior margin of the nasal septum when delivered into one of the nasal cavities of the subject.

The delivery unit 72 further comprises a dispensing unit 86 for dispensing a metered dose of a dry powder containing medicament to the tubular section 80 upstream of the impeller 84. In this embodiment the dispensing unit 86 is manually actuated to supply a metered dose of dry powder containing medicament into the tubular section 80, but could alternatively be configured to the driven by the gearwheel 78 so as to avoid the need for any manual intervention on the part of the subject.

In use, a subject grips the mouthpiece 76 in his or her lips and fits the nosepiece 82 into one of his or her nostrils. The subject then exhales through the mouthpiece 76, the flow of which exhaled air is resisted by the gearwheel 78 such as to develop a positive pressure in the oral cavity of the subject sufficient to cause the velum of the subject to close. The exhaled air causes rotation of the gearwheel 78 which in turn causes rotation of the impeller 84, and the rotation of the impeller 84 develops an air flow through the tubular section 80 which entrains the metered dose of dry powder containing medicament and delivers the same through the nosepiece 82 to the nasal airway of the subject. As mentioned above, this air flow is at a pressure sufficient to open a communication path beyond the posterior margin of the nasal septum such that the air flow flows through the one nasal cavity, around the posterior margin of the nasal septum, in effect being re-directed through an angle of 180 degrees, and out of the other nasal cavity. Again, as already described, this bi-directional flow provides for a much enhanced deposition of the medicament in the posterior region of the nasal cavity.

In a preferred embodiment the gearwheel 78 is configured such that rotation thereof is prevented until a predetermined flow rate has been developed which is sufficient to ensure that the entraining gas flow developed by the impeller 84 is optimal. This configuration advantageously ensures an optimal particle deposition efficiency and avoids the possibility of medicament being delivered to the nasal airway with the velum in the open position so as to reduce the risk of undesirably depositing medicament outside the nasal airway.

FIG. 10 illustrates a delivery device in accordance with a sixth embodiment of the present invention.

The delivery device comprises a housing 90 for housing a blister pack element 92 which includes a plurality of blisters 94 therein, each containing powder containing medicament, and a tubular section 96 in communication with one of the blisters 94 when open, one end of which tubular section 96 provides a mouthpiece 98 which in use is gripped in the lips of a subject. The tubular section 96 includes an element 100 movably disposed therein between a first, normally closed position and a second, open position. In this embodiment the element 100 comprises a propeller or the like rotatably mounted on a threaded shaft and normally biased to the closed position by a compression spring. The element 100 is configured both to function as a flow resistor and a valve. In this embodiment the element 100 is configured to move to the medicament-releasing open position by rotation along the threaded shaft against the bias of the compression spring, with the powder being entrainable by an air flow only when the exhalation flow exceeds a predetermined flow rate. The flow rate, preferably in the range of about 5 to 20 litres per minute, at which the powder containing medicament is entrained by the air flow is a function, in inverse relation, to the driving pressure which is itself a function of the nasal resistance as described hereinabove. As will be understood, this configuration advantageously provides for an optimal particle deposition efficiency in releasing the powder containing medicament at the optimal flow rate, and avoids the possibility of medicament being delivered to the nasal airway with the velum in the open position.

The delivery device further comprises a nosepiece 102, in this embodiment formed of a resilient material such as a polymeric material, for providing a tight sealing fit in one of the nostrils of the subject attached to the other end of the tubular section 96 downstream of the element 100. The nosepiece 102 is formed separately of the tubular section 96 to allow for replacement, but could alternatively be integrally formed therewith. In this embodiment the nosepiece 102 is a snap fit on the tubular section 96, but could equally be a screw fit. In a preferred embodiment the nosepiece 102 can include an external olive or be shaped to cause the anterior region of the nasal cavity into which the nosepiece 102 is inserted to be enlarged. In a particularly preferred embodiment the nosepiece 102 can be shaped, for example by including swirl-inducing projections, to provide the exiting air flow with an optimal flow pattern and particle size distribution.

The delivery device further comprises a blister opening mechanism 104 for opening the blister 94 in communication with the tubular section 96. In this embodiment the blister opening mechanism 104 is manually operated by the subject prior to delivery.

In use, a subject grips the mouthpiece 98 in his or her lips and fits the nosepiece 102 into one of his or her nostrils. The subject then exhales through the mouthpiece 98, the flow of which exhaled air is resisted by the element 100 until a predetermined flow rate has been achieved. Once this predetermined flow rate has been achieved, at which flow rate the velum is in the closed position, the element 100 is in the open position and the exhaled air flow entrains the powdered medicament in the blister 94 and delivers the same through the nosepiece 102 to the nasal airway. The driving pressure of this air flow is at a level sufficient to maintain a communication path beyond the posterior margin of the nasal septum such that the air flow flows through the one nasal cavity, around the posterior margin of the nasal septum, in effect being re-directed through an angle of 180 degrees, and out of the other nasal cavity. Again, as already described, this bi-directional flow provides for a much enhanced deposition of the medicament in the posterior margin of the nasal cavity.

In a preferred embodiment the delivery device includes a blister pack advancement mechanism, operated by movement of the mouthpiece 98, for rotating the blister pack element 92 such that another unused blister 94 is located at the delivery position. In a particularly preferred embodiment the blister pack advancement mechanism can be coupled to the blister opening mechanism 104 such as automatically to open the blister 94, and thereby avoid the need for any further intervention by the subject.

In one modification, similarly to the above-described modification of the first embodiment as illustrated in FIG. 5, the delivery device can include an outlet unit for providing a flow resistor downstream of the other nostril of the subject such as to maintain a positive dynamic pressure in the nasal airway.

In another modification, the blister pack element 92 can be omitted and the housing 90 instead provided with a chamber which is in communication with the tubular section 96 and into which a metered dose of dry powder containing medicament can be loaded. With this configuration, the powder in the chamber is entrained on the element 100 being driven to the second position and the blister pack advancement mechanism is configured to meter a dose of powder containing medicament into the chamber on operation thereof.

As will be understood, in essence, the present invention can be broadly based on any dry powder inhaler, such as the Turbuhaler™ as manufactured by AstraZeneca PLC, the Accuhaler™ as manufactured by Glaxo PLC or the Twisthaler™ as manufactured by Schering AG, where the usual mouthpiece is replaced by a nosepiece and a mouthpiece is provided in communication with the air inlet of the inhaler such as to utilise the air exhaled by a subject as the entraining delivery air.

FIG. 11 illustrates a delivery device in accordance with a seventh embodiment of the present invention.

The delivery device comprises a housing 110 and a tubular section 112 extending through the housing 110, one end of which provides a mouthpiece 114 which in use is gripped in the lips of a subject.

The tubular section 112 includes an element 116 movably disposed therein between a first, normally closed position and a second, trigger position. In this embodiment the element 116 comprises a propeller or the like rotatably mounted on a threaded shaft and normally biased to the closed position by a compression spring. The element 116 is configured to function as a flow resistor, a valve and a trigger for the delivery of an aerosol spray into the tubular section 112 as will be described in detail hereinbelow. In this embodiment the element 116 is configured to move to the medicament-releasing open position, by rotation along the threaded shaft against the bias of the compression spring, only when the exhalation flow exceeds a predetermined flow rate. The flow rate at which the medicament is released, preferably in the range of about 5 to 20 litres per minute, is a function, in inverse relation, to the driving pressure which is itself a function of the nasal resistance as described hereinabove. As will be understood, this configuration advantageously provides for an optimal particle deposition efficiency in releasing the medicament at the optimal flow rate, and avoids the possibility of medicament being delivered to the nasal airway with the velum in the open position.

The tubular section 112 further includes a nozzle block 117 for providing an aerosol spray through the tubular section 112 along the longitudinal axis thereof. As will be described in detail hereinbelow, the nozzle block 117 receives the valve stem 122 of an aerosol canister 120.

The delivery device further comprises a known aerosol canister 120 used to deliver metered volumes of a propellant, preferably a hydrofluoroalkane (HFA) propellant or the like, containing medicament, either as a suspension or as a solution. The aerosol canister 120 comprises a main body 121 which contains a volume of propellant under pressure containing medicament, a valve stem 122 through which the propellant containing medicament is in use delivered on relative movement of the main body 121 and the valve stem 122, and a metering valve 124 for metering a predetermined volume of propellant containing medicament to the valve stem 122 on movement thereof.

The delivery device further comprises a trigger mechanism 126 for relatively moving the main body 121 and the valve stem 122 of the aerosol canister 120 to effect the delivery of a metered volume of propellant containing medicament through the nozzle block 117. In this embodiment the trigger mechanism 126 comprises a resilient element 128 for loading the main body 121 with an actuation force, and a lever assembly 130 coupled to the movable element 116 to cause the release of the actuation force provided by the resilient element 128 on movement of the movable element 116 from the closed position to the trigger position.

The delivery device further comprises a nosepiece 132, in this embodiment formed of a resilient material such as a polymeric material, for providing a tight sealing fit in one of the nostrils of the subject, attached to the other end of the tubular section 112 downstream of the movable element 116. The nosepiece 132 is formed separately of the tubular section 112 to allow for replacement, but could alternatively be integrally formed therewith. In this embodiment the nosepiece 132 is a snap fit on the tubular section 112, but could equally be a screw fit. In a preferred embodiment the nosepiece 132 can include an external olive or be shaped to cause the anterior region of the nasal cavity into which the nosepiece 132 is inserted to be enlarged. In a particularly preferred embodiment the nosepiece 132 can be shaped, for example by including swirl-inducing projections, to provide the exiting air flow with an optimal flow pattern and particle size distribution.

In use, a subject primes the trigger mechanism 126, grips the mouthpiece 114 in his or her lips and fits the nosepiece 132 into one of his or her nostrils. The subject then exhales through the mouthpiece 114, the flow of which exhaled air is resisted by the movable element 116 until a predetermined flow rate has been achieved. Once this predetermined flow rate has been achieved, at which flow rate the velum is in the closed position, the movable element 116 is in the open position, triggering the movement of the lever assembly 130 and hence the relative movement of the main body 121 and the valve stem 122 of the canister 120 to deliver a metered volume of propellant containing medicament to the nozzle block 117 to generate an aerosol spray of liquid droplets containing medicament through the nosepiece 132 to the nasal airway. This aerosol flow is at a pressure sufficient to maintain a communication path beyond the posterior margin of the nasal septum such that the flow flows through the one nasal cavity, around the posterior margin of the nasal septum, in effect being re-directed through an angle of 180 degrees, and out of the other nasal cavity. Again, as already described, this bi-directional flow provides for a much enhanced deposition of the medicament in the posterior margin of the nasal cavity.

As will be understood, in essence, the present invention can be broadly based on any breath-actuated pressurised metered dose inhaler, where the usual mouthpiece is replaced by a nosepiece and a mouthpiece is provided in communication with the air inlet of the inhaler such as both to trigger the triggering mechanism and utilise the air exhaled by a subject as the entraining delivery air.

Finally, it will be understood that the present invention has been described in its preferred embodiments and can be modified in many different ways without departing from the scope of the invention as defined by the appended claims.

Nasal Devices

The present invention relates to a nasal delivery device for and a method of delivering a substance, in particular one of a liquid, as a suspension or solution, or a powder containing a medicament, especially systemic or topical pharmaceuticals, or a vaccine to the nasal airway of a subject.

Figure 12:
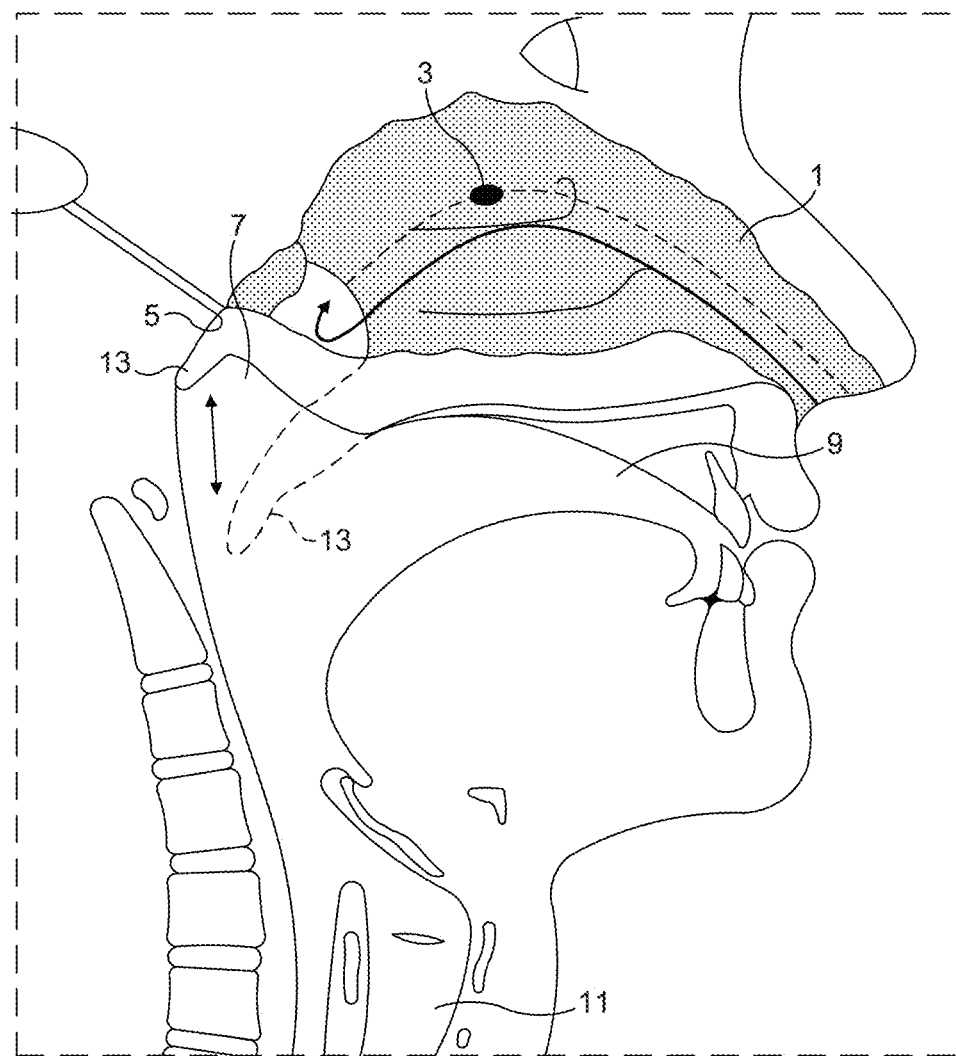

Referring to FIG. 12, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardiovascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modem biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *Helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide improved nasal delivery devices and nasal delivery methods for providing for the improved delivery of a substance to a nasal cavity of subject.

In one aspect the present invention provides a nasal delivery device for delivering substance to a nasal airway of a subject, comprising: a nosepiece for fitting to a nostril of a subject, the nosepiece including a nozzle through which substance is in use delivered to the nasal airway, and at least one inflatable cuff member which is configured to be inflated subsequent to exhalation by the subject; and a delivery unit for delivering substance through the nozzle of the nosepiece.

In another aspect the present invention provides a nasal delivery device for delivering substance to a nasal cavity of a subject, comprising: a nosepiece including a nozzle through which substance is in use delivered to the nasal cavity, and at least one inflatable cuff member which is configured such as, when inflated, to provide a fluid-tight seal between the nosepiece and an inner wall of the nasal cavity of the subject; and a delivery unit for delivering substance through the nozzle of the nosepiece.

In a further aspect the present invention provides a nasal delivery device for delivering substance to a nasal airway of a subject, comprising: a nosepiece for fitting to a nostril of a subject, the nosepiece including a nozzle through which substance is in use delivered to the nasal airway, and at least one cuff member which is configured such as, when fitted in a nasal cavity of the subject, to engage an inner wall of the nasal cavity of the subject and direct at least a distal end of the nozzle towards a site in the nasal airway of the subject; and a delivery unit for delivering substance through the nozzle of the nosepiece.

In yet another aspect the present invention provides a nasal delivery device for delivering substance to a nasal airway of a subject, comprising: a nosepiece for fitting to a nostril of a subject, the nosepiece including a nozzle through which substance is in use delivered to the nasal airway, and at least one cuff member, at least one of the at least one cuff member including at least one lobe which, when the at least one of the at least one cuff member is fitted in the nasal cavity of the subject, extends into a region of the nasal cavity of the subject such as to at least partially obstruct the same and prevent flow thereinto; and a delivery unit for delivering substance through the nozzle of the nosepiece.

In a yet further aspect the present invention provides a nasal delivery device for delivering substance to a nasal airway of a subject, comprising: a nosepiece for fitting to a nasal cavity of a subject, the nosepiece including a first delivery outlet through which substance is in use delivered to the nasal airway of the subject, and at least one second delivery outlet through which at least one gas flow, separate to an exhalation breath of the subject, is in use delivered to the nasal airway of the subject; a delivery unit for delivering substance through the first delivery outlet of the nosepiece; and a gas supply unit for supplying a flow of gas through the at least one second delivery outlet of the nosepiece.

In yet another further aspect the present invention provides a method of delivering substance to a nasal airway of a subject, comprising: fitting a nosepiece to a nasal cavity of a subject, the nosepiece including a nozzle through which substance is delivered to the nasal airway, and at least one inflatable cuff member; inflating the at least one cuff member subsequent to exhalation by the subject; and delivering substance through the nozzle of the nosepiece.

In a still further aspect the present invention provides a method of delivering substance to a nasal cavity of a subject, comprising the steps of: fitting a nosepiece to a nasal cavity of a subject, the nosepiece including a nozzle through which substance is delivered to the nasal cavity, and at least one inflatable cuff member which is configured such as, when inflated, to provide a fluid-tight seal between the nosepiece and an inner wall of the nasal cavity of the subject; and delivering substance through the nozzle of the nosepiece.

In still yet another further aspect the present invention provides a method of delivering substance to a nasal airway of a subject, comprising the steps of: fitting a nosepiece to a nasal cavity of a subject, the nosepiece including a nozzle through which substance is delivered to the nasal airway, and at least one cuff member which is configured such as, when fitted in the nasal cavity of the subject, to engage an inner wall of the nasal cavity of the subject and direct at least a distal end of the nozzle towards a site in the nasal airway of the subject; and delivering substance through the nozzle of the nosepiece.

In a still yet further aspect the present invention provides a method of delivering substance to a nasal airway of a subject, comprising the steps of: fitting a nosepiece to a nasal cavity of a subject, the nosepiece including a nozzle through which substance is delivered to the nasal airway, and at least one cuff member, at least one of the at least one cuff member including at least one lobe which, when the at least one of the at least one cuff member is fitted in the nasal cavity of the subject, extends into a region of the nasal cavity of the subject such as to at least partially obstruct the same and prevent flow thereinto; and delivering substance through the nozzle of the nosepiece.

In a still yet another further aspect the present invention provides a method of delivering substance to a nasal airway of a subject, comprising the step of: delivering substance through a first delivery outlet and at least one gas flow, separate to an exhalation breath of a subject, through at least one second delivery outlet into the nasal airway of the subject.

Figure 13:
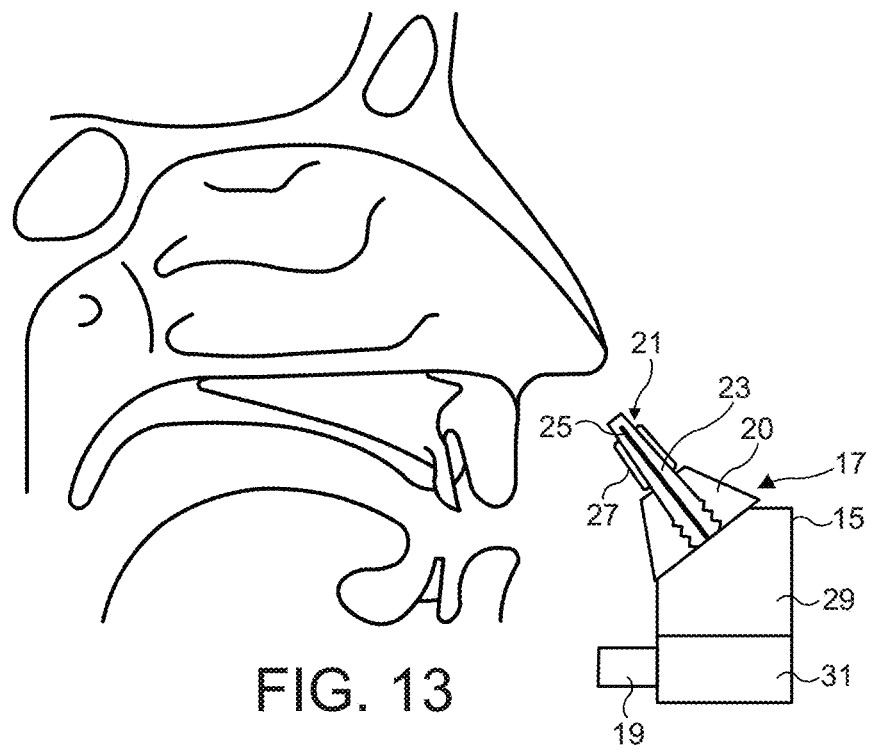
Figure 14:
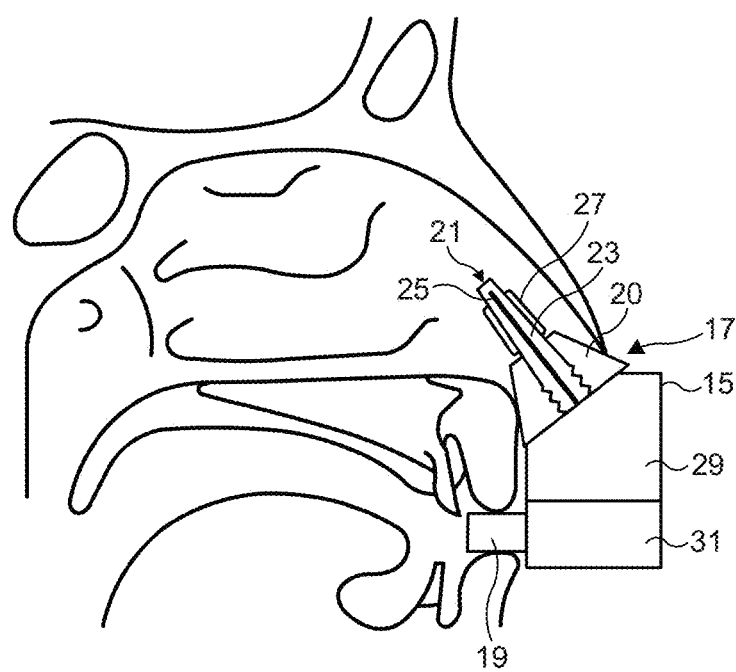
Figure 15:
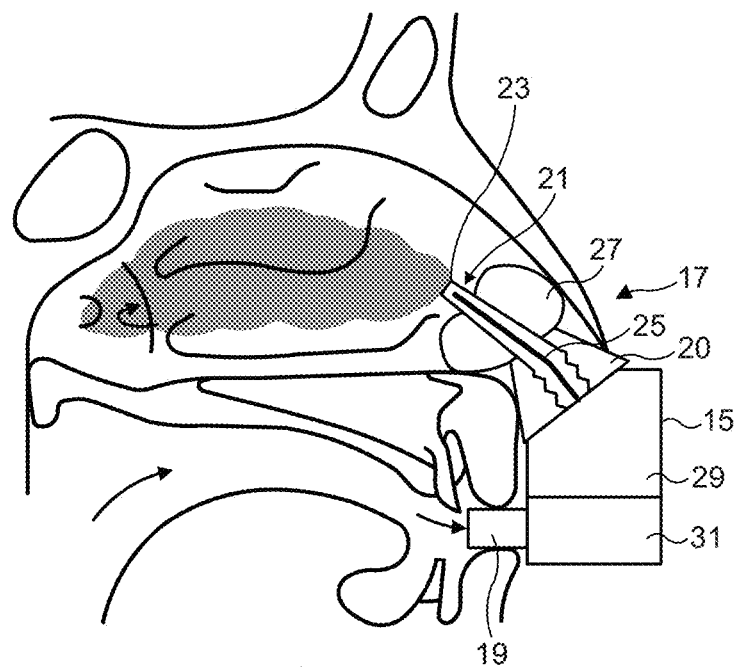
Figure 16:
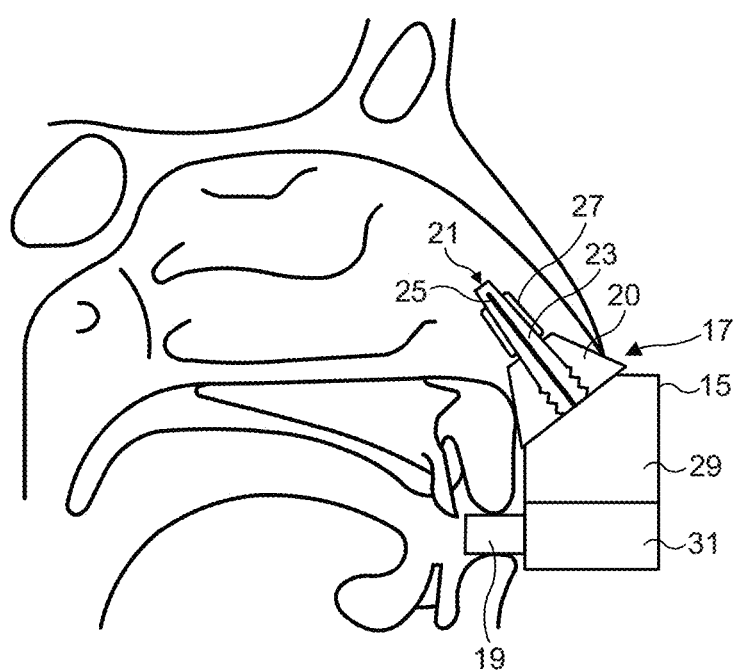
Figure 17:
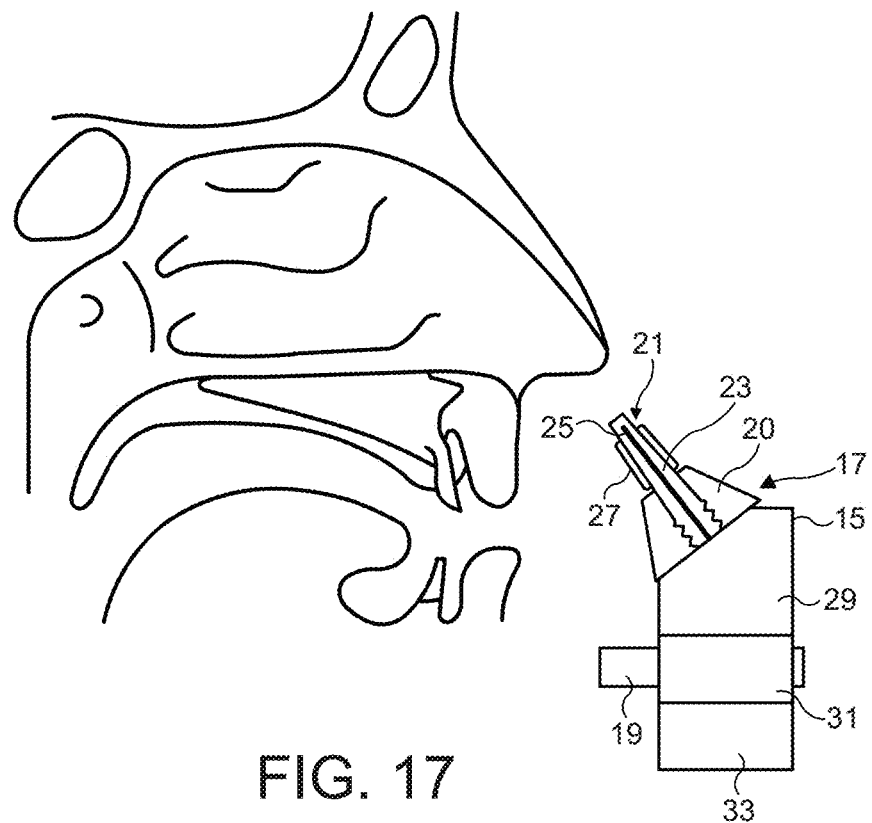
Figure 18:
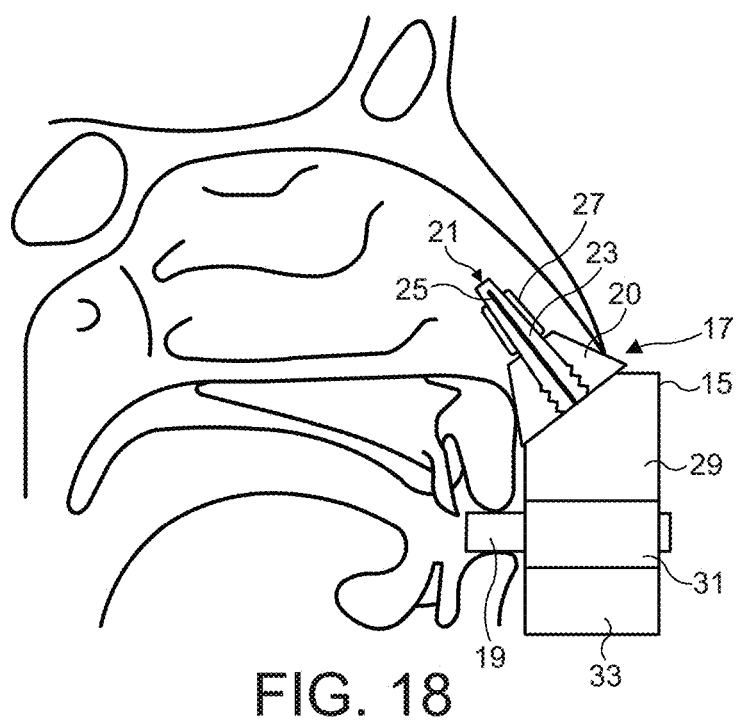
Figure 19:
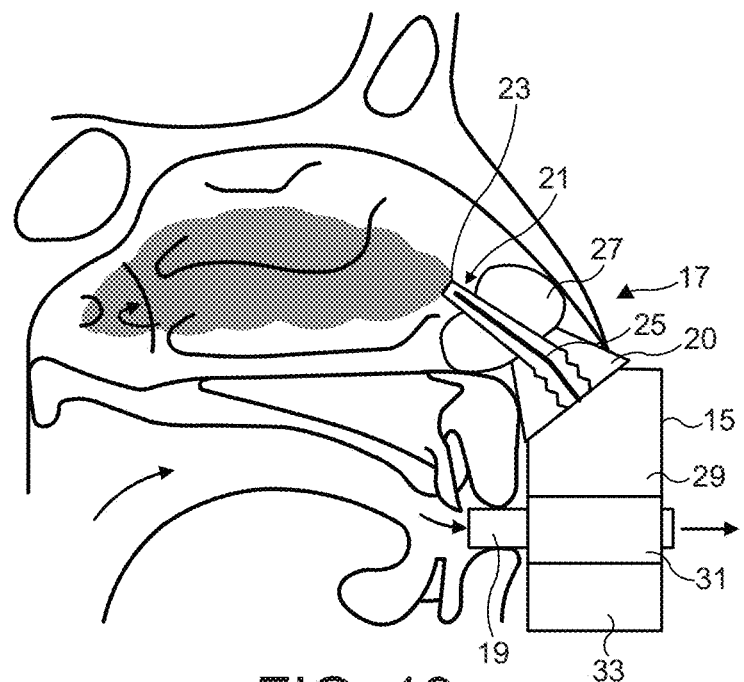
Figure 20:
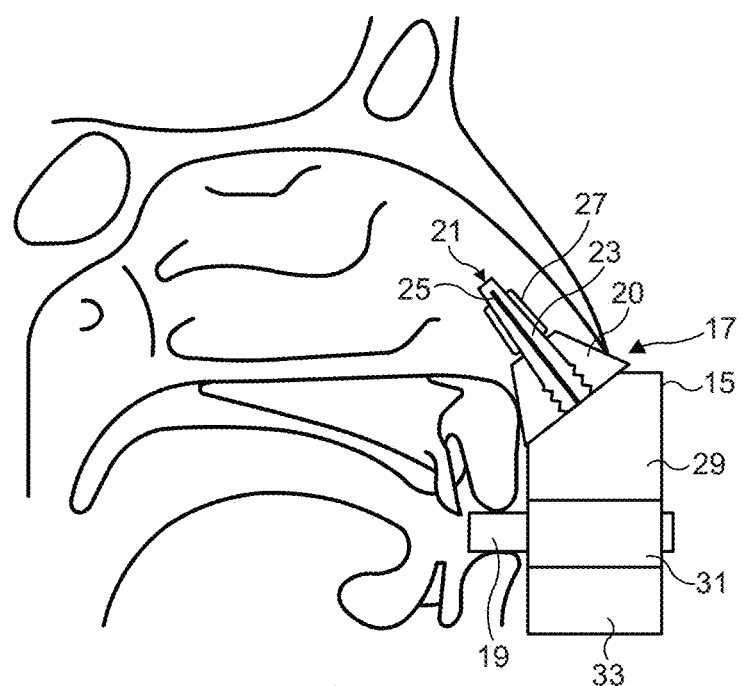
Figure 21:
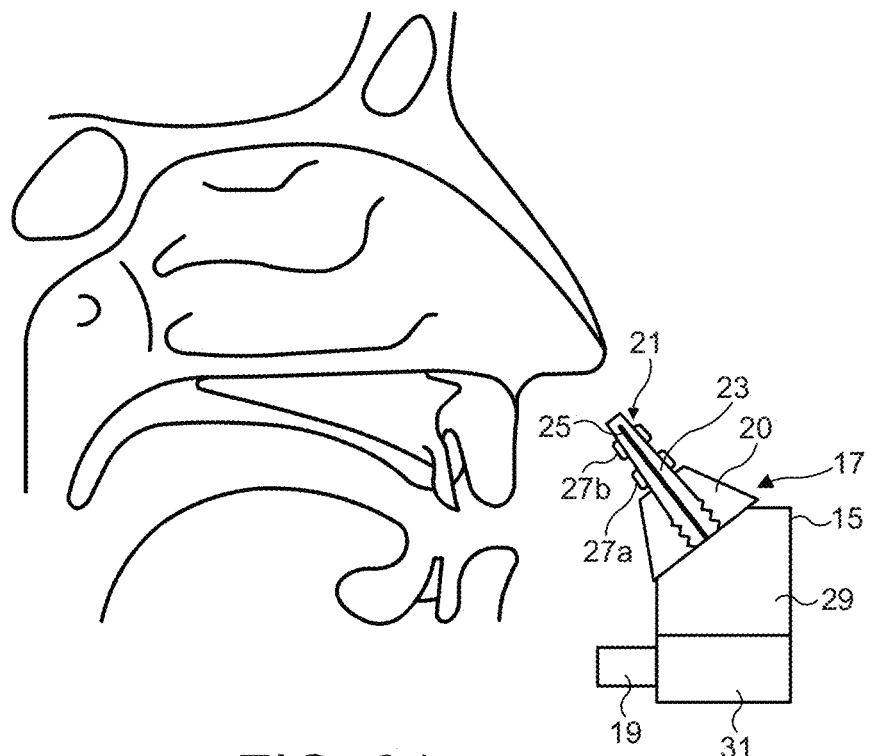
Figure 22:
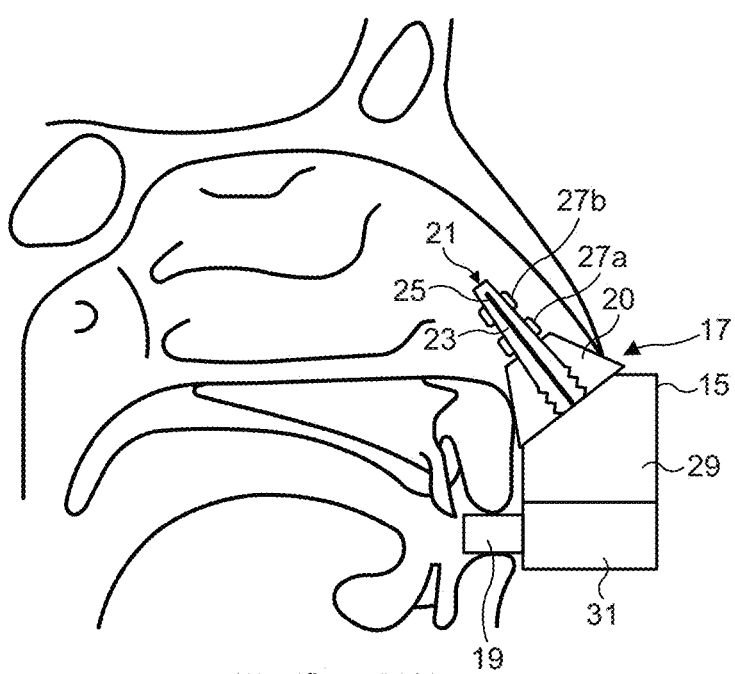
Figure 23:
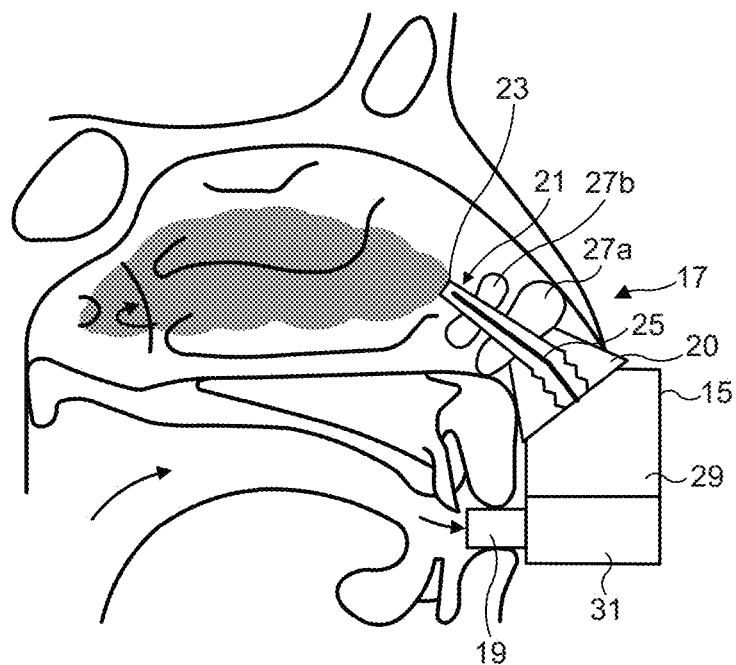
Figure 24:
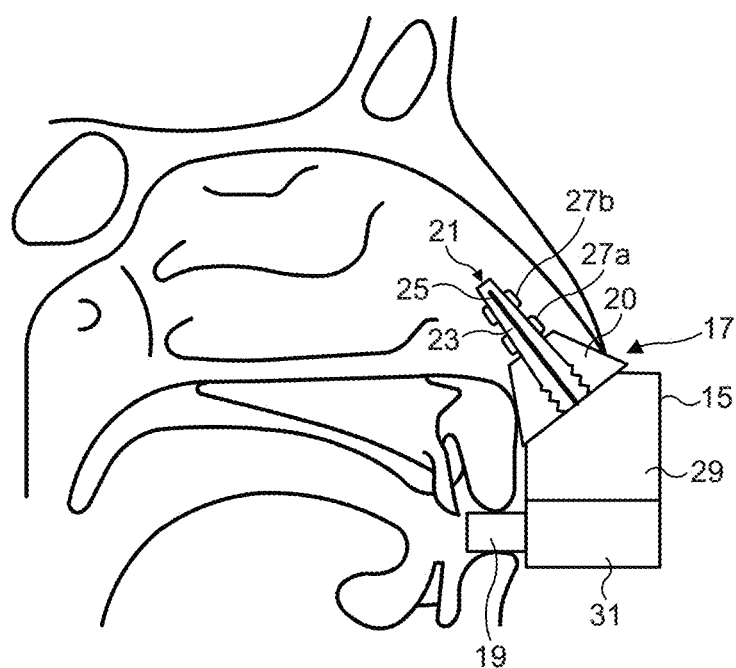
Figure 25:
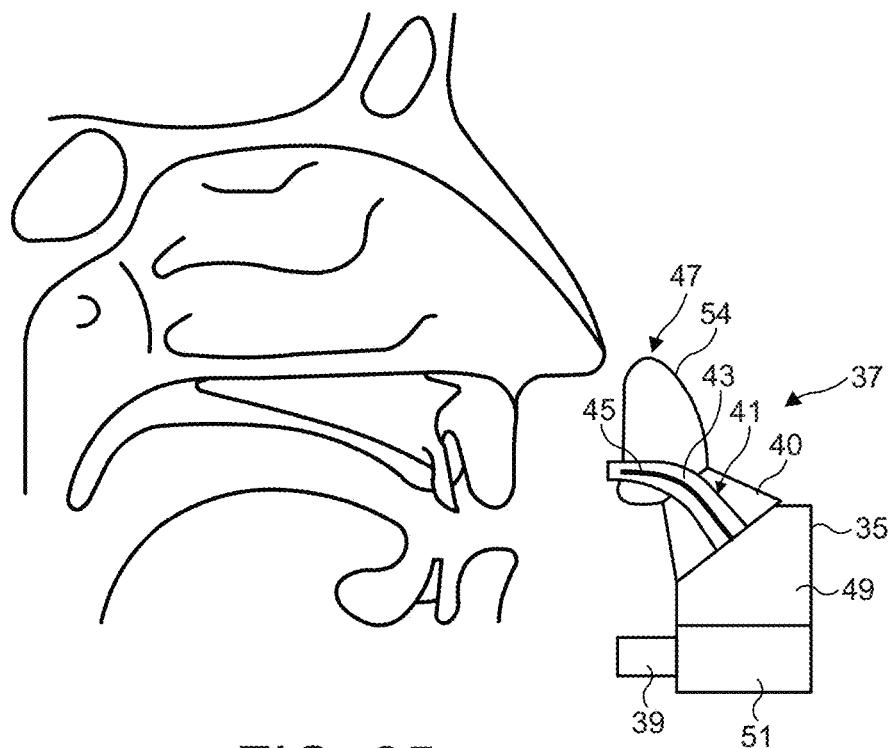
Figure 26:
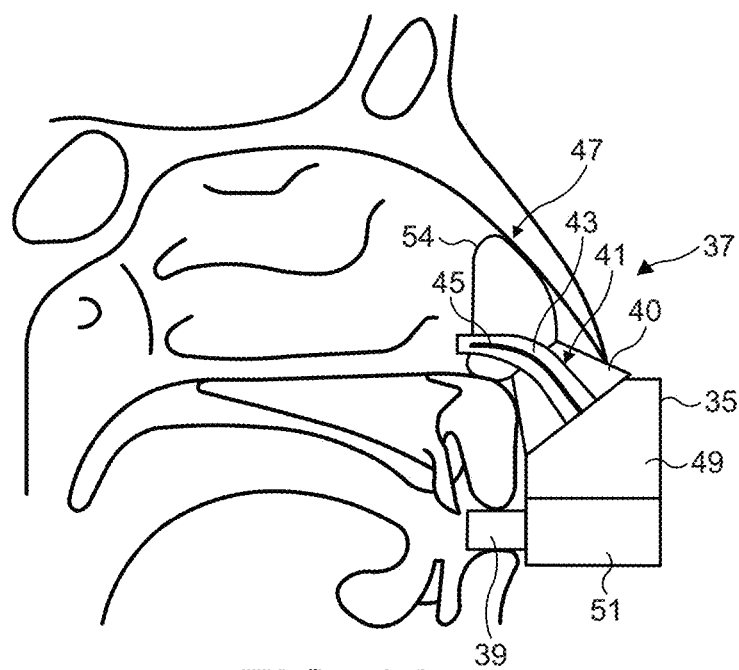
Figure 27:
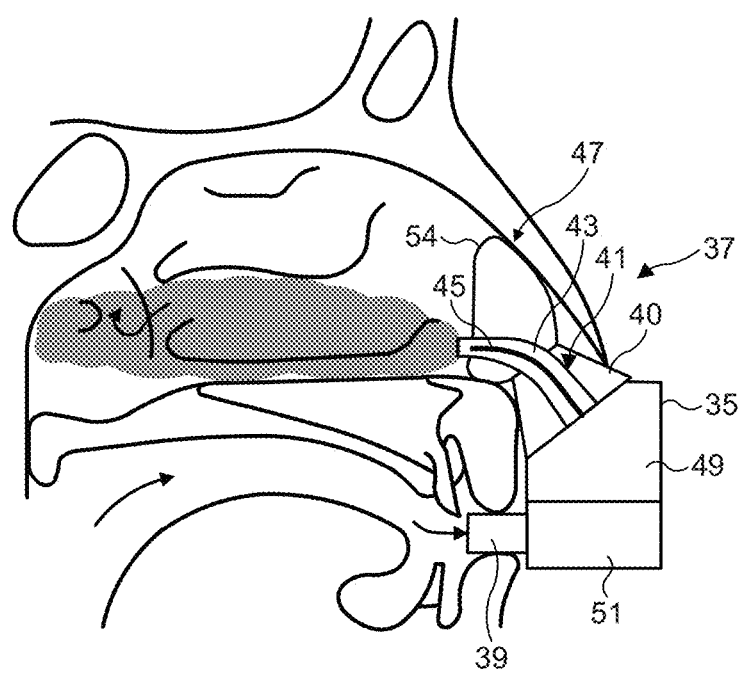
Figure 28:
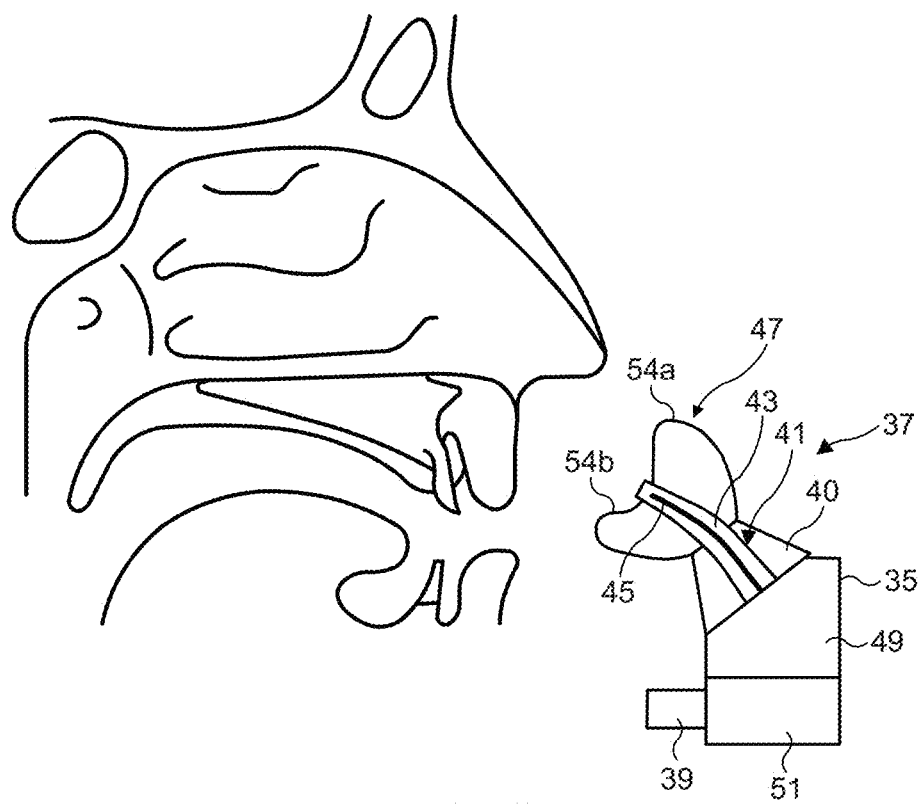
Figure 29:
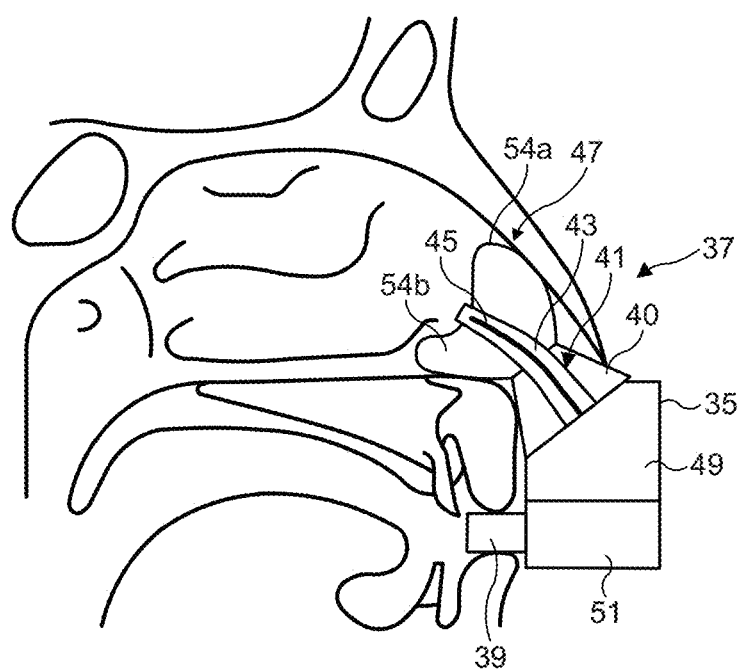
Figure 30:
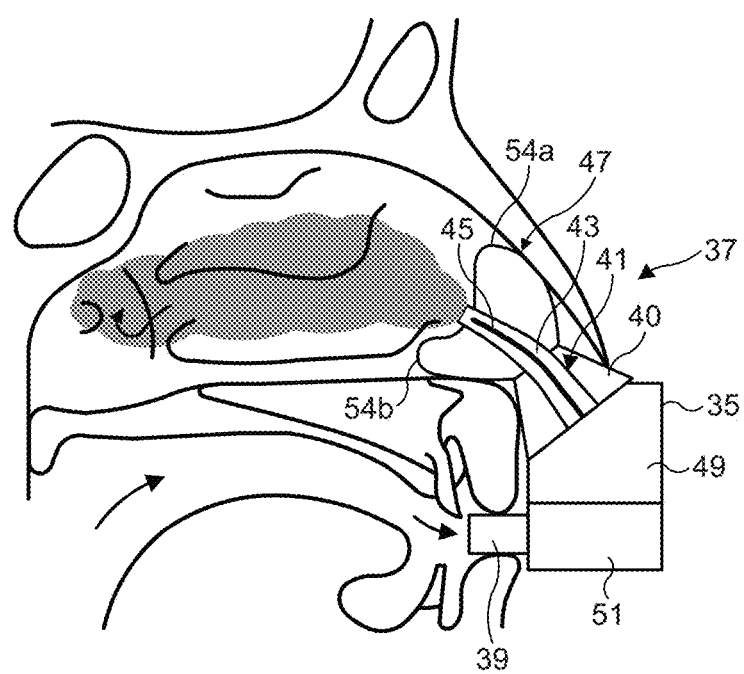
Figure 31:
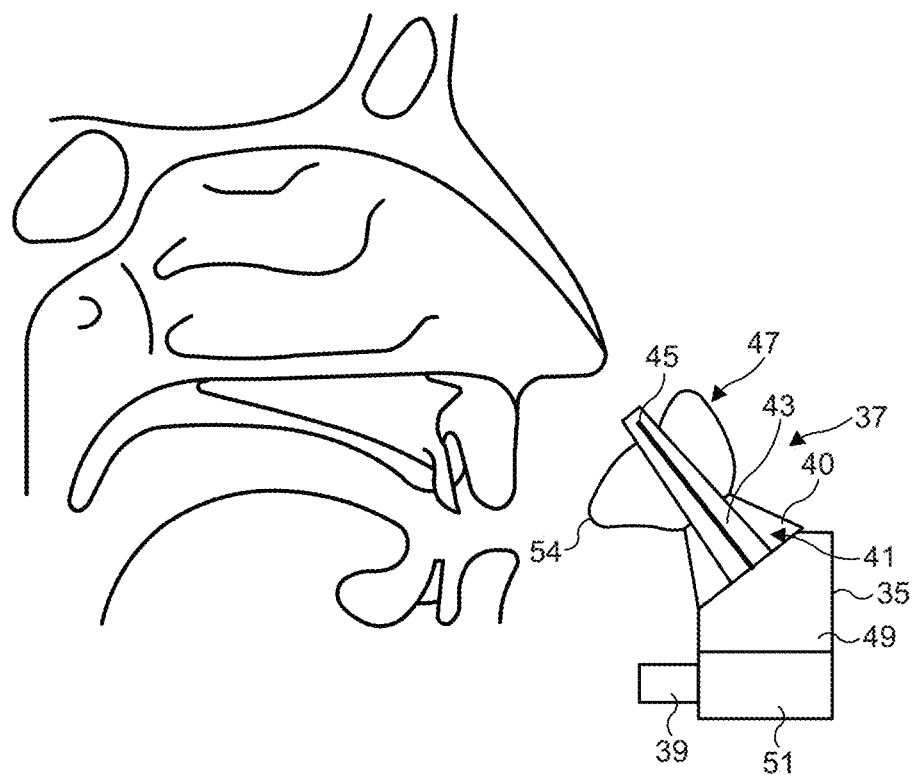
Figure 32:
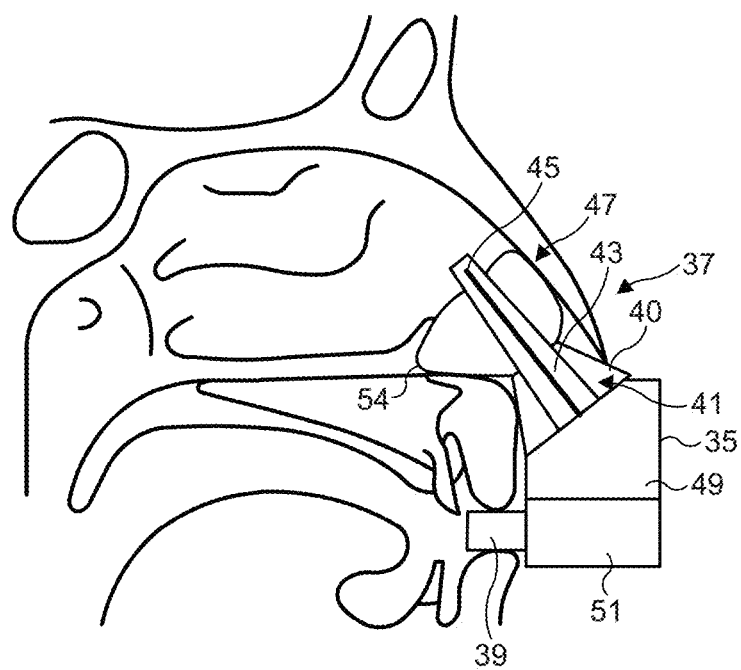
Figure 33:
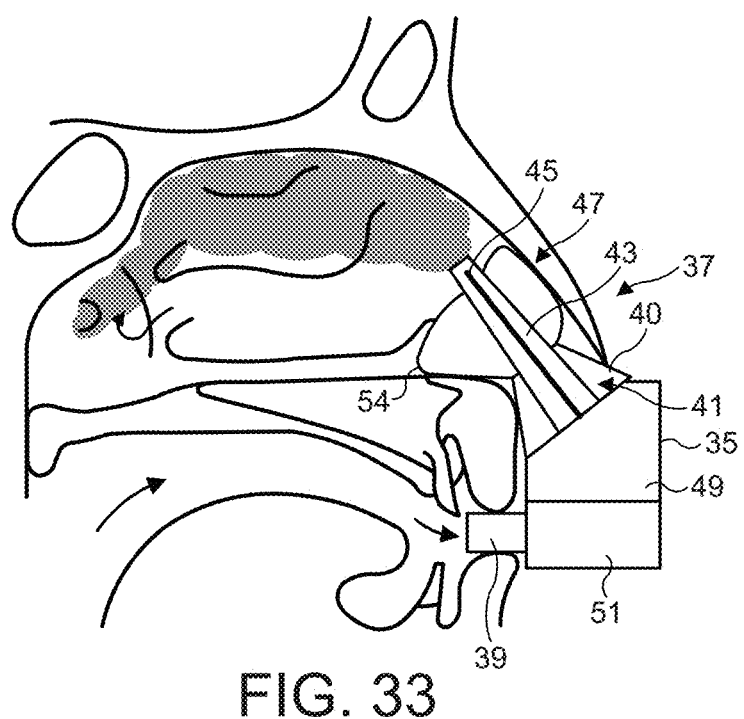
Figure 34:
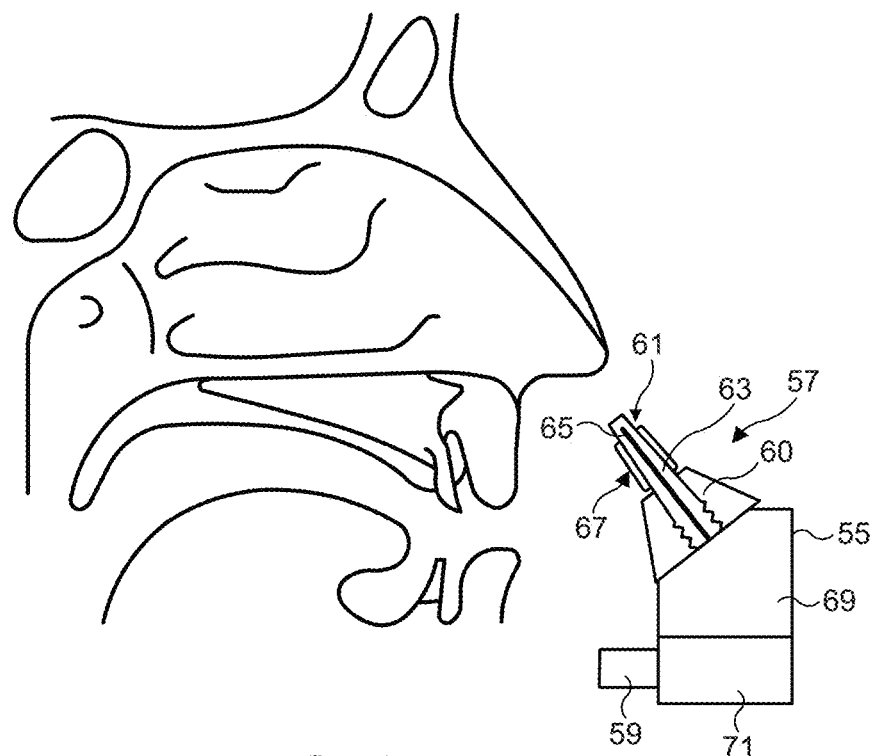
Figure 35:
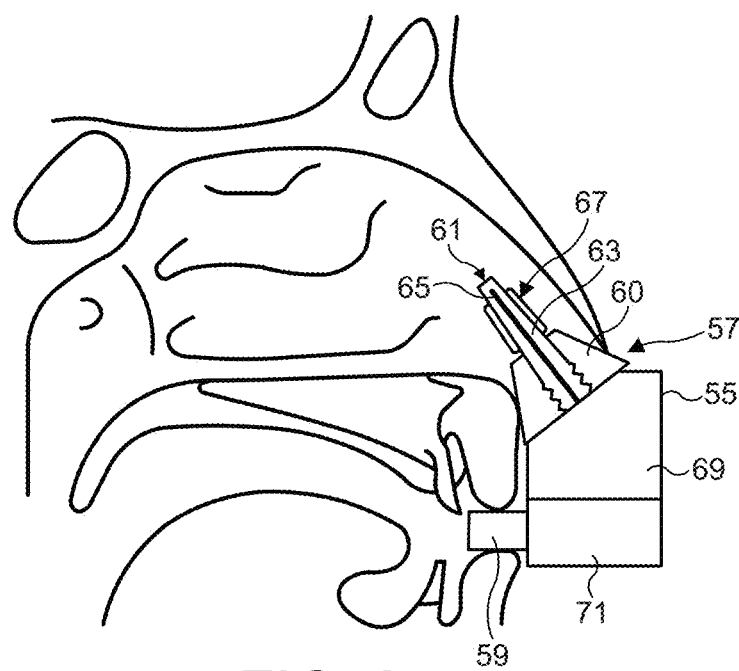
Figure 36:
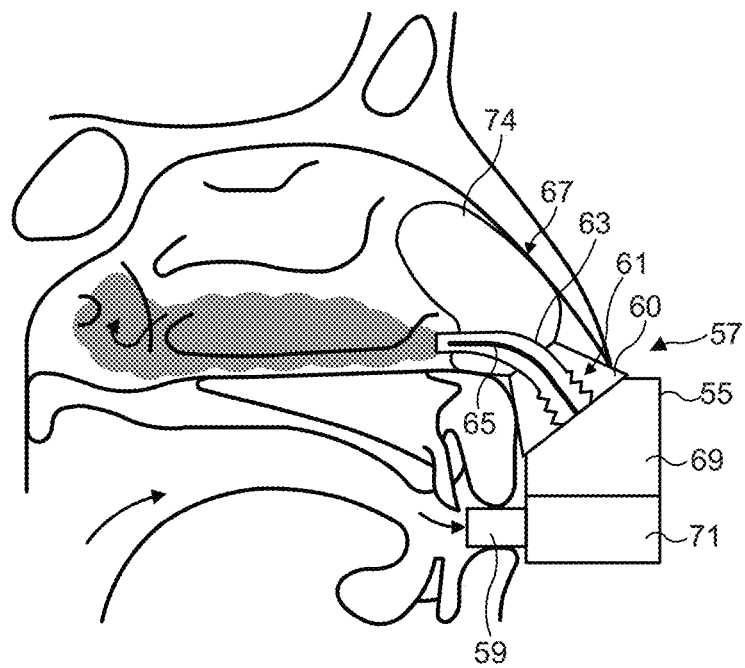
Figure 37:
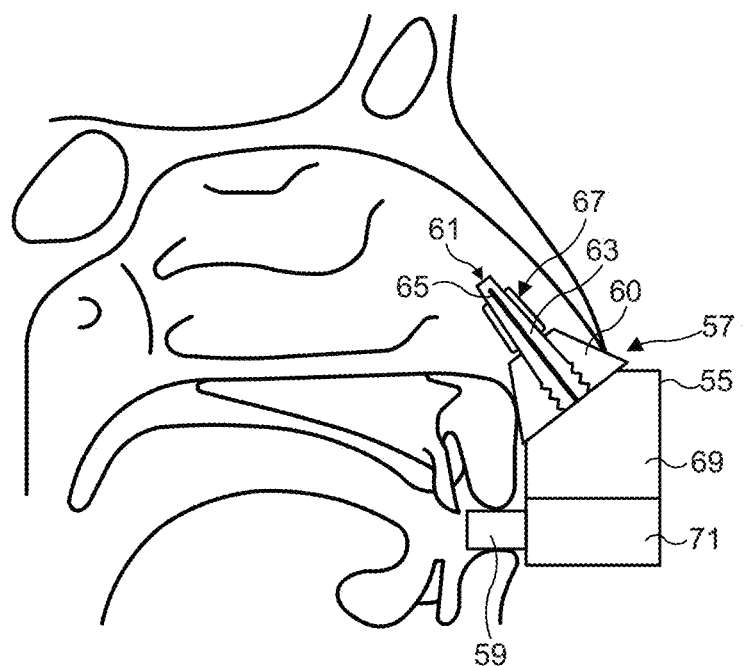
Figure 38:
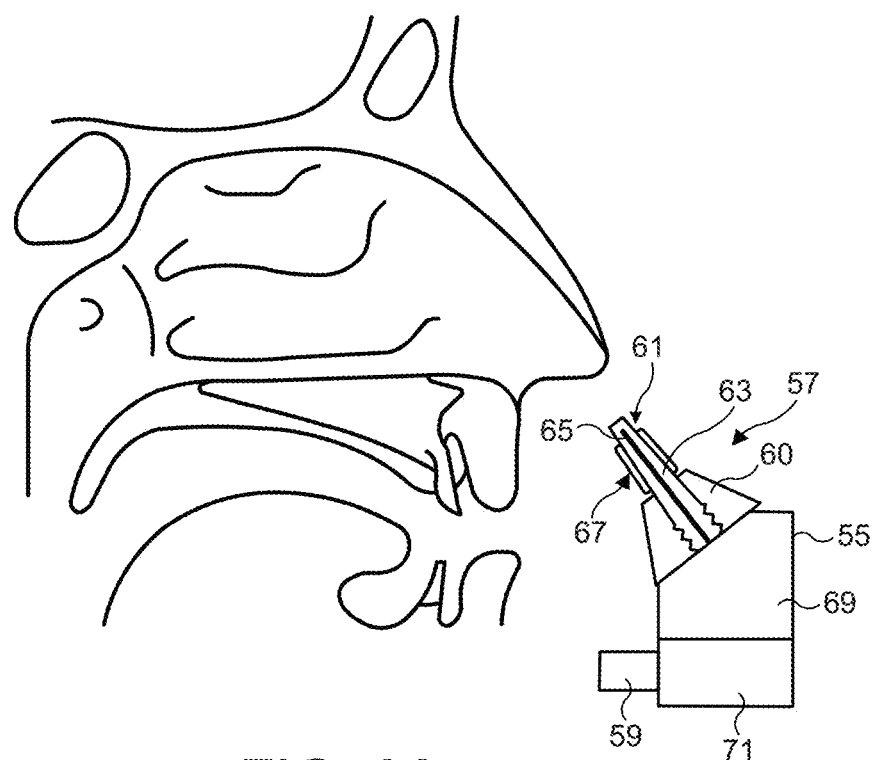
Figure 39:
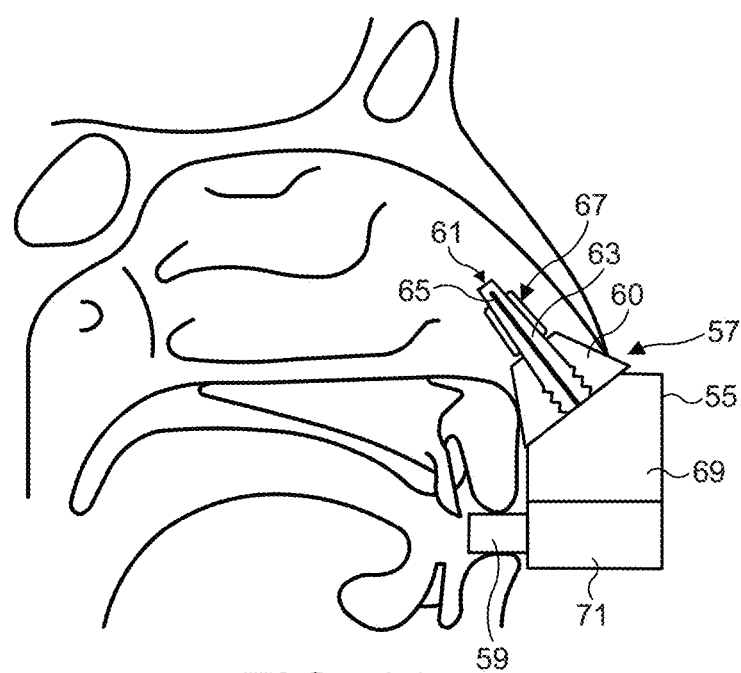
Figure 40:
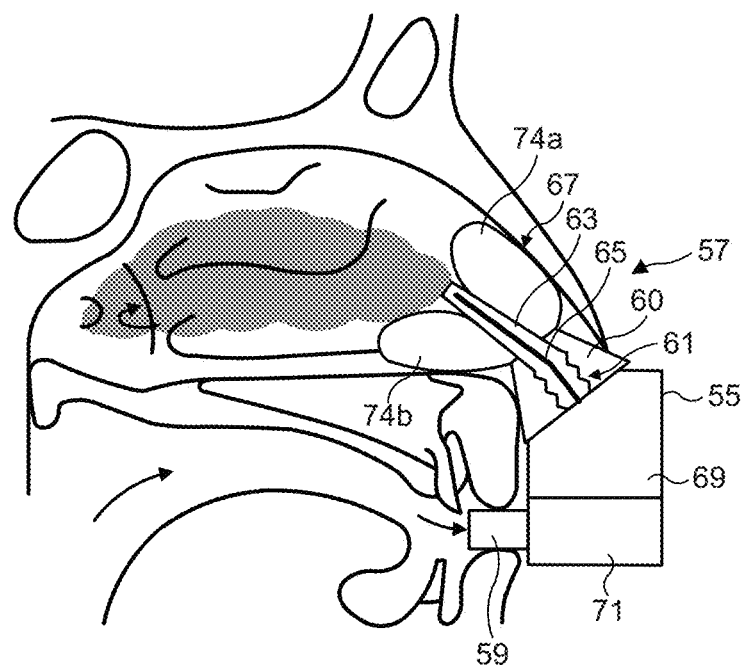
Figure 41:
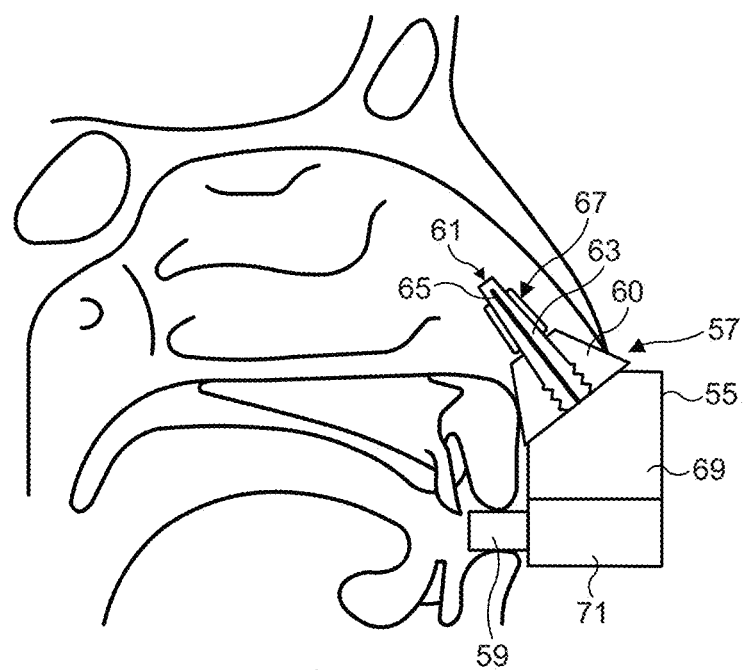
Figure 42:
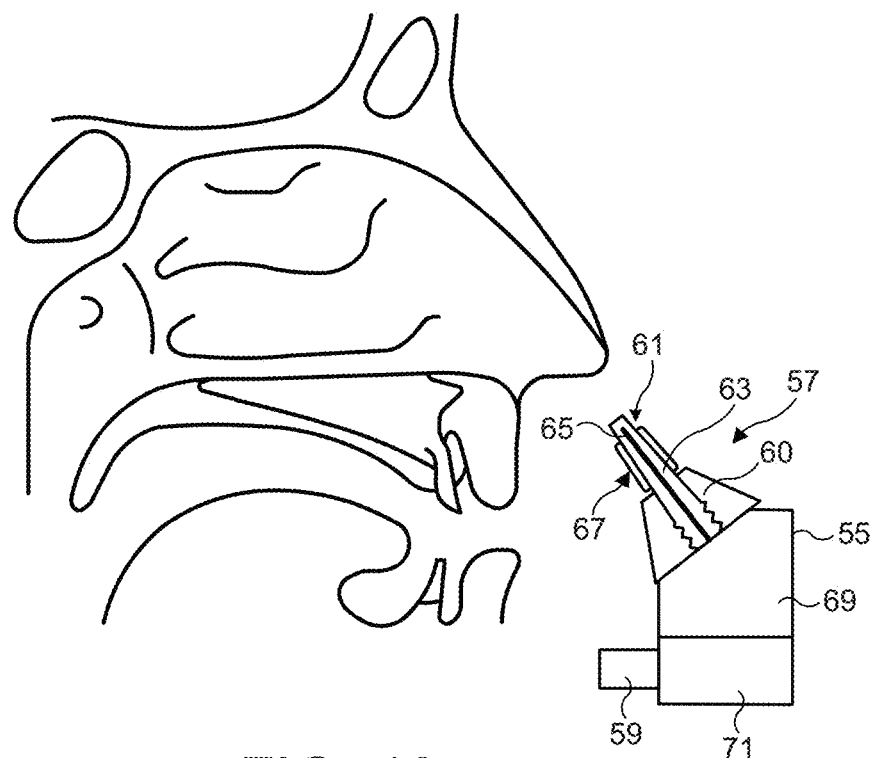
Figure 43:
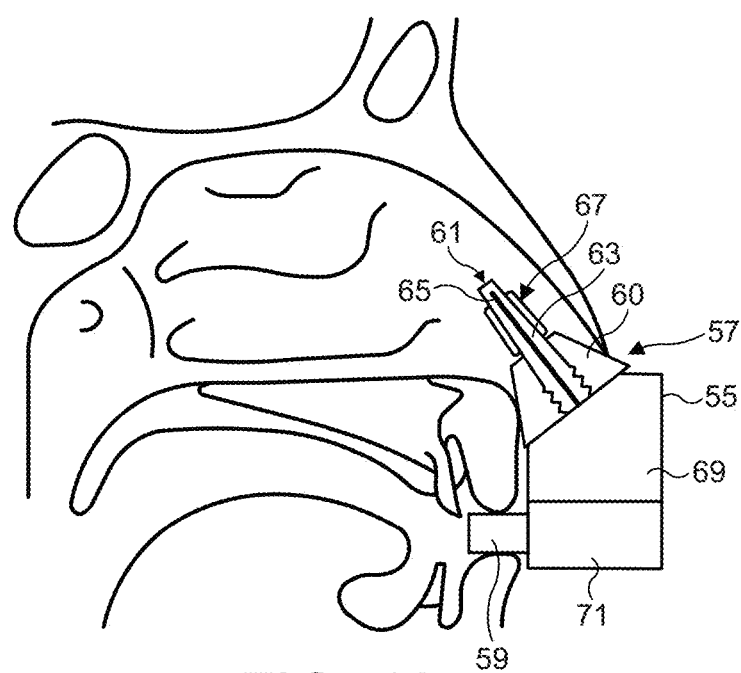
Figure 44:
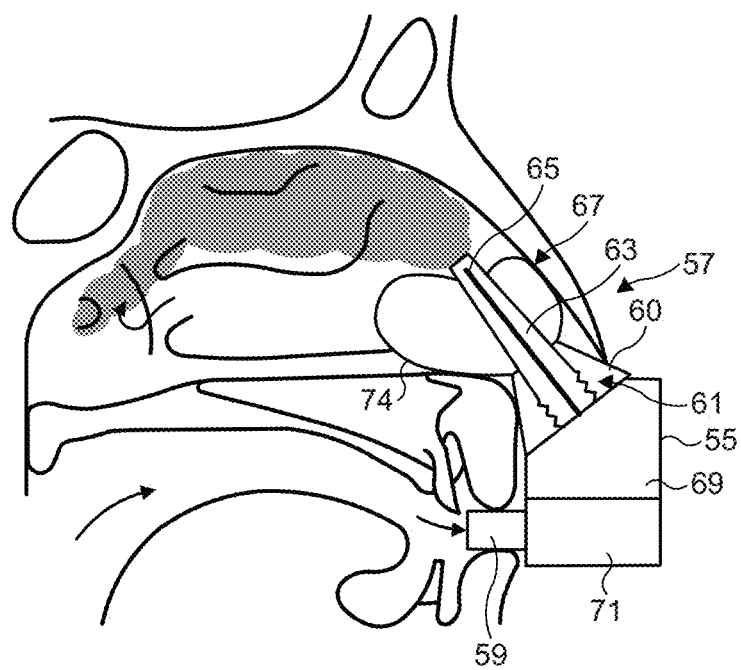
Figure 45:
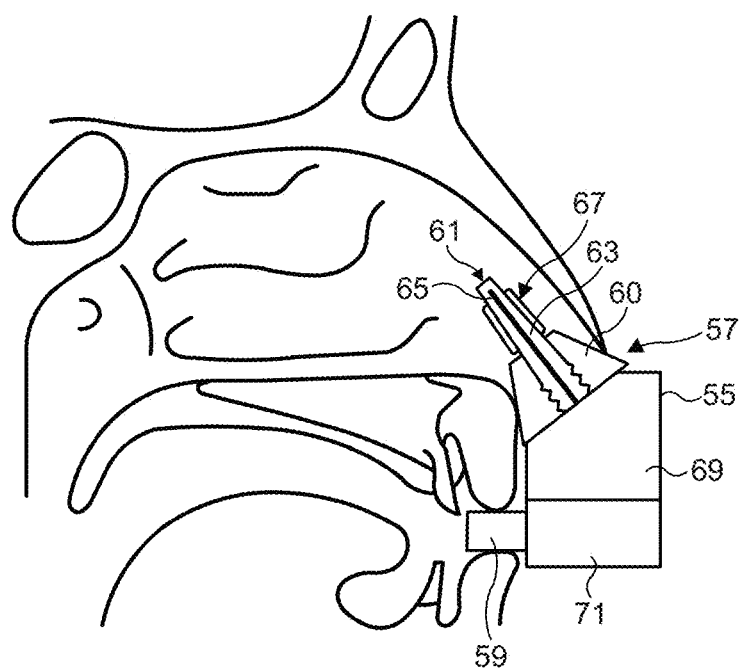
Figure 47:
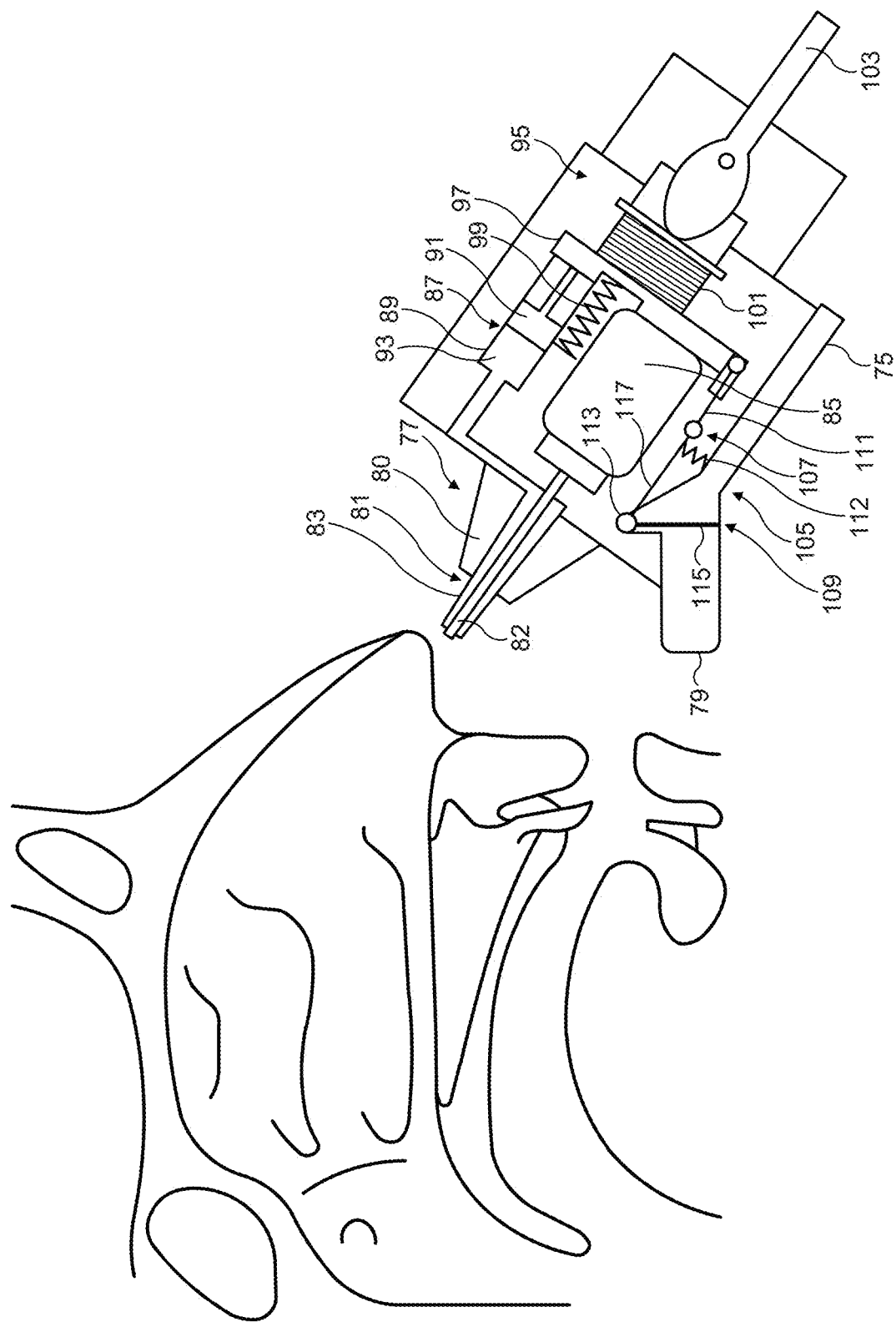
Figure 48:
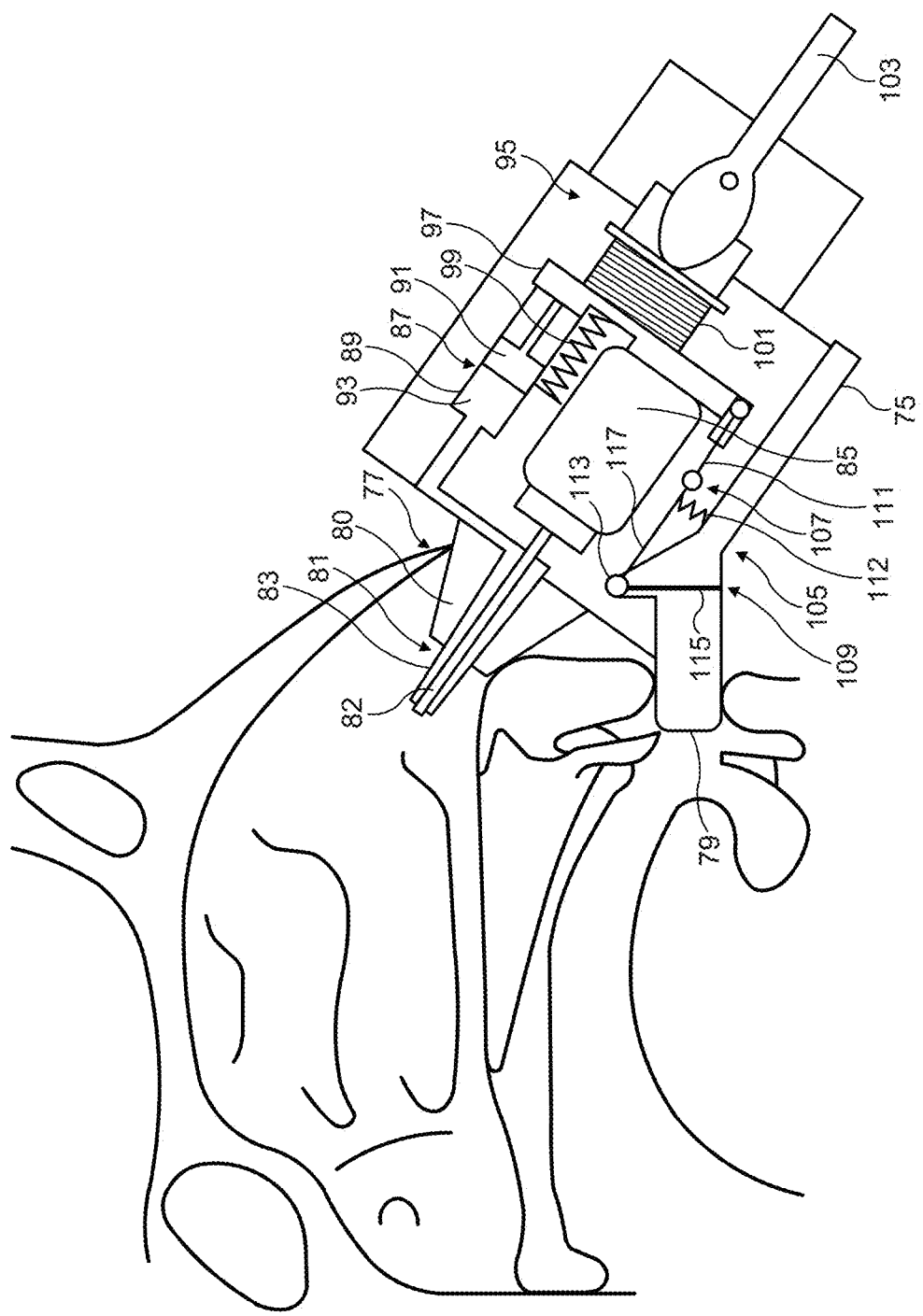
Figure 49:
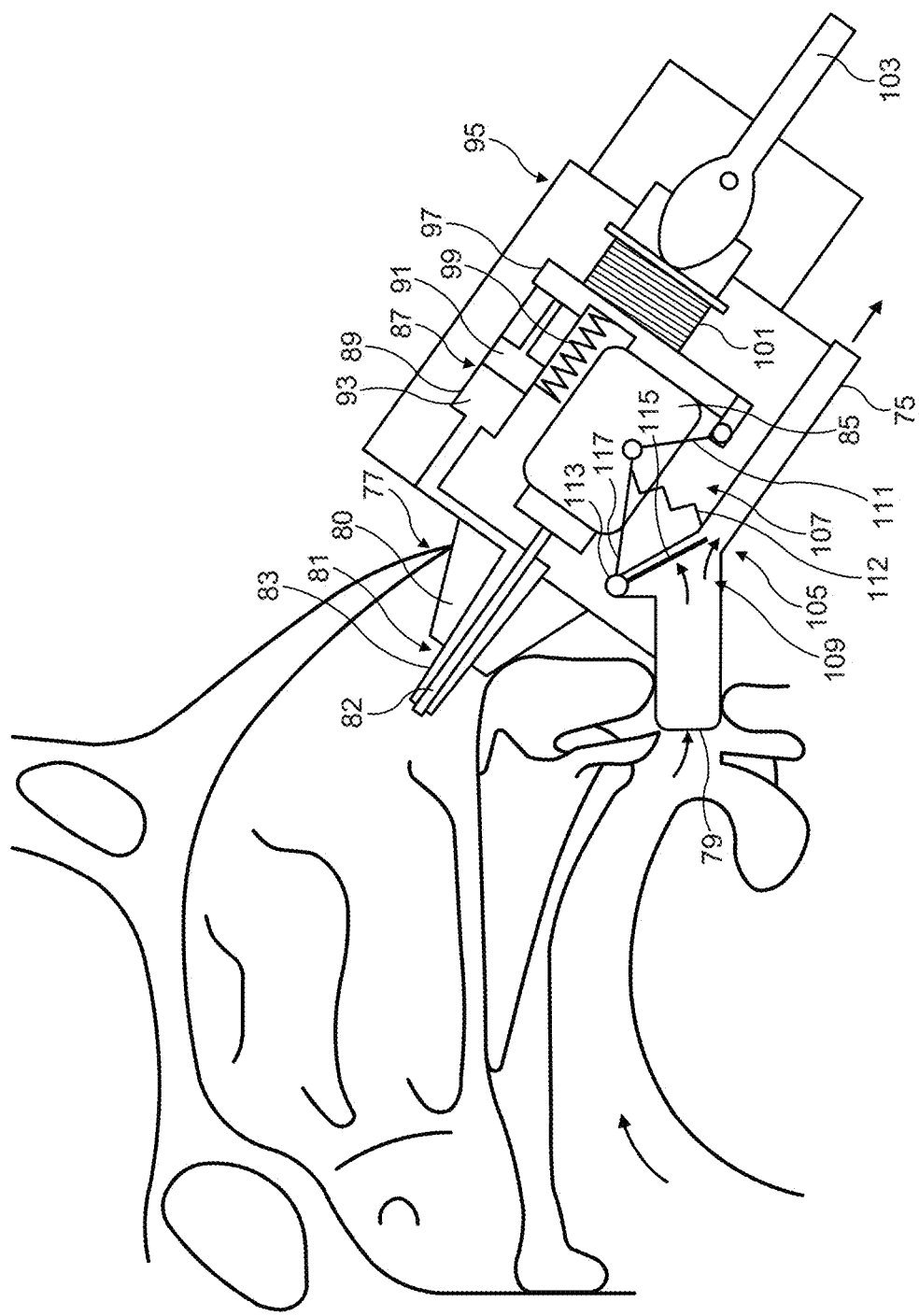
Figure 50:
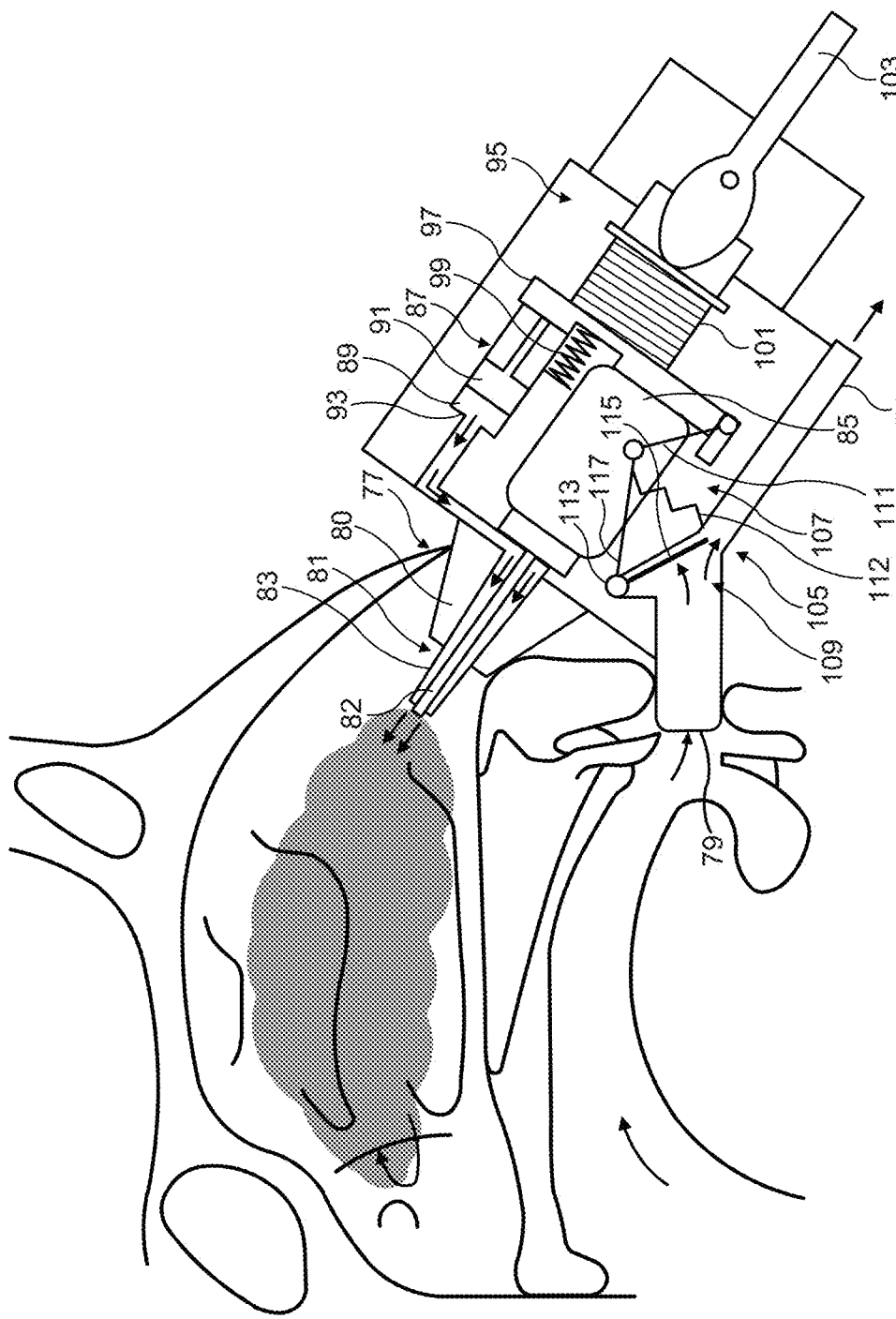
Figure 51:
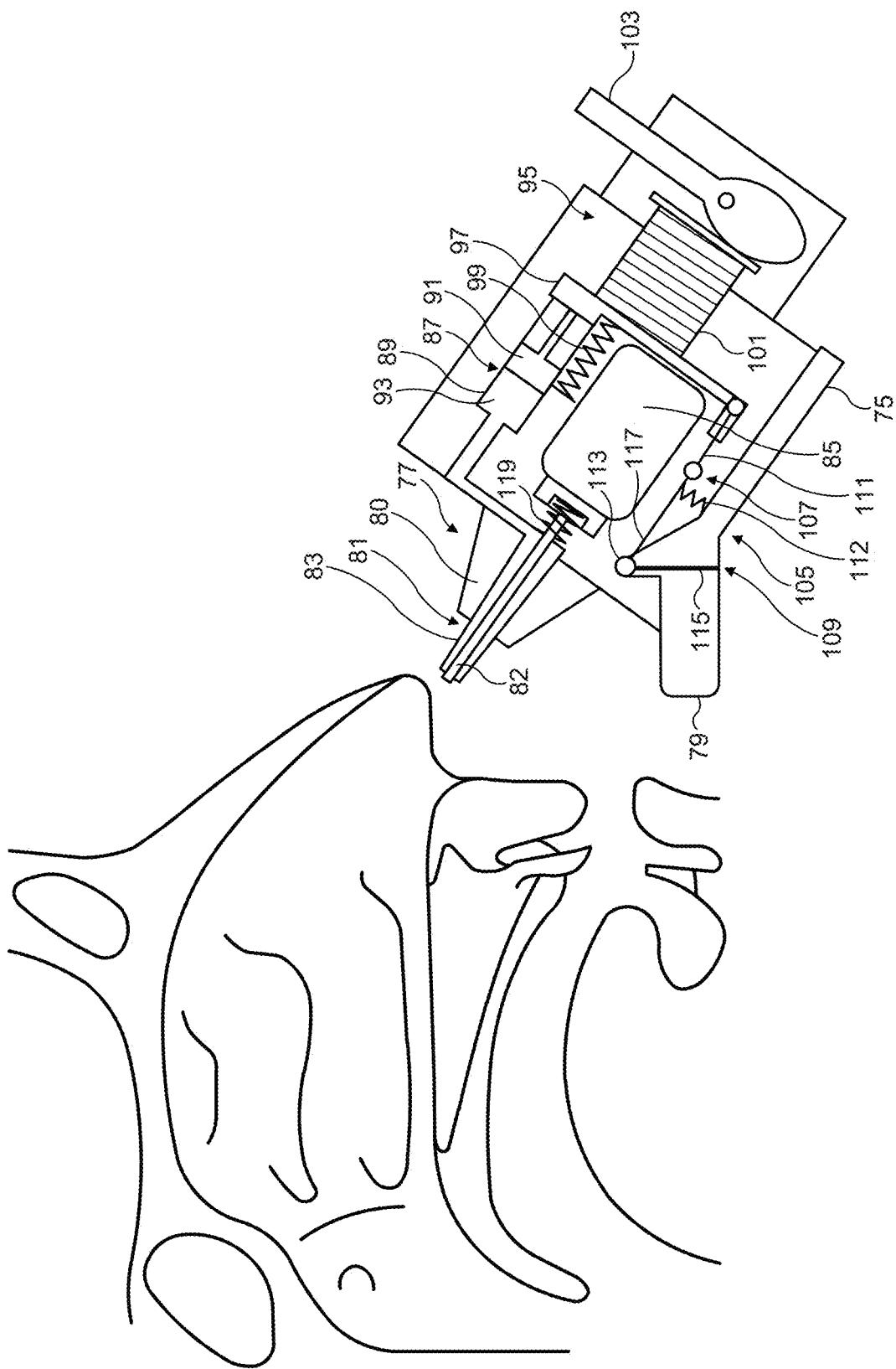
Figure 52:
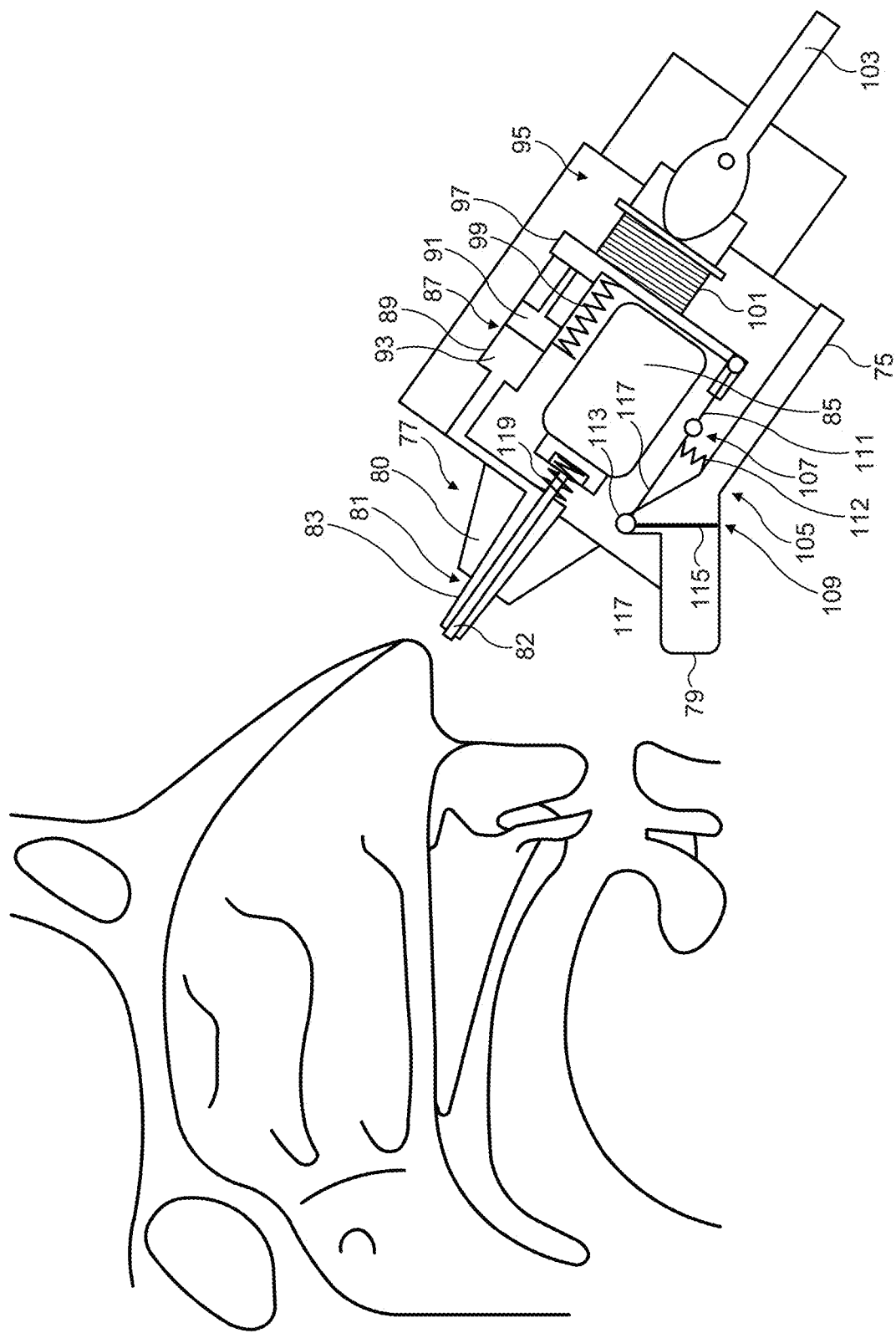
Figure 53:
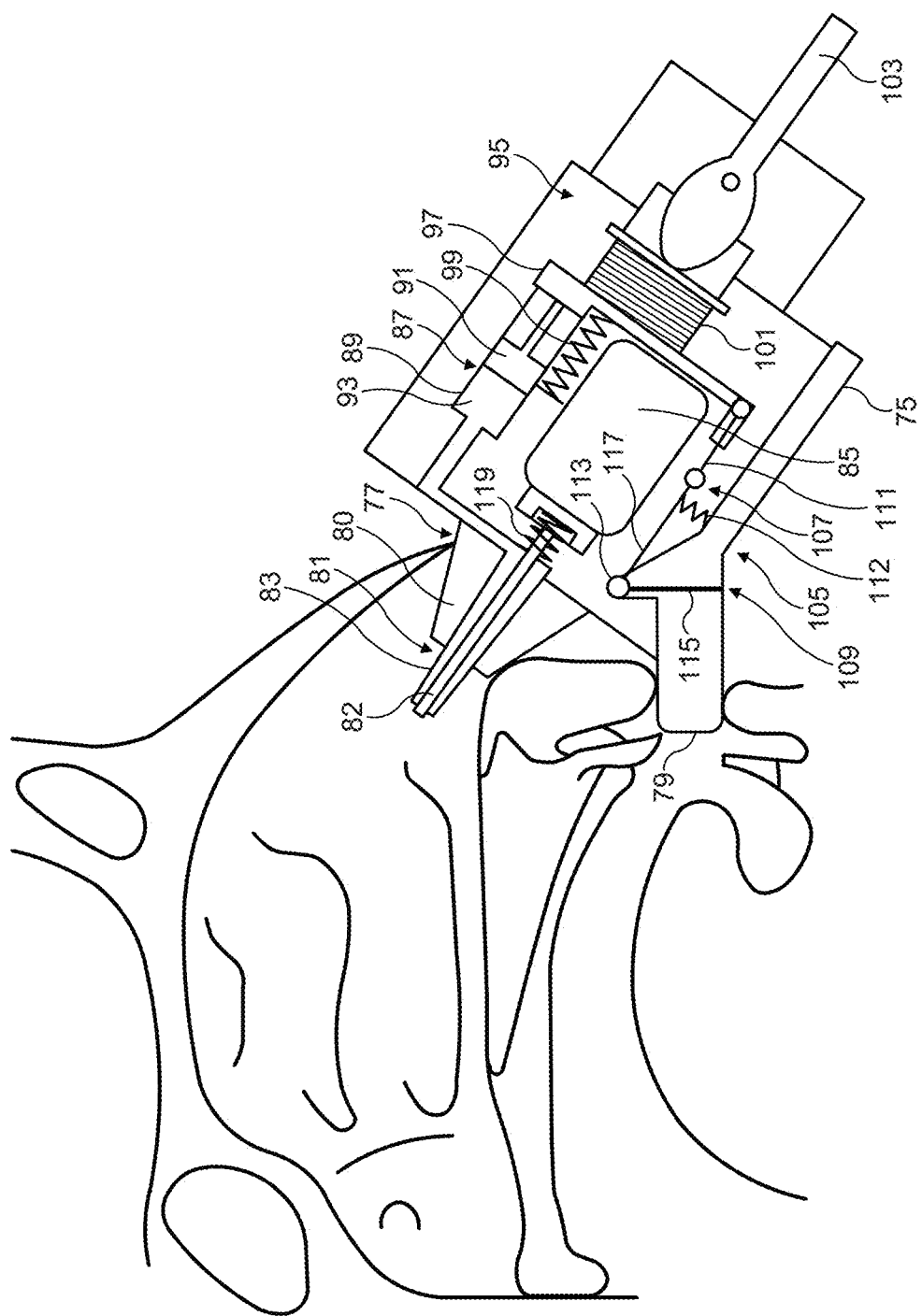
Figure 54:
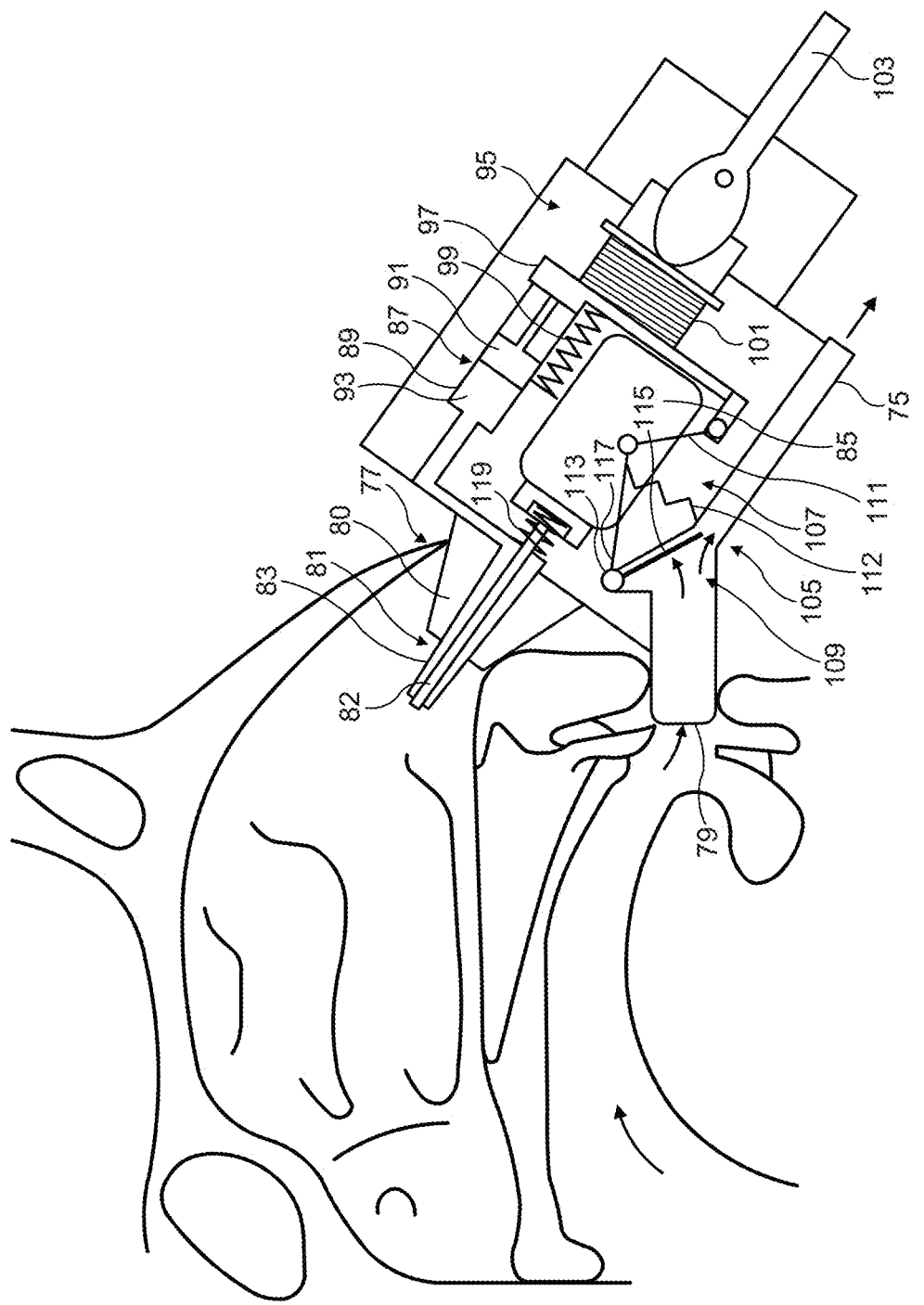
Figure 55:
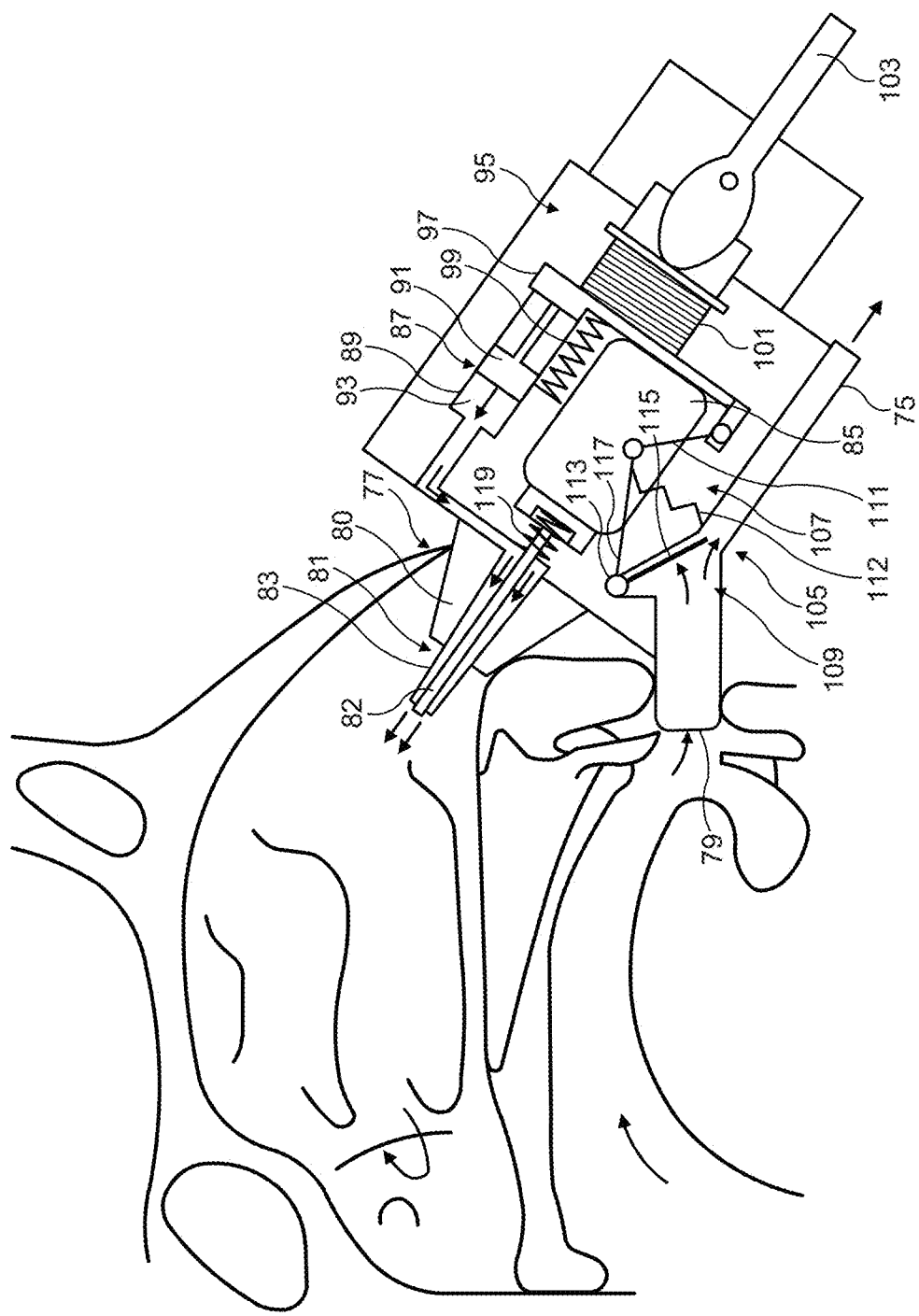
Figure 56:
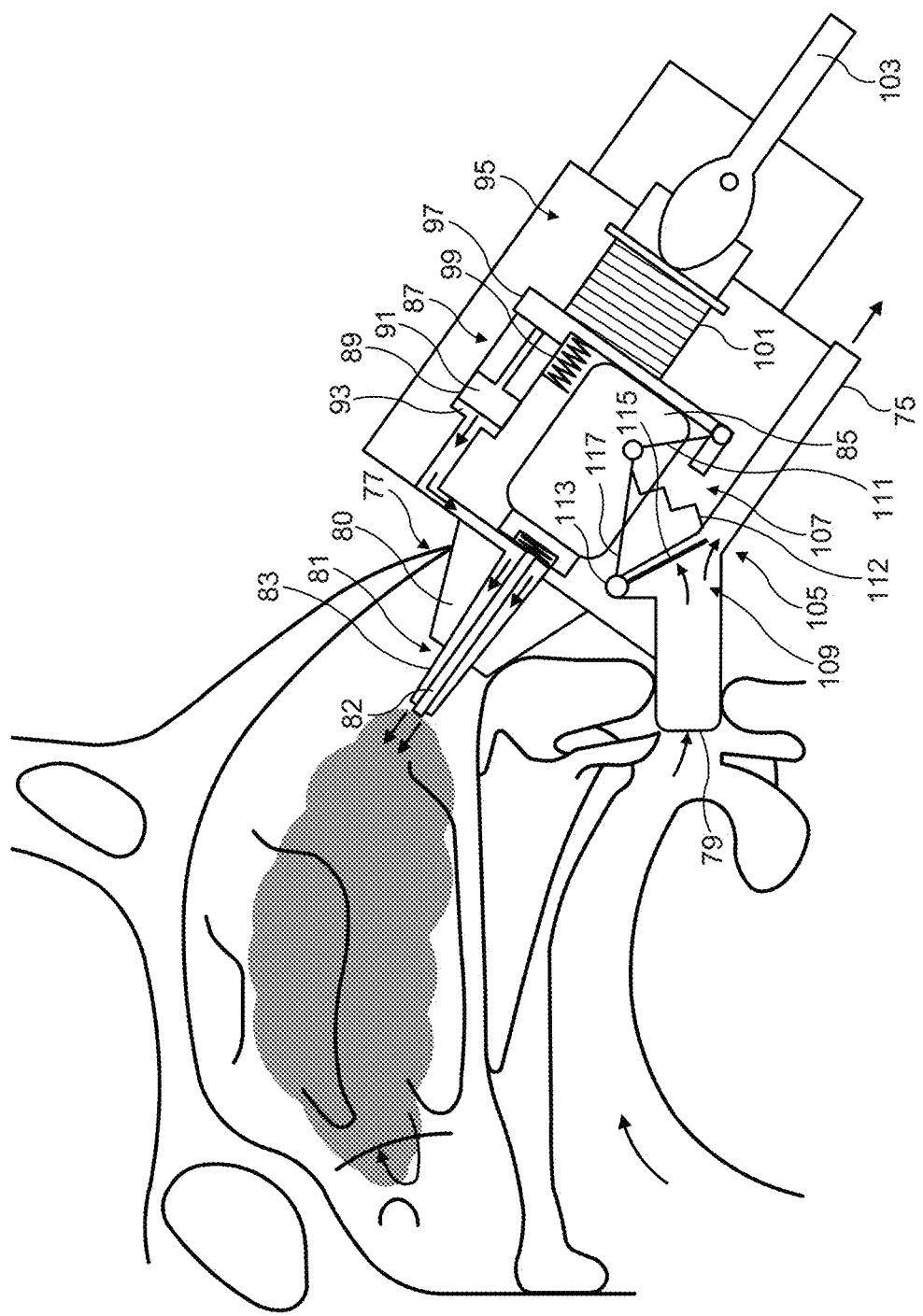
Figure 57:
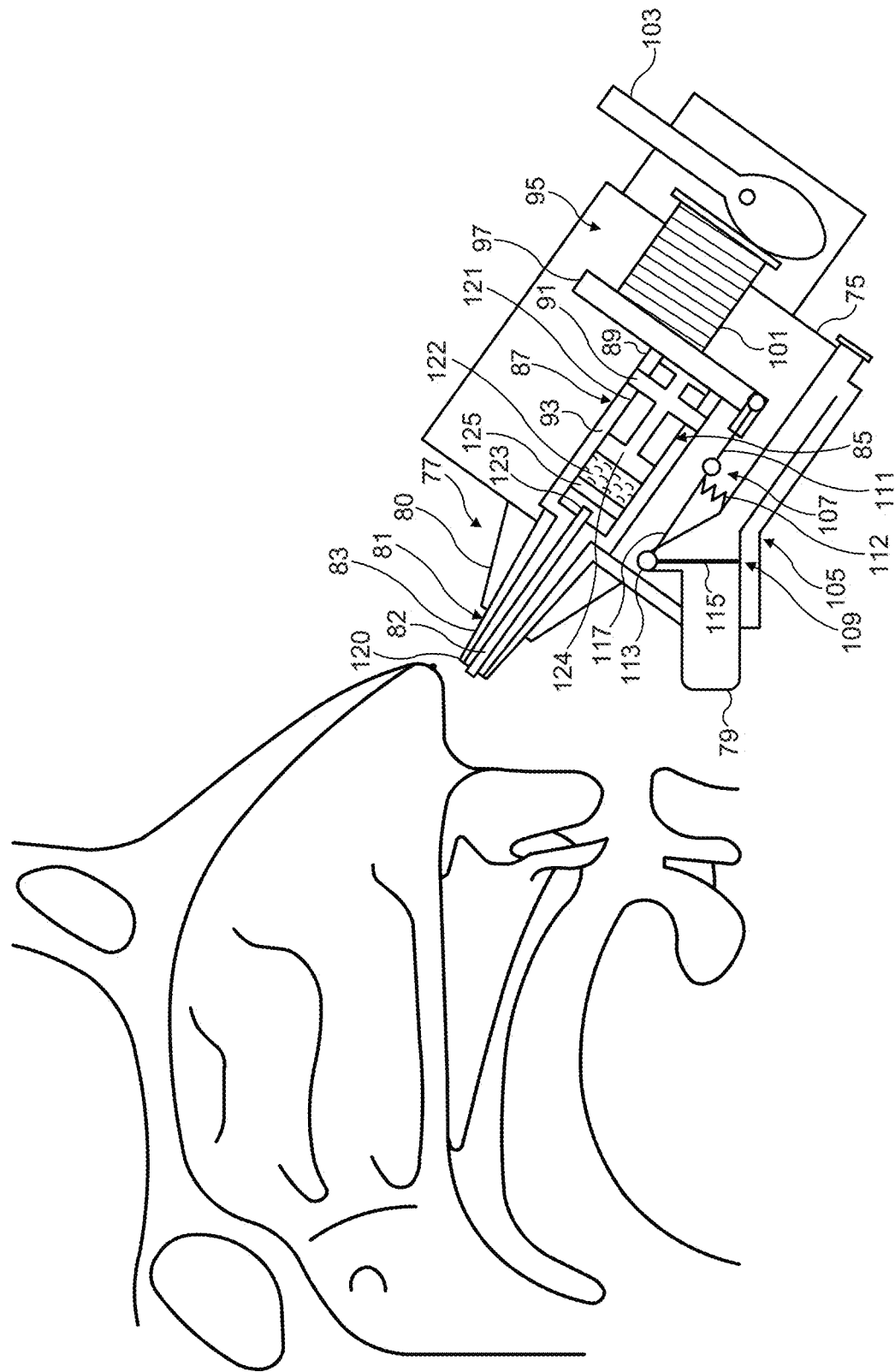
Figure 58:
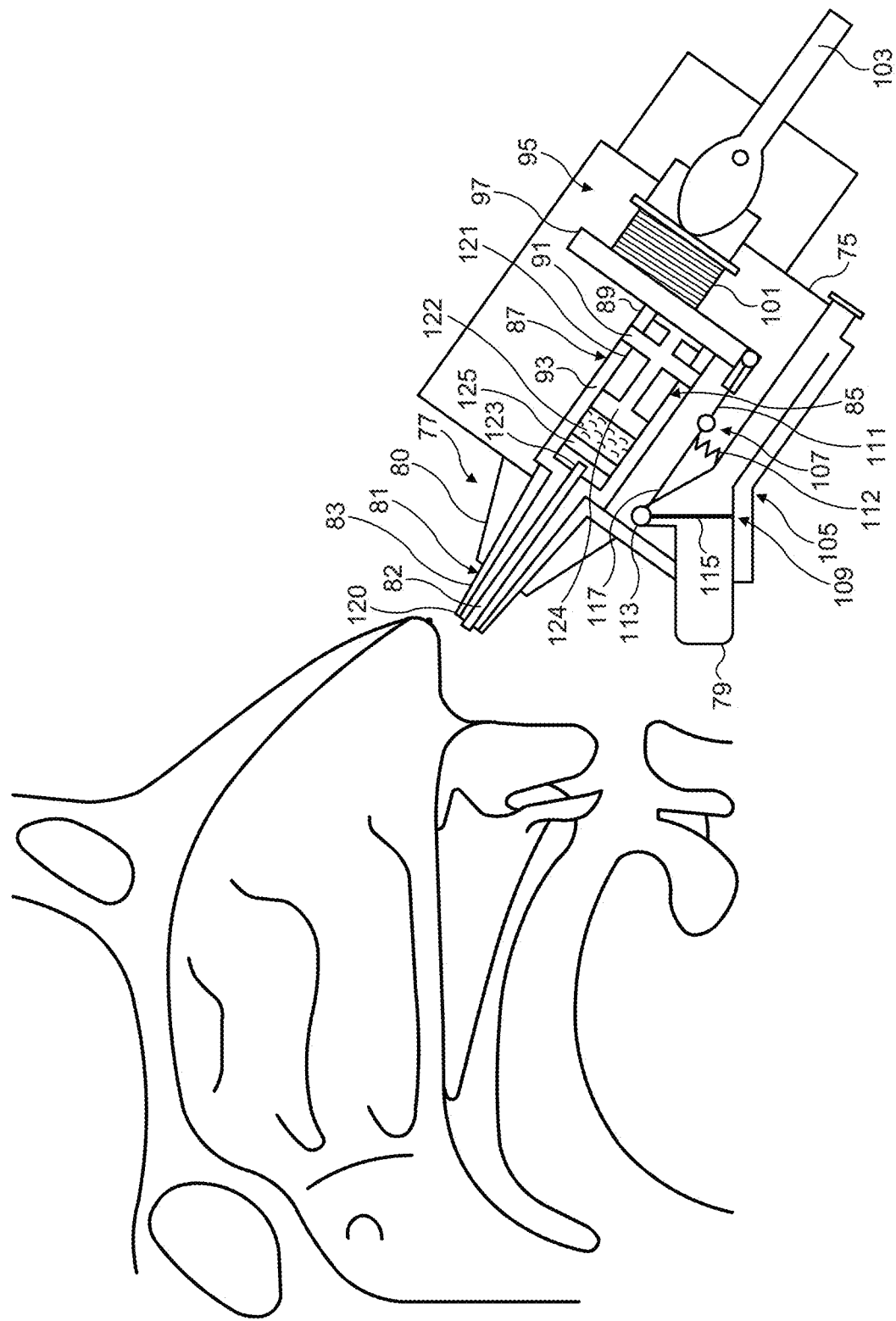
Figure 59:
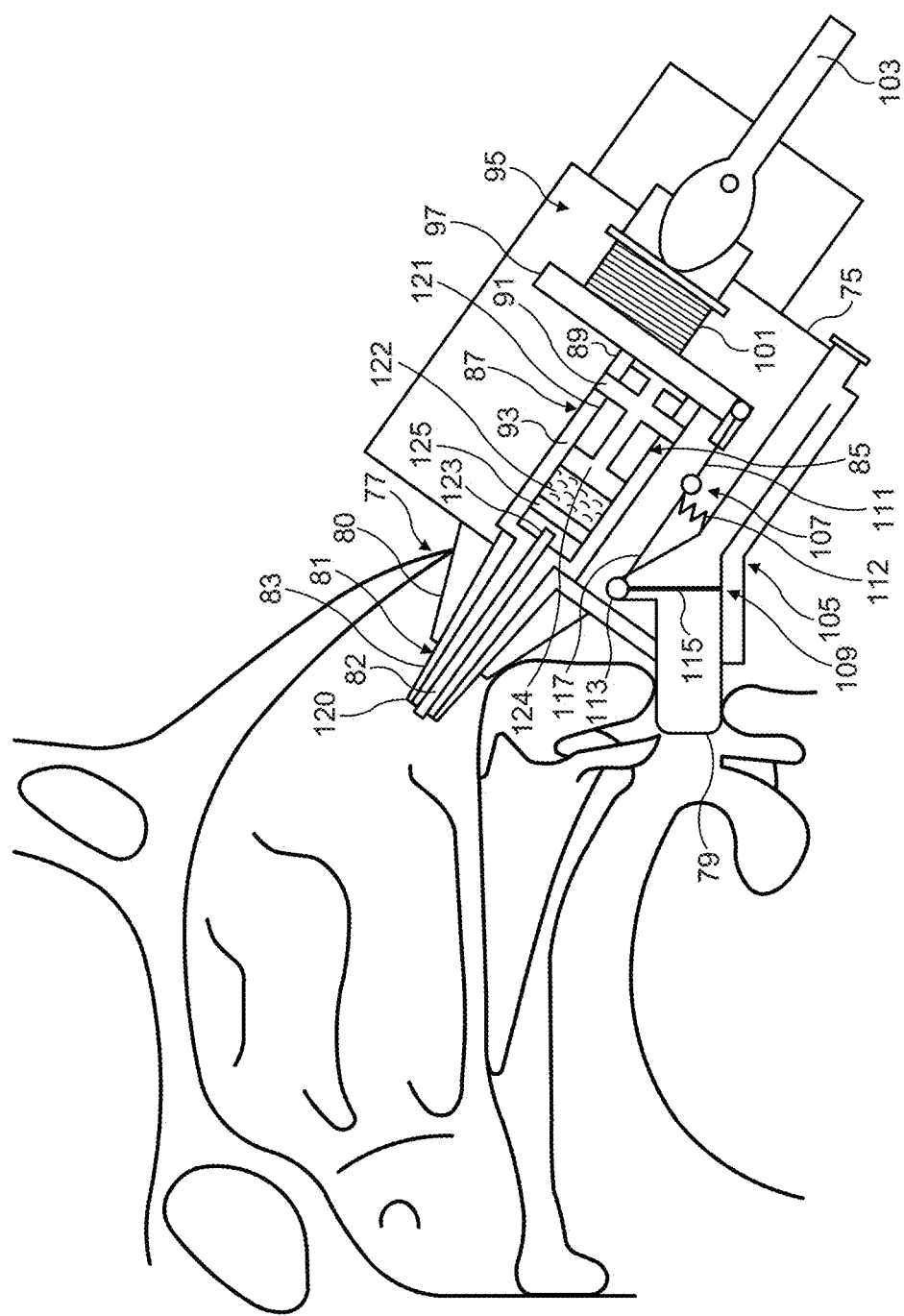
Figure 60:
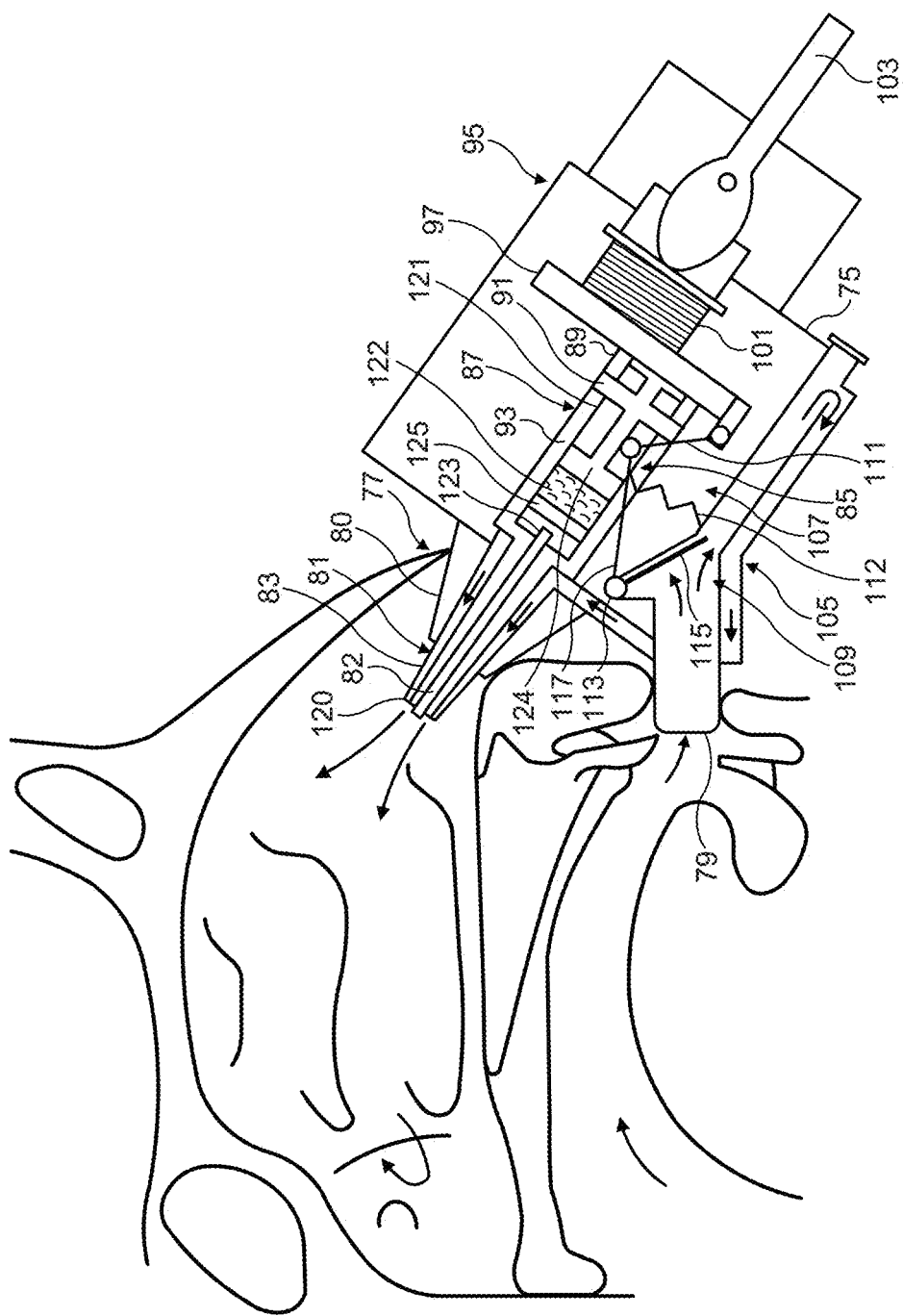
Figure 61:
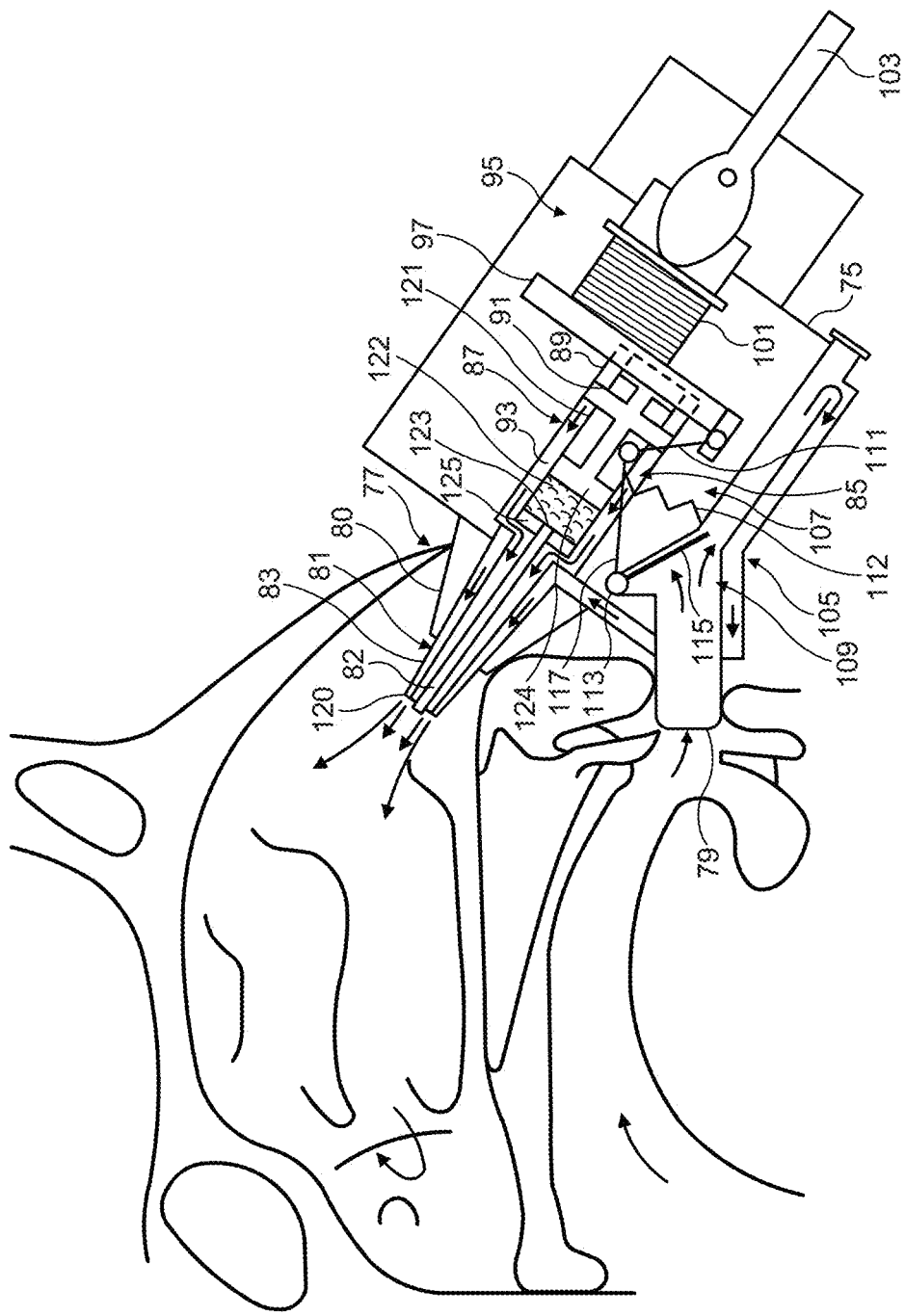
Figure 62:
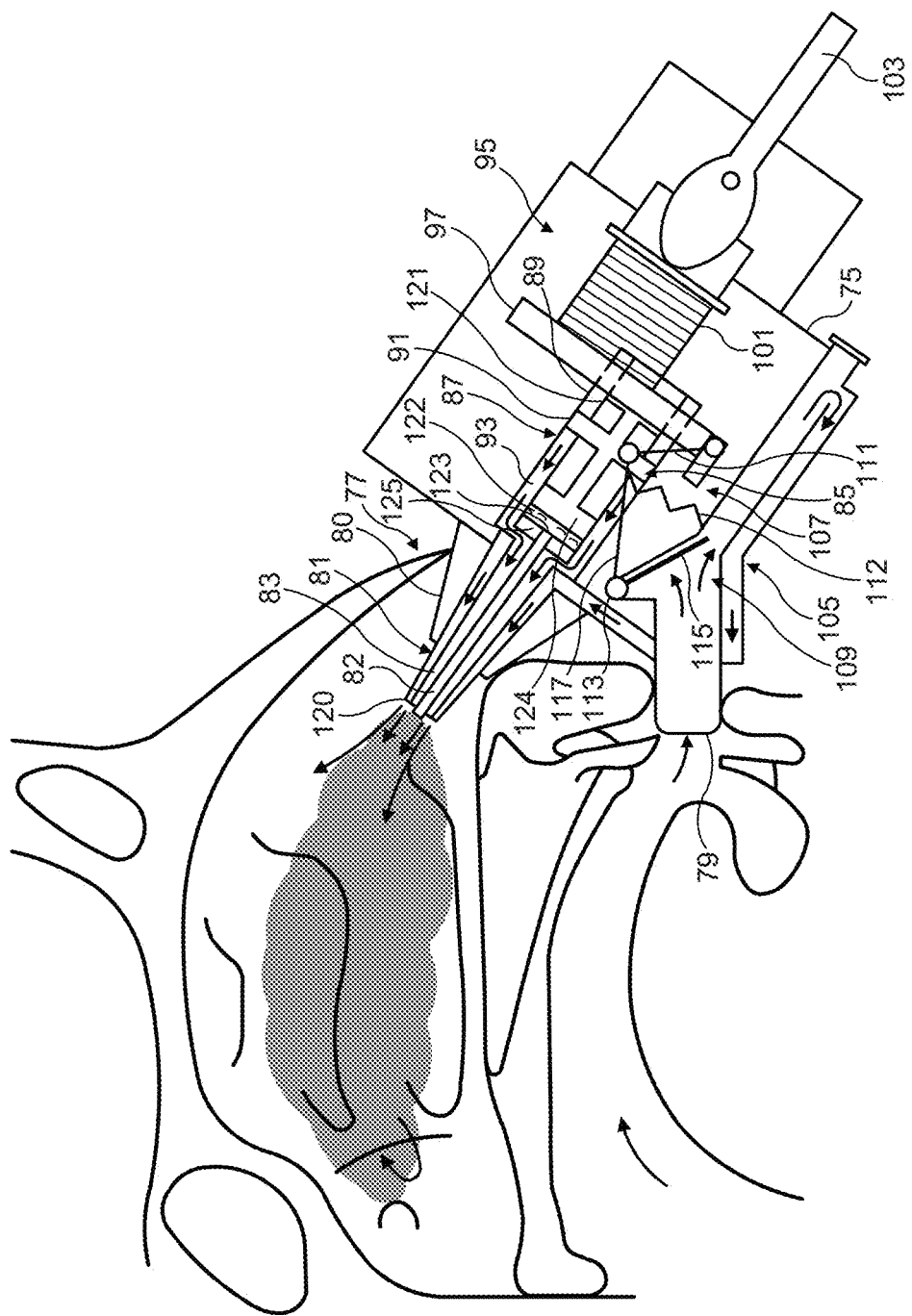

Preferred embodiments of the present invention will now be described hereinbelow by way of example only with reference to the accompanying drawings, in which:

FIG. 12 schematically illustrates the anatomy of the upper respiratory tract of a human subject;

FIG. 13 schematically illustrates a nasal delivery device in accordance with a first embodiment of the present invention;

FIG. 14 schematically illustrates the delivery device of FIG. 13 inserted in a nasal cavity of a subject for operation;

FIG. 15 schematically illustrates the delivery device of FIG. 13 during actuation;

FIG. 16 schematically illustrates the delivery device of FIG. 13 following actuation;

FIG. 17 schematically illustrates a nasal delivery device in accordance with a second embodiment of the present invention;

FIG. 18 schematically illustrates the delivery device of FIG. 17 inserted in a nasal cavity of a subject for operation;

FIG. 19 schematically illustrates the delivery device of FIG. 17 during actuation;

FIG. 20 schematically illustrates the delivery device of FIG. 17 following actuation;

FIG. 21 schematically illustrates a nasal delivery device in accordance with a third embodiment of the present invention;

FIG. 22 schematically illustrates the delivery device of FIG. 21 inserted in a nasal cavity of a subject for operation;

FIG. 23 schematically illustrates the delivery device of FIG. 21 during actuation;

FIG. 24 schematically illustrates the delivery device of FIG. 21 following actuation;

FIG. 25 schematically illustrates a nasal delivery device in accordance with a fourth embodiment of the present invention;

FIG. 26 schematically illustrates the delivery device of FIG. 25 inserted in a nasal cavity of a subject for operation;

FIG. 27 schematically illustrates the delivery device of FIG. 25 during actuation;

FIG. 28 schematically illustrates a nasal delivery device in accordance with a fifth embodiment of the present invention;

FIG. 29 schematically illustrates the delivery device of FIG. 28 inserted in a nasal cavity of a subject for operation;

FIG. 30 schematically illustrates the delivery device of FIG. 28 during actuation;

FIG. 31 schematically illustrates a nasal delivery device in accordance with a sixth embodiment of the present invention;

FIG. 32 schematically illustrates the delivery device of FIG. 31 inserted in a nasal cavity of a subject for operation;

FIG. 33 schematically illustrates the delivery device of FIG. 31 during actuation;

FIG. 34 schematically illustrates a nasal delivery device in accordance with a seventh embodiment of the present invention;

FIG. 35 schematically illustrates the delivery device of FIG. 34 inserted in a nasal cavity of a subject for operation;

FIG. 36 schematically illustrates the delivery device of FIG. 34 during actuation;

FIG. 37 schematically illustrates the delivery device of FIG. 34 following actuation;

FIG. 38 schematically illustrates a nasal delivery device in accordance with an eighth embodiment of the present invention;

FIG. 39 schematically illustrates the delivery device of FIG. 38 inserted in a nasal cavity of a subject for operation;

FIG. 40 schematically illustrates the delivery device of FIG. 38 during actuation;

FIG. 41 schematically illustrates the delivery device of FIG. 38 following actuation;

FIG. 42 schematically illustrates a nasal delivery device in accordance with a ninth embodiment of the present invention;

FIG. 43 schematically illustrates the delivery device of FIG. 42 inserted in a nasal cavity of a subject for operation;

FIG. 44 schematically illustrates the delivery device of FIG. 42 during actuation;

FIG. 45 schematically illustrates the delivery device of FIG. 42 following actuation;

FIG. 46 schematically illustrates a nasal delivery device in accordance with a tenth embodiment of the present invention, illustrated in the inoperative configuration;

FIG. 47 schematically illustrates the delivery device of FIG. 46 where the driving unit is primed for actuation;

FIG. 48 schematically illustrates the delivery device of FIG. 46 inserted in a nasal cavity of a subject for operation;

FIG. 49 schematically illustrates the delivery device of FIG. 46 during actuation where the subject has commenced exhaling and the delivery device is at the point of actuation;

FIG. 50 schematically illustrates the delivery device of FIG. 46 during actuation;

FIG. 51 schematically illustrates a nasal delivery device in accordance with an eleventh embodiment of the present invention, illustrated in the inoperative configuration;

FIG. 52 schematically illustrates the delivery device of FIG. 51 where the driving unit is primed for actuation;

FIG. 53 schematically illustrates the delivery device of FIG. 51 inserted in a nasal cavity of a subject for operation;

FIG. 54 schematically illustrates the delivery device of FIG. 51 where the subject has commenced exhaling and the delivery device is at the point of actuation;

FIG. 55 schematically illustrates the delivery device of FIG. 51 where the driving unit has been actuated, the driving unit having initiated actuation of the gas delivery unit and being at the point of initiating actuation of the substance supply unit;

FIG. 56 schematically illustrates the delivery device of FIG. 51 during full actuation;

FIG. 57 schematically illustrates a nasal delivery device in accordance with a twelfth embodiment of the present invention, illustrated in the inoperative configuration;

FIG. 58 schematically illustrates the delivery device of FIG. 57 where the driving unit is primed for actuation;

FIG. 59 schematically illustrates the delivery device of FIG. 57 inserted in a nasal cavity of a subject for operation;

FIG. 60 schematically illustrates the delivery device of FIG. 57 where the subject has commenced exhaling and the delivery device is at the point of actuation;

FIG. 61 schematically illustrates the delivery device of FIG. 57 where the driving unit has been actuated, the driving unit having initiated actuation of the gas delivery unit and being at the point of initiating actuation of the substance supply unit; and FIG. 62 schematically illustrates the delivery device of FIG. 57 during full actuation.

FIGS. 13 to 16 illustrate an exhalation breath-actuated nasal delivery device in accordance with a first embodiment of the present invention.

The delivery device comprises a housing 15, a nosepiece 17 for fitting in a nasal cavity of a subject, and a mouthpiece 19 through which the subject exhales to actuate the delivery device.

The nosepiece 17 comprises a guide member 20, in this embodiment a frusto-conical element, for guiding the nosepiece 17 into a nasal cavity of the subject, and an outlet unit 21 for delivering substance into the nasal airway of the subject. In this embodiment the nosepiece 17 is a replaceable unit.

In this embodiment the outlet unit 21 comprises a delivery channel 23 which is in fluid communication with the mouthpiece 19 such that an air flow is delivered into and through the nasal airway of the subject on exhalation by the subject through the mouthpiece 19, and a nozzle 25 for delivering substance to the nasal airway of the subject. In this embodiment the nozzle 25 is disposed in the delivery channel 23 co-axially with the same.

In this embodiment the nozzle 25 is configured to provide an aerosol spray. In an alternative embodiment, for the delivery of a liquid, the nozzle 25 could be configured to deliver a liquid jet as a column of liquid.

In this embodiment the outlet unit 21 is movably coupled to the housing 15, here as provided by a flexible coupling, such as to allow for the positioning of the outlet unit 21 in the nasal cavity of the subject, as will be described in more detail hereinbelow.

In an alternative embodiment the outlet unit 21 could be fixed to the housing 15, and the mouthpiece 19 instead movably coupled to the housing 15, here as provided by a flexible coupling, such as to allow for the positioning of the outlet unit 21 in the nasal cavity of the subject.

In this embodiment at least the tip of the delivery channel 23 comprises a tubular section of a flexible, preferably resilient, material. In a preferred embodiment the material is a semi-soft plastics material, such as silicone rubber.

In this embodiment at least the tip of the delivery channel 23 has a tapering section which narrows to the distal end thereof. The delivery channel 23, in having a narrowing taper, acts, on insertion, to expand the narrow nasal valve of the nasal cavity of the subject. In a preferred embodiment the delivery channel 23 has an elliptical section, preferably an oval section.

In a preferred embodiment the distal end of the outlet unit 21 is configured to extend at least about 2 cm, preferably at least about 3 cm, and more preferably from about 2 cm to about 3 cm, into the nasal cavity of the subject.

The nosepiece 17 further comprises at least one expandable cuff member 27 for expansion in the nasal cavity of the subject. In this embodiment the at least one cuff member 27 comprises an inflatable member.

In this embodiment the at least one cuff member 27 is in fluid communication with the delivery channel 23, whereby the air flow generated by the subject on exhalation through the mouthpiece 19 acts to inflate the at least one cuff member 27. In an alternative embodiment the delivery device could include a separate pump unit for inflating the at least one cuff member 27 subsequent to fitting of the nosepiece 17, and in a preferred embodiment subsequent to, preferably in response to, exhalation through the mouthpiece 19.

In this embodiment the at least one cuff member 27 is an inflatable member which is inflated on exhalation by the subject. In an alternative embodiment the at least one cuff member 27 could be inflated on the nosepiece 17 being located in the correct position.

In this embodiment the at least one cuff member 27 comprises a flexible balloon element which is inflated by the generation of a pressure in the delivery channel 23, with the at least one cuff member 27 deflating on the release of pressure from the delivery channel 23. In the alternative embodiment, where the at least one cuff member 27 is inflated by a separate pump unit, the at least one cuff member 27 could equally be deflated by the evacuation of gas therefrom using the same pump unit.

In one embodiment the at least one cuff member 27 could comprise a resilient balloon element which is inflated by the generation of a pressure in the delivery channel 23, with the at least one cuff member 27 returning to the original, deflated configuration on the release of pressure from the delivery channel 23.

In another embodiment the at least one cuff member 27 could comprise an inflatable sponge element, in one embodiment a foam element having an encapsulating sealing layer, which can be compressed, in this embodiment by evacuation, to adopt a compact configuration to allow for insertion into a nasal cavity of the subject and inflated, in this embodiment by breaking the vacuum, to allow for the introduction of a gas into the porous structure of the sponge element. In one embodiment such a cuff member 27 could be in selective fluid communication with the atmosphere. In another embodiment such a cuff member 27 could be in selective fluid communication with the delivery channel 23, whereby the pressure developed in the delivery channel 23 would assist in the inflation of the cuff member 27. In the alternative embodiment which includes a separate pump unit, the pump unit could be employed to assist in inflating such a cuff member 27 and in deflating the cuff member 27 by the evacuation of gas therefrom. In one embodiment the inflation could be triggered on exhalation by the subject. In another embodiment the inflation could be triggered on the nosepiece 17 being located in the correct position in the nasal cavity of the subject.

The at least one cuff member 27 is disposed to an outer surface of the outlet unit 21 such as, on expansion, to engage the inner wall of the nasal cavity of the subject. The at least one cuff member 27, in being expandable, provides for the expansion of the narrow nasal valve of the nasal cavity of the subject, the sealing of the nosepiece 17 in the nasal cavity of the subject, and the positioning, in particular the direction, of the outlet unit 21 in the nasal cavity of the subject.

In this embodiment the at least one cuff member 27 comprises a single annular cuff member 27 which is located about the outlet unit 21 such as to provide a seal between the delivery channel 23 and the inner wall of the nasal cavity of the subject when inflated.

In an alternative embodiment the at least one cuff member 27 could comprise a plurality of cuff members 27 which together provide a seal between the delivery channel 23 and the inner wall of the nasal cavity of the subject when inflated.

The delivery device further comprises a substance supply unit 29 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 25 to deliver substance from the nosepiece 17, in this embodiment as an aerosol spray.

In this embodiment the substance supply unit 29 is a multi-dose unit for delivering a plurality of metered doses of substance. In another embodiment the substance supply unit 29 could be a single-dose unit for delivering a single metered dose of substance.

The substance supply unit 29 is pre-primeable, in this embodiment by loading a resilient element, and includes a breath-actuated release mechanism 31 which, when triggered, releases the resilient element and actuates the substance supply unit 29 to deliver a metered dose of a substance through the nozzle 25.

In this embodiment the trigger mechanism 31 is configured to cause actuation of the substance supply unit 29 on generation of a predetermined flow rate through the delivery channel 23.

In another embodiment the trigger mechanism 31 could be configured to cause actuation of the substance supply unit 29 on generation of a predetermined pressure within the delivery channel 23.

In a further embodiment the trigger mechanism 31 could be configured to cause actuation of the substance supply unit 29 on generation of either one of a predetermined flow rate through the delivery channel 23 or a predetermined pressure within the delivery channel 23.

In an alternative embodiment the substance supply unit 29 could comprise a mechanical delivery pump, in particular a liquid delivery pump or a powder delivery pump, which delivers metered doses of a substance on actuation thereof.

In another alternative embodiment the substance supply unit 29 could comprise a dry powder delivery unit which delivers metered doses of a substance, as a dry powder, on actuation thereof.

In yet another alternative embodiment the substance supply unit 29 could comprise a nebulizer which delivers metered doses of a substance, as an aerosol spray, on actuation thereof.

Operation of the delivery device will now be described hereinbelow with reference to FIGS. 14 to 16 of the accompanying drawings.

Referring to FIG. 14, the nosepiece 17 is first inserted into one of the nasal cavities of a subject until the guide member 20 abuts the nares of the nostril, at which point the distal end of the outlet unit 21 extends about 2 cm into the nasal cavity of the subject, and the mouthpiece 19 is gripped in the lips of the subject.

The subject then begins to exhale through the mouthpiece 19, which exhalation acts to close the oropharyngeal velum of the subject and drive an air flow through the delivery channel 23 of the outlet unit 21, with the air flow passing into the one nasal cavity, around the posterior margin of the nasal septum and out of the other nasal cavity, thereby achieving a bi-directional air flow through the nasal airway of the subject. Exhalation through the mouthpiece 19 acts to develop a pressure in the delivery channel 23, which pressure acts to inflate the at least one cuff member 27. As illustrated in FIG. 15, the expansion of the at least one cuff member 27 acts to expand the nasal valve in the nasal cavity, seal the delivery channel 23 to the inner wall of the nasal cavity, and position the outlet unit 21 in relation to the nasal cavity of the subject. As will be noted from FIG. 15, the outlet unit 21 is forced to adopt the required position by the at least one cuff member 27, in this embodiment as accommodated by flexing of the outlet unit 21.

In this embodiment, when the flow rate developed through the delivery channel 23 reaches a predetermined value, the release mechanism 31 is triggered to actuate the substance supply unit 29 to deliver a metered dose of a substance to the nozzle 25 and into the nasal cavity of the subject. In the alternative embodiment the release mechanism 31 could be triggered on the generation of a predetermined pressure in the delivery channel 23.

Following exhalation, the pressure in the delivery channel 23 decreases and the at least one cuff member 27 deflates, as illustrated in FIG. 16, at which point the mouthpiece 19 is released and the nosepiece 17 withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 29. In a preferred embodiment, where the nosepiece 17 is replaceable, the nosepiece 17 can be replaced with a new nosepiece 17.

FIGS. 17 to 20 illustrate an exhalation breath-actuated nasal delivery device in accordance with a second embodiment of the present invention.

The delivery device of this embodiment is very similar to the delivery device of the above-described first embodiment, and thus, in order to avoid unnecessary duplication of description, only the differences will be described in detail, with like reference signs designating like parts The delivery device of this embodiment differs from that of the above-described first embodiment in further comprising an oral exhalation breath-actuatable gas supply unit 33 for delivering a gas flow through the delivery channel 23 of the outlet unit 21 in response to exhalation by a subject, and in that the mouthpiece 19 is in fluid communication with the gas supply unit 33 and not the delivery channel 23 of the outlet unit 21, whereby a gas flow is delivered to the delivery channel 23 of the outlet unit 21, and hence the nasal airway of the subject, in response to exhalation through the mouthpiece 19.

Operation of the delivery device is the same as for the above-described first embodiment, with a gas flow being delivered to the delivery channel 23 of the outlet unit 21 in response to exhalation through the mouthpiece 19.

FIGS. 21 to 24 illustrate an exhalation breath-actuated nasal delivery device in accordance with a third embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the above-described first embodiment only in that the nosepiece 17 comprises a plurality of, in this embodiment two, inflatable cuff members 27a, 27b. This arrangement of cuff members 27a, 27b enables the distalmost cuff member 27b to have a reduced size, and thereby facilitates insertion of the outlet unit 21 through the narrow nasal valve in the nasal cavity of the subject.

Operation of the delivery device is the same as for the above-described first embodiment.

FIGS. 25 to 27 illustrate an exhalation breath-actuated nasal delivery device in accordance with a fourth embodiment of the present invention.

The delivery device comprises a housing 35, a nosepiece 37 for fitting in a nasal cavity of a subject, and a mouthpiece 39 through which the subject exhales to actuate the delivery device.

The nosepiece 37 comprises a guide member 40, in this embodiment a frusto-conical element, for guiding the nosepiece 37 into the nasal cavity of the subject, and an outlet unit 41 for delivering substance into the nasal airway of the subject. In this embodiment the nosepiece 37 is a replaceable unit.

In this embodiment the outlet unit 41 comprises a delivery channel 43 which is in fluid communication with the mouthpiece 39 such that an air flow is delivered into and through the nasal airway of the subject on exhalation by the subject through the mouthpiece 39, and a nozzle 45 for delivering substance into the nasal cavity of the subject. In this embodiment the nozzle 45 is disposed in the delivery channel 43 co-axially with the same. In this embodiment the nozzle 45 is configured to provide an aerosol spray. In an alternative embodiment, for the delivery of a liquid, the nozzle 45 could be configured to deliver a liquid jet as a column of liquid.

In this embodiment at least the tip of the delivery channel 43 comprises a tubular section of a flexible, preferably resilient, material. In a preferred embodiment the material is a semi-soft plastics material, such as silicone rubber.

In this embodiment at least the tip of the delivery channel 43 has a tapering section which narrows to the distal end thereof. The delivery channel 43, in having a narrowing taper, acts, on insertion, to expand the narrow nasal valve of the nasal cavity of the subject. In a preferred embodiment the delivery channel 43 has an elliptical section, preferably an oval section.

In a preferred embodiment the outlet unit 41 is configured to extend at least about 2 cm, preferably at least about 3 cm, and more preferably from about 2 cm to about 3 cm, into the nasal cavity of the subject.

The nosepiece 37 further comprises at least one cuff member 47 for fitting in the nasal cavity of the subject. In this embodiment the at least one cuff member 47 is a resilient member which is deformable to allow for insertion into the nasal cavity of the subject and, on insertion, expansion to adopt the required position in the nasal cavity, in which position the outlet unit 41 is correctly positioned. When so positioned, the at least one cuff member 47 provides for the expansion of the narrow nasal valve in the nasal cavity, the sealing of the outlet unit 41 in the nasal cavity, and the positioning, in particular the direction, of the outlet unit 41 in the nasal cavity of the subject. In this embodiment the at least one cuff member 47 comprises a sponge member, here a foam member. In an alternative embodiment the at least one cuff member 47 could comprise a gel-filled member, such as a silicone-filled member.

In this embodiment the at least one cuff member 47 is configured such that, when inserted in the nasal cavity, the outlet unit 41 is directed at a lower region of the nasal cavity of the subject. In preferred embodiments the at least one cuff member 47 can be configured to direct the outlet unit 41 at any region of the inferior meatus and the inferior region of the middle meatus, whereby substance can be targeted in particular at the inferior nasal concha, and the adenoids and tubal ostia in the superior region of the epipharynx.

Regions in the nasal airway adjacent the inferior meatus and the inferior region of the middle meatus represent the regions in the nasal airway which provide the path of least flow resistance therethrough. With existing nasal spray systems, the delivery is such that the delivered substance flows along the floor of the nasal cavity, with the result that the substance does not reach the adenoids or the tubal ostia.

In this embodiment the at least one cuff member 47 includes at least one lobe 54, here a single lobe 54, which is configured such as to extend into, and thereby obstruct, an upper region of the nasal cavity of the subject, the at least one lobe 54 acting to force the delivered flow to follow a flow path defined by the inferior meatus and the inferior region of the middle meatus. The achievement of such a flow path, allied with an optimization of the particle size distribution, provides that a much larger fraction of substance can be delivered to sites in the inferior meatus and the inferior region of the middle meatus.

In this embodiment the at least one cuff member 47 comprises a single annular cuff member 47 which is disposed about the outlet unit 41.

In an alternative embodiment the at least one cuff member 47 could comprise a plurality of cuff members 47 which are disposed about the outlet unit 41.

The delivery device further comprises a substance supply unit 49 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 45 to deliver substance from the nosepiece 37, in this embodiment as an aerosol spray.

In this embodiment the substance supply unit 49 is a multi-dose unit for delivering a plurality of metered doses of substance. In another embodiment the substance supply unit 49 could be a single-dose unit for delivering a single metered dose of substance.

The substance supply unit 49 is pre-primeable, in this embodiment by loading a resilient element, and includes a breath-actuated release mechanism 51 which, when triggered, releases the resilient element and actuates the substance supply unit 49 to deliver a metered dose of a substance through the nozzle 45.

In this embodiment the trigger mechanism 51 is configured to cause actuation of the substance supply unit 49 on generation of a predetermined flow rate through the delivery channel 43.

In another embodiment the trigger mechanism 51 could be configured to cause actuation of the substance supply unit 49 on generation of a predetermined pressure within the delivery channel 43.

In a further embodiment the trigger mechanism 51 could be configured to cause actuation of the substance supply unit 49 on generation of either one of a predetermined flow rate through the delivery channel 43 or a predetermined pressure within the delivery channel 43.

In an alternative embodiment the substance supply unit 49 could comprise a mechanical delivery pump, in particular a liquid delivery pump or a powder delivery pump, which delivers metered doses of a substance on actuation thereof.

In another alternative embodiment the substance supply unit 49 could comprise a dry powder delivery unit which delivers metered doses of a substance, as a dry powder, on actuation thereof.

In yet another alternative embodiment the substance supply unit 49 could comprise a nebulizer which delivers metered doses of a substance, as an aerosol spray, on actuation thereof.

Operation of the delivery device will now be described hereinbelow with reference to FIGS. 26 and 27 of the accompanying drawings.

Referring to FIG. 26, the nosepiece 37 is first inserted into a nasal cavity of a subject until the guide member 40 abuts the nares of the nostril, at which point the distal end of the outlet unit 41 extends about 2 cm into the nasal cavity of the subject, and the mouthpiece 39 is gripped in the lips of the subject.

The subject then begins to exhale through the mouthpiece 39, which exhalation acts to close the oropharyngeal velum of the subject and drive an air flow through the delivery channel 43 of the outlet unit 41, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 43 reaches a predetermined value, the release mechanism 51 is triggered to actuate the substance supply unit 49 to deliver a metered dose of a substance to the nozzle 45 and into the nasal cavity of the subject. In the alternative embodiment the release mechanism 51 could be triggered on the generation of a predetermined pressure in the delivery channel 43.

Following exhalation, the mouthpiece 39 is released and the nosepiece 37 withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 49. In a preferred embodiment, where the nosepiece 37 is replaceable, the nosepiece 37 can be replaced with a new nosepiece 37.

FIGS. 28 to 30 illustrate an exhalation breath-actuated nasal delivery device in accordance with a fifth embodiment of the present invention.

The delivery device of this embodiment is very similar to the delivery device of the above-described fourth embodiment, and thus, in order to avoid unnecessary duplication of description, only the differences will be described in detail, with like reference signs designating like parts.

The delivery device of this embodiment differs from that of the above-described fourth embodiment only in the configuration of the outlet unit 41 and the at least one cuff member 47.

In this embodiment the at least one cuff member 47 is configured such that, when inserted in the nasal cavity of the subject, the outlet unit 41 is directed at a middle region of the nasal cavity of the subject. In a preferred embodiment the at least one cuff member 47 can be configured to direct the outlet unit 41 at any region of the middle meatus and the inferior region of the superior meatus, whereby substance can be targeted in particular at the middle nasal concha, the sinus infundibulum and the sinus ostia.

The middle meatus is the region of the nasal cavity located under and lateral to the middle nasal concha, with the sinus infundibulum and the sinus ostia representing the sites of the main pathologies in many very common diseases, such as chronic sinusitis, which affects about 10 to 15% of the population and has no FDA approved treatment, and nasal polyposis. The only known treatment of these conditions is the application of drops during a rigorous and complex procedure involving severe neck extension and the so-called "Mecca" position. As will be appreciated, however, owing to the complicated and often painful procedure, compliance is very poor. Existing nasal spray systems are ineffective in delivering substance to this region of the nasal cavity.

In this embodiment the at least one cuff member 47 includes upper and lower lobes 54a, 54b which are configured such as to extend into, and thereby obstruct, respective ones of the upper and lower regions of the nasal cavity of the subject, the lobes 54a, 54b acting to force a delivered flow to follow a flow path defined by the middle meatus and the inferior region of the superior meatus. The achievement of such a flow path, allied with an optimization of the particle size distribution, provides that a much larger fraction of substance can be delivered to sites in the middle meatus and the inferior region of the middle meatus.

Operation of the delivery device is the same as for the above-described fourth embodiment.

FIGS. 31 to 33 illustrate an exhalation breath-actuated nasal delivery device in accordance with a sixth embodiment of the present invention.

The delivery device of this embodiment is very similar to the delivery device of the above-described fourth embodiment, and thus, in order to avoid unnecessary duplication of description, only the differences will be described in detail, with like reference signs designating like parts.

The delivery device of this embodiment differs from that of the above-described fourth embodiment only in the configuration of the outlet unit 41 and the at least one cuff member 47.

In this embodiment the at least one cuff member 47 is configured such that, when inserted in the nasal cavity of the subject, the outlet unit 41 is directed at a superior region of the nasal cavity of the subject. In a preferred embodiment the at least one cuff member 47 can be configured to direct the outlet unit 41 at any region of the superior meatus, and in particular provide for the targeting of the superior nasal concha and the olfactory region.

The olfactory region is located in the superior region of the nasal cavity and typically has a surface area of from about 4 to 6 cm². The olfactory region represents the only region where it is possible to circumvent the blood-to-brain barrier (BBB) and enable communication with the cerebrospinal fluid (CSF) and the brain. Such delivery is necessary to enable effective treatment of neurological diseases, such as Alzheimer's and Parkinson's disease, psychiatric diseases and intracerebral infections.

The olfactory region is reached through narrow slit-like passages and the delivery of substance to this region is not possible using existing nasal delivery systems.

In existing nasal spray systems, substantially all of the particles are far too large to pass through the passages in communication with the olfactory region. Indeed, such spray systems are specifically designed to deliver particles having an average diameter of greater than 10 μm in order to comply with the FDA requirements which require that the maximum fraction of particles having a diameter of less than 10 μm be 5% of the total fraction. The reason for this requirement is that, where the velum is not closed, as would be the case where a subject inhales through the nose as prescribed for delivery, particles having a diameter of less than 10 μm could escape from the nasal cavity and be inhaled into the lungs.

In addition, in existing nasal spray systems, the flow characteristics of particles delivered into the nasal cavity are not suited to enable delivery through the passages communicating with the olfactory region.

Furthermore, the sniffing action by a subject during delivery causes the particles to be drawn into the inferior and middle regions of the nasal cavity, where the flow resistance is the lowest, with only a minimal fraction, if any, of the particles being delivered to the olfactory region.

In this embodiment, by ensuring closure of the velum in delivery and optimizing both the particle size distribution so as to include a larger fraction of smaller particles, typically having a particle size of less than 10 μm, and the aerodynamic delivery conditions, the delivery device provides for the effective delivery of substance to the olfactory region. Such a delivery regime has not previously been known, and has been recognised by the present applicant as providing an improved delivery device and delivery method.

In this embodiment the at least one lobe 54 of the at least one cuff member 47 is configured such as to extend into, and thereby obstruct, a lower region of the nasal cavity of the subject, the at least one lobe 54 acting to force a delivered flow to follow a flow path defined by the superior meatus and in particular the olfactory region. The achievement of such a flow path, allied with an optimization of the particle size distribution, provides that a much larger fraction of substance can be delivered to sites in the superior meatus and in particular the olfactory region.

Operation of the delivery device is the same as for the above-described fourth embodiment.

FIGS. 34 to 37 illustrate an exhalation breath-actuated nasal delivery device in accordance with a seventh embodiment of the present invention.

The delivery device comprises a housing 55, a nosepiece 57 for fitting in a nasal cavity of a subject, and a mouthpiece 59 through which the subject exhales to actuate the delivery device.

The nosepiece 57 comprises a guide member 60, in this embodiment a frusto-conical element, for guiding the nosepiece 57 into a nasal cavity of the subject, and an outlet unit 61 for delivering substance into the nasal airway of the subject. In this embodiment the nosepiece 57 is a replaceable unit.

In this embodiment the outlet unit 61 comprises a delivery channel 63 which is in fluid communication with the mouthpiece 59 such that an air flow is delivered into and through the nasal airway of the subject on exhalation by the subject through the mouthpiece 59, and a nozzle 65 for delivering substance to the nasal airway of the subject. In this embodiment the nozzle 65 is disposed in the delivery channel 63 co-axially with the same. In this embodiment the nozzle 65 is configured to provide an aerosol spray. In an alternative embodiment, for the delivery of a liquid, the nozzle 65 could be configured to deliver a liquid jet as a column of liquid.

In this embodiment the outlet unit 61 is movably coupled to the housing 55, here as provided by a flexible coupling, such as to allow for the positioning of the outlet unit 61 in the nasal cavity of the subject, as will be described in more detail hereinbelow.

In an alternative embodiment the outlet unit 61 could be fixed to the housing 55, and the mouthpiece 59 instead movably coupled to the housing 55, here as provided by a flexible coupling, such as to allow for the positioning of the outlet unit 61 in the nasal cavity of the subject.

In this embodiment at least the tip of the delivery channel 63 comprises a tubular section of a flexible, preferably resilient, material. In a preferred embodiment the material is a semi-soft plastics material, such as silicone rubber.

In this embodiment at least the tip of the delivery channel 63 has a tapering section which narrows to the distal end thereof. The delivery channel 63, in having a narrowing taper, acts, on insertion, to expand the narrow nasal valve of the nasal cavity of the subject. In a preferred embodiment the delivery channel 63 has an elliptical section, preferably an oval section.

In a preferred embodiment the distal end of the outlet unit 61 is configured to extend at least about 2 cm, preferably at least about 3 cm, and more preferably from about 2 cm to about 3 cm, into the nasal cavity of the subject.

The nosepiece 57 further comprises at least one expandable cuff member 67 for expansion in the nasal cavity of the subject. In this embodiment the at least one cuff member 67 comprises an inflatable member.

In this embodiment the at least one cuff member 67 is in fluid communication with the delivery channel 63, whereby the air flow generated by the subject on exhalation through the mouthpiece 59 acts to inflate the at least one cuff member 67. In an alternative embodiment the delivery device could include a separate pump unit for inflating the at least one cuff member 67 subsequent to fitting of the nosepiece 57, and in a preferred embodiment subsequent to, preferably in response to, exhalation through the mouthpiece 59.

In this embodiment the at least one cuff member 67 is an inflatable member which is inflated on exhalation by the subject. In an alternative embodiment the at least one cuff member 67 could be inflated on the nosepiece 57 being located in the correct position.

In this embodiment the at least one cuff member 67 comprises a flexible balloon element which is inflated by the generation of a pressure in the delivery channel 63, with the at least one cuff member 67 deflating on the release of pressure from the delivery channel 63. In the alternative embodiment, where the at least one cuff member 67 is inflated by a separate pump unit, the at least one cuff member 67 could equally be deflated by the evacuation of gas therefrom using the same pump unit.

In one embodiment the at least one cuff member 67 could comprise a resilient balloon element which is inflated by the generation of a pressure in the delivery channel 63, with the at least one cuff member 67 returning to the original, deflated configuration on the release of pressure from the delivery channel 63.

In another embodiment the at least one cuff member 67 could comprise an inflatable sponge element, in one embodiment a foam element having an encapsulating sealing layer, which can be compressed, in this embodiment by evacuation, to adopt a compact configuration to allow for insertion into a nasal cavity of the subject and inflated, in this embodiment by breaking the vacuum, to allow for the introduction of a gas into the porous structure of the sponge element. In one embodiment such a cuff member 67 could be in selective fluid communication with the atmosphere. In another embodiment such a cuff member 67 could be in selective fluid communication with the delivery channel 63, whereby the pressure developed in the delivery channel 63 would assist in the inflation of the cuff member 67. In the alternative embodiment which includes a separate pump unit, the pump unit could be employed to assist in inflating such a cuff member 67 and in deflating the cuff member 67 by the evacuation of gas therefrom. In one embodiment the inflation could be triggered on exhalation by the subject. In another embodiment the inflation could be triggered on the nosepiece 57 being located in the correct position in the nasal cavity of the subject.

The at least one cuff member 67 is disposed to an outer surface of the outlet unit 61 such as, on expansion, to engage the inner wall of the nasal cavity of the subject. The at least one cuff member 67, in being expandable, provides for the expansion of the narrow nasal valve of the nasal cavity of the subject, the sealing of the nosepiece 57 in the nasal cavity of the subject, and the positioning, in particular the direction, of the outlet unit 61 in the nasal cavity of the subject.

In this embodiment the at least one cuff member 67 comprises a single annular cuff member 67 which is located about the outlet unit 61 such as to provide a seal between the delivery channel 63 and the inner wall of the nasal cavity of the subject when inflated.

In an alternative embodiment the at least one cuff member 67 could comprise a plurality of cuff members 67 which together provide a seal between the delivery channel 63 and the inner wall of the nasal cavity of the subject when inflated.

In this embodiment the at least one cuff member 67 is configured such that, when inserted in the nasal cavity, the outlet unit 61 is directed at a lower region of the nasal cavity of the subject. In preferred embodiments the at least one cuff member 67 can be configured to direct the outlet unit 61 at any region of the inferior meatus and the inferior region of the middle meatus, whereby substance can be targeted in particular at the inferior nasal concha, and the adenoids and tubal ostia in the superior region of the epipharynx.

Regions in the nasal airway adjacent the inferior meatus and the inferior region of the middle meatus represent the regions in the nasal airway which provide the path of least flow resistance therethrough. With existing nasal spray systems, the delivery is such that the delivered substance flows along the floor of the nasal cavity, with the result that the substance does not reach the adenoids or the tubal ostia.

In this embodiment the at least one cuff member 67 includes at least one lobe 74, here a single lobe 74, which is configured such as to extend into, and thereby obstruct, an upper region of the nasal cavity of the subject, the at least one lobe 74 acting to force the delivered flow to follow a flow path defined by the inferior meatus and the inferior region of the middle meatus. The achievement of such a flow path, allied with an optimization of the particle size distribution, provides that a much larger fraction of substance can be delivered to sites in the inferior meatus and the inferior region of the middle meatus.

In this embodiment the at least one cuff member 67 comprises a single annular cuff member 67 which is disposed about the outlet unit 61.

In an alternative embodiment the at least one cuff member 67 could comprise a plurality of cuff members 67 which are disposed about the outlet unit 61.

The delivery device further comprises a substance supply unit 69 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 65 to deliver substance from the nosepiece 57, in this embodiment as an aerosol spray.

In this embodiment the substance supply unit 69 is a multi-dose unit for delivering a plurality of metered doses of substance. In another embodiment the substance supply unit 69 could be a single-dose unit for delivering a single metered dose of substance.

The substance supply unit 69 is pre-primeable, in this embodiment by loading a resilient element, and includes a breath-actuated release mechanism 71 which, when triggered, releases the resilient element and actuates the substance supply unit 69 to deliver a metered dose of a substance through the nozzle 65.

In this embodiment the trigger mechanism 71 is configured to cause actuation of the substance supply unit 69 on generation of a predetermined flow rate through the delivery channel 63.

In another embodiment the trigger mechanism 71 could be configured to cause actuation of the substance supply unit 69 on generation of a predetermined pressure within the delivery channel 63.

In a further embodiment the trigger mechanism 71 could be configured to cause actuation of the substance supply unit 69 on generation of either one of a predetermined flow rate through the delivery channel 63 or a predetermined pressure within the delivery channel 63.

In an alternative embodiment the substance supply unit 69 could comprise a mechanical delivery pump, in particular a liquid delivery pump or a powder delivery pump, which delivers metered doses of a substance on actuation thereof.

In another alternative embodiment the substance supply unit 69 could comprise a dry powder delivery unit which delivers metered doses of a substance, as a dry powder, on actuation thereof.

In yet another alternative embodiment the substance supply unit 69 could comprise a nebulizer which delivers metered doses of a substance, as an aerosol spray, on actuation thereof.

Operation of the delivery device will now be described hereinbelow with reference to FIGS. 35 to 37 of the accompanying drawings.

Referring to FIG. 35, the nosepiece 57 is first inserted into one of the nasal cavities of a subject until the guide member 60 abuts the nares of the nostril, at which point the distal end of the outlet unit 61 extends about 2 cm into the nasal cavity of the subject, and the mouthpiece 59 is gripped in the lips of the subject.

The subject then begins to exhale through the mouthpiece 59, which exhalation acts to close the oropharyngeal velum of the subject and drive an air flow through the delivery channel 63 of the outlet unit 61, with the air flow passing into the one nasal cavity, around the posterior margin of the nasal septum and out of the other nasal cavity, thereby achieving a bi-directional air flow through the nasal airway of the subject. Exhalation through the mouthpiece 59 acts to develop a pressure in the delivery channel 63, which pressure acts to inflate the at least one cuff member 67. As illustrated in FIG. 36, the expansion of the at least one cuff member 67 acts to expand the nasal valve in the nasal cavity, seal the delivery channel 63 to the inner wall of the nasal cavity, and position the outlet unit 61 in relation to the nasal cavity of the subject. As will be noted from FIG. 36, the outlet unit 61 is forced to adopt the required position by the at least one cuff member 67, in this embodiment as accommodated by flexing of the outlet unit 61.

In this embodiment, when the flow rate developed through the delivery channel 63 reaches a predetermined value, the release mechanism 71 is triggered to actuate the substance supply unit 69 to deliver a metered dose of a substance to the nozzle 65 and into the nasal cavity of the subject. In the alternative embodiment the release mechanism 71 could be triggered on the generation of a predetermined pressure in the delivery channel 63.

Following exhalation, the pressure in the delivery channel 63 decreases and the at least one cuff member 67 deflates, as illustrated in FIG. 37, at which point the mouthpiece 59 is released and the nosepiece 57 withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 69. In a preferred embodiment, where the nosepiece 57 is replaceable, the nosepiece 57 can be replaced with a new nosepiece 57.

FIGS. 38 to 41 illustrate an exhalation breath-actuated nasal delivery device in accordance with an eighth embodiment of the present invention.

The delivery device of this embodiment is very similar to the delivery device of the above-described seventh embodiment, and thus, in order to avoid unnecessary duplication of description, only the differences will be described in detail, with like reference signs designating like parts.

The delivery device of this embodiment differs from that of the above-described seventh embodiment only in the configuration of the outlet unit 61 and the at least one cuff member 67.

In this embodiment the at least one cuff member 67 is configured such that, when inserted in the nasal cavity of the subject, the outlet unit 61 is directed at a middle region of the nasal cavity of the subject. In a preferred embodiment the at least one cuff member 67 can be configured to direct the outlet unit 61 at any region of the middle meatus and the inferior region of the superior meatus, whereby substance can be targeted in particular at the middle nasal concha, the sinus infundibulum and the sinus ostia.

The middle meatus is the region of the nasal cavity located under and lateral to the middle nasal concha, with the sinus infundibulum and the sinus ostia representing the sites of the main pathologies in many very common diseases, such as chronic sinusitis, which affects about 10 to 15% of the population and has no FDA approved treatment, and nasal polyposis. The only known treatment of these conditions is the application of drops during a rigorous and complex procedure involving severe neck extension and the so-called "Mecca" position. As will be appreciated, however, owing to the complicated and often painful procedure, compliance is very poor. Existing nasal spray systems are ineffective in delivering substance to this region of the nasal cavity.

In this embodiment the at least one cuff member 67 includes upper and lower lobes 74*a*, 74*b* which are configured such as to extend into, and thereby obstruct, respective ones of the upper and lower regions of the nasal cavity of the subject, the lobes 74*a*, 74*b* acting to force a delivered flow to follow a flow path defined by the middle meatus and the inferior region of the superior meatus. The achievement of such a flow path, allied with an optimization of the particle size distribution, provides that a much larger fraction of substance can be delivered to sites in the middle meatus and the inferior region of the middle meatus.

Operation of the delivery device is the same as for the above-described seventh embodiment.

FIGS. 42 to 45 illustrate an exhalation breath-actuated nasal delivery device in accordance with a ninth embodiment of the present invention.

The delivery device of this embodiment is very similar to the delivery device of the above-described seventh embodiment, and thus, in order to avoid unnecessary duplication of description, only the differences will be described in detail, with like reference signs designating like parts.

The delivery device of this embodiment differs from that of the above-described seventh embodiment only in the configuration of the outlet unit 61 and the at least one cuff member 67.

In this embodiment the at least one cuff member 67 is configured such that, when inserted in the nasal cavity of the subject, the outlet unit 61 is directed at a superior region of the nasal cavity of the subject. In a preferred embodiment the at least one cuff member 67 can be configured to direct the outlet unit 61 at any region of the superior meatus, and in particular provide for the targeting of the superior nasal concha and the olfactory region.

The olfactory region is located in the superior region of the nasal cavity and typically has a surface area of: from about 4 to 6 cm$^2$. The olfactory region represents the only region where it is possible to circumvent the blood-to-brain barrier (BBB) and enable communication with the cerebrospinal fluid (CSF) and the brain. Such delivery is necessary to enable effective treatment of neurological diseases, such as Alzheimer's and Parkinson's disease, psychiatric diseases and intracerebral infections.

The olfactory region is reached through narrow slit-like passages and the delivery of substance to this region is not possible using existing nasal delivery systems.

In existing nasal spray systems, substantially all of the particles are far too large to pass through the passages in communication with the olfactory region. Indeed, such spray systems are specifically designed to deliver particles having an average diameter of greater than 10 μm in order to comply with the FDA requirements which require that the maximum: fraction of particles having an average diameter of less than 10 μm be 5% of the total fraction. The reason for this requirement is that, where the velum is not closed, as would be the case where a subject inhales through the nose as prescribed for delivery, particles having an average diameter of less than 10 μm could escape from the nasal cavity and be inhaled into the lungs.

In addition, in existing nasal spray systems, the flow rate of particles delivered into the nasal cavity is too great to enable delivery through the passages communicating with the olfactory region.

Furthermore, inhalation by a subject during delivery causes the particles to be drawn into the inferior and middle regions of the nasal cavity, where the flow resistance is the lowest, with only a minimal fraction, if any, of the particles being delivered to the olfactory region.

In this embodiment, by ensuring closure of the velum in delivery and optimizing both the particle size distribution so as to include a larger fraction of smaller particles, typically having a particle size of less than 10 μm, and the aerodynamic delivery conditions, the delivery device provides for the effective delivery of substance to the olfactory region. Such a delivery regime has not previously been known, and has been recognised by the present applicant as providing an improved delivery device and delivery method.

In this embodiment the at least one lobe 74 of the at least one cuff member 67 is configured such as to extend into, and thereby obstruct, a lower region of the nasal cavity of the subject, the at least one lobe 74 acting to force a delivered flow to follow a flow path defined by the superior meatus and in particular the olfactory region. The achievement of such a flow path, allied with an optimization of the particle size distribution, provides that a much larger fraction of substance can be delivered to sites in the superior meatus and in particular the olfactory region.

Operation of the delivery device is the same as for the above-described seventh embodiment.

FIGS. 36 to 50 illustrate an exhalation breath-actuated nasal delivery device in accordance with a tenth embodiment of the present invention.

The delivery device comprises a housing 75, a nosepiece 77 for fitting in a nasal cavity of a subject, and a mouthpiece 79 through which the subject exhales to actuate the delivery device.

The nosepiece 77 comprises a cuff member 80, in this embodiment a frusto-conical element, for positioning the nosepiece 77 in the nasal cavity of the subject and providing a fluid-tight seal therewith, and an outlet unit 81 for delivering substance into the nasal airway of the subject.

In this embodiment the outlet unit 81 comprises a nozzle 82 from which substance is delivered into the nasal cavity of the subject, and a delivery channel 83 through which a gas flow, separate from the exhalation breath of the subject, is delivered to interact with the substance delivered from the nozzle 82. This configuration, in interacting with the substance and altering the characteristics of the delivered substance, advantageously provides for improved delivery of the substance.

In this embodiment the nozzle 82 is configured to provide an aerosol spray. In an alternative embodiment, for the delivery of a liquid, the nozzle 82 could be configured to deliver a liquid jet as a column of liquid.

In this embodiment the nozzle 82 is disposed in the delivery channel 83 co-axially with the same. In this embodiment the delivery channel 83 is an annular channel which surrounds the nozzle 82 such as to define an annular gas flow which interacts with the substance delivered from the nozzle 82.

The delivery device further comprises a substance supply unit 85 which is fluidly connected to the nozzle 82 such as to deliver a metered dose of a substance on actuation thereof. In this embodiment the substance supply unit 85 comprises a mechanical pump for delivering a metered dose of a substance on actuation thereof.

The delivery device further comprises a gas supply unit 87 which is fluidly connected to the delivery channel 83 for supplying a gas flow therethrough. The gas supply unit 87 comprises a cylinder 89, a piston 91 which is movably disposed within the cylinder 89 and defines a chamber 93 forward thereof which contains a gas, with a volume of the contained gas, typically about 5 ml, being expelled from the chamber 93 on actuation of the gas supply unit 87.

The delivery device further comprises a driving unit 95 which is actuatable to actuate the substance supply unit 85 and the gas supply unit 87.

The driving unit 95 comprises a drive member 97, in this embodiment a block, which is coupled, here commonly coupled, to the body of the substance supply unit 85 and the piston 91 of the gas supply unit 87 and movable between a first, rest position (as illustrated in FIGS. 46 to 49). in which the substance supply unit 85 and the gas supply unit 87 are in the non-actuated positions and a second, actuated position (as illustrated in FIG. 50) in which the body of the substance supply unit 85 and the piston 91 of the gas supply unit 87 are advanced to the actuated positions, and a return biasing element 99, in this embodiment a resilient element, particularly a compression spring, for returning the drive member 97 to the rest position.

The driving unit 95 further comprises a load biasing element 101, in this embodiment a resilient element, particularly a compression spring, for biasing the drive member 97 in an actuating direction when in the rest position, and a loading member 103, in this embodiment a lever, for loading the load biasing element 101 such as to bias the drive member 97 when in the rest position with an actuation force. The loading member 103 is movable between a first, inoperative position (as illustrated in FIG. 46) in which the load biasing element 101 is not loaded thereby, and a second, operative position (as illustrated in FIGS. 47 to 49) in which the biasing element 101, when restrained, loads the drive member 97 with the actuation force.

The delivery device further comprises a trigger mechanism 105 which is configured normally to lock the drive member 97 of the driving unit 95 in the rest position and release the same on exhalation by the subject through the mouthpiece 79, which drive member 97, when loaded by the load biasing element 101, once released acts commonly to actuate the substance supply unit 85 and the gas supply unit 87.

In this embodiment the trigger mechanism 105 is configured to cause actuation of the driving unit 95 on generation of a predetermined flow rate through the mouthpiece 79.

In another embodiment the trigger mechanism 105 could be configured to cause actuation of the driving unit 95 on generation of a predetermined pressure within the mouthpiece 79.

In this embodiment the trigger mechanism 105 comprises a linkage assembly 107 which includes first and second link elements 109, 111, and a biasing element 112, in this embodiment a resilient element, particularly a tension spring, for biasing the linkage assembly 107 to a locking configuration (as illustrated in FIGS. 46 to 48) in which the linkage assembly 107 acts to lock the drive member 97 of the driving unit 95 in the rest position and prevent movement thereof when loaded by the load biasing element 101.

One of the link elements 109 includes a pivot 113 about which the same is rotatable, and first and second arms 115, 117. One of the arms 115 extends into the mouthpiece 79 and, when the linkage assembly 107 is in the locking configuration, is biased to a rest position (as illustrated in FIGS. 46 to 48) in which the flow path through the mouthpiece 79 is substantially closed, the one arm 115 thereby providing a vane to be acted upon by the exhalation breath of the subject.

The other of the link elements 111 is pivotally coupled at one end to the distal end of the other, second arm 117 of the first link element 109 and at the other end to the drive member 97 of the driving unit 95; the second arm 117 of the first link element 109 being angularly positioned relative to the first arm 115 thereof such that, when the linkage assembly 107 is in the locking configuration, the second arm 117 of the first link element 109 and the second link element 111 enclose an angle of less than 180 degrees on the side opposite to the first arm 115 of the first link element 109, whereby the second arm 117 of the first link element 109 and the second link element 111 are over-centered and support the drive member 97 of the driving unit 95 when loaded.

Operation of the delivery device will now be described hereinbelow with reference to FIGS. 47 to 50 of the accompanying drawings.

In a first step, as illustrated in FIG. 47, the loading member 103 is operated to bias the biasing element 101 and load the drive member 97 of the driving unit 95 with the actuation force.

Referring to FIG. 48, the nosepiece 77 is then first inserted into a nasal cavity of a subject until the cuff member 80 is fitted in the nares of the nostril, at which point the distal end of the outlet unit 81 extends about 2 cm into the nasal cavity of the subject, and the mouthpiece 79 is gripped in the lips of the subject.

The subject then begins to exhale through the mouthpiece 79, which exhalation acts to close the oropharyngeal velum of the subject and drive an air flow over the first arm 115 of the first link element 109 of the linkage assembly 107 which extends into the mouthpiece 79. While the flow rate developed is not sufficient to actuate the trigger mechanism 105, the linkage assembly 107 of the trigger mechanism 105 acts to retain the drive member 97 of the driving unit 95 in the locked position, whereby the substance supply unit 85 and the gas supply unit 87 are not actuated. When the flow rate developed reaches a predetermined value, as illustrated in FIG. 49, the rotation of the first arm 115 of the first link element 109 is such as to rotate the second arm 117 of the first link element 109 to a position in which the support provided together with the second link element 111 is unstable and collapses. Referring to FIG. 50, this collapse of the linkage assembly 107 enables the drive member 97 of the driving unit 95 to be moved by the load biasing element 101 to the actuated position, which movement actuates the substance supply unit 85 to deliver a metered dose of a substance through the nozzle 82 and the gas supply unit 87 to deliver a metered volume of a gas through the delivery channel 83, which gas flow interacts with the delivered substance to modify the characteristics of the delivered substance, and thereby provide for improved delivery to the nasal airway of the subject.

Following actuation, the mouthpiece 79 is released and the nosepiece 77 is withdrawn from the nasal cavity of the subject.

The loading member 103 of the driving unit 95 is then returned to the inoperative position, and the drive member 97 of the driving unit 95 is returned to the rest position by the return biasing element 99. The return of the drive member 97 to the rest position causes the body of the substance supply unit 85 and the piston 91 of the gas supply unit 87 to be returned to the rest positions.

Following the return of the drive member 97 to the rest position, the linkage assembly 107 again adopts the locking configuration, with the linkage assembly 107 being maintained in the locking configuration by the linkage biasing element 112. In this configuration, the delivery device is ready for further use.

FIGS. 51 to 56 illustrate an exhalation breath-actuated nasal delivery device in accordance with an eleventh embodiment of the present invention.

The delivery device of this embodiment is very similar to the delivery device of the above-described tenth embodiment, and thus, in order to avoid unnecessary duplication of description, only the differences will be described in detail, with like reference signs designating like parts.

The delivery device of this embodiment differs from that of the above-described tenth embodiment only in the configuration of the driving unit 95.

In this embodiment the drive member 97 of the drive unit 95 is not configured to commence actuation of the substance supply unit 85 and the gas supply unit 87 at the same instant as in the above-described tenth embodiment, but rather is configured such that actuation of the gas supply unit 87 is commenced prior to the actuation of the substance supply unit 85, whereby an interacting gas flow is delivered from the delivery channel 83 of the outlet unit 81 prior to the delivery of substance from the nozzle 82 and then during the delivery of substance from the nozzle 82 such as to interact with the same.

In this embodiment the delayed actuation of the substance supply unit 85 is achieved by configuring the drive member 97 such as to be spaced from the body of the substance supply unit 85 when the drive member 97 is in the rest position, whereby the drive member 97 has to be advanced a predetermined distance, corresponding to a predetermined time period, prior to common actuation of the substance supply unit 85 and the gas supply unit 87. In this embodiment the substance supply unit 85 includes a biasing element 119 for returning the substance supply unit 85 to the rest position following actuation. With this configuration, the interval between actuation of the gas supply unit 87 and the common actuation of the substance supply unit 85 and the gas supply unit 87 can be controlled by altering the spacing between the drive member 97 and the body of the substance supply unit 85.

Operation of the delivery device is the same as for the above-described tenth embodiment.

FIGS. 57 to 62 illustrate an exhalation breath-actuated nasal delivery device in accordance with a twelfth embodiment of the present invention.

The delivery device of this embodiment is very similar to the delivery device of the above-described tenth embodiment, and thus, in order to avoid unnecessary duplication of description, only the differences will be described in detail, with like reference signs designating like parts.

The delivery device of this embodiment differs from that of the above-described tenth embodiment only in the configuration of the outlet unit 81 and in the integration of the substance supply unit 85 and the gas delivery unit 87.

In this embodiment the outlet unit 81 includes a second delivery channel 120, here an annular channel which is disposed co-axially about the nozzle 82, through which an air flow from an exhalation breath of a subject is delivered, such as to entrain with the substance delivered from the nozzle 82. In this embodiment the second delivery channel 120 is fluidly connected to the mouthpiece 79 downstream of the trigger mechanism, and the mouthpiece 79 includes a pressure-release valve which allows for the development of a flow above the release pressure of the pressure-release valve where a flow, or at least not a sufficient flow, cannot be developed through the nasal airway of the subject.

In this embodiment the substance supply unit 85 comprises a piston unit which is disposed within the chamber 93 of the gas supply unit 87. The substance supply unit 85 comprises a cylinder 121 which defines a chamber 122 and into one, forward end of which a hollow needle 123 extends as an extension of the nozzle 82. The substance supply unit 85 further comprises first and second pistons 124, 125 which contain a volume of substance therebetween and are movably disposed within the chamber 122.

With this configuration, the forward, piston 125 is driven forwardly on the rear, piston 124 being driven forwardly, the substance contained between the pistons 124, 125 being substantially incompressible. The forward piston 125 is a puncturable member which is punctured by the needle 123 of the nozzle 82 on being driven onto the same, with the needle 123 of the nozzle 82 being in fluid communication with the substance contained between the pistons 124, 125 on puncturing the forward piston 125.

In this embodiment the forward piston 125 of the substance supply unit 85 is spaced from the needle 123 of the nozzle 82 by a predetermined distance such that the piston 91 of the gas supply unit 87, which drives the rear piston 124 of the substance supply unit 85, is required to be driven a predetermined distance before the forward piston 125 of the substance supply unit 85 is ruptured and substance is delivered through the nozzle 82. In this way, actuation of the gas supply unit 87 is initiated prior to the actuation of the substance supply unit 85, whereby an interacting gas flow is delivered from the delivery channel 83 of the outlet unit 81 prior to the delivery of substance from the nozzle 82 and then during the delivery of substance from the nozzle 82 such as to interact with the same. In this embodiment the interval between actuation of the gas supply unit 87 and the common actuation of the substance supply unit 85 and the gas supply unit 87 can be controlled by altering the spacing between the forward piston 125 of the substance supply unit 85 and the needle 123 of the nozzle 82.

Operation of the delivery device is the same as for the above-described tenth embodiment.

Finally, it will be understood that the present invention has been described in its preferred embodiments and can be modified in many different ways without departing from the scope of the invention as defined by the appended claims.

In particular, it should be understood that features of any of the embodiments could be incorporated in any other of the embodiments. For example, the second and third embodiments could incorporate features of the first embodiment, in particular the at least one expandable cuff member 23 as in the first embodiment.

Also, in embodiments where an entraining gas flow is not required through the nasal airways of subjects, ones of the embodiments could be modified to include no such gas flow. For example, the first-described embodiment could be modified such that the outlet unit 21 includes only the nozzle 23 and no delivery channel 23.

In the described embodiments the mouthpieces are configured to be gripped in the lips of a subject. In alternative embodiments the mouthpieces could be configured to be gripped by the teeth of a subject and sealed by the lips of the subject. In preferred embodiments the mouthpieces could be specifically configured to have one or both of a shape or geometry which allows the delivery devices to be gripped repeatedly in the same position, thereby providing for the respective nosepieces to be reliably inserted in the same position in the nasal cavity.

In preferred embodiments the delivery devices are configured to deliver substance through one nostril of a subject at such a pressure as to flow around the posterior margin of the nasal septum and out of the other nostril of the subject, thereby achieving bi-directional delivery through the nasal cavities as disclosed in WO-A-00/51672. In alternative embodiments the delivery device could be configured to deliver substance at a reduced pressure which is not sufficient to achieve bi-directional delivery through the nasal cavities. Such embodiments are still advantageous as compared to known delivery devices in providing for velum closure and being capable of achieving targeted delivery, particularly when certain regions of the nasal cavity are obstructed by cuff members.

Also, in another modification, the delivery devices could include two nosepieces, in one embodiment configured for the simultaneous delivery to each of the nasal cavities. Such embodiments would advantageously provide for three-point fixation of the delivery devices via the nosepieces and the mouthpieces.

The invention claimed is:

1. A method of treating autism or schizophrenia, consisting of:
   a first step and, separately, a second step;
   wherein the first step includes delivering a first substance to the upper posterior, olfactory region of a nasal airway of a subject, which includes the olfactory bulb and the trigeminal nerve of the subject, wherein the first substance comprises between 1 IU and 15 IU of oxytocin; and
   wherein the second step includes delivering a second substance to promote transfer of the first substance, wherein the second substance is a liquid and delivered after the first substance.

2. The method of claim 1, wherein the first substance is a powder.

3. The method of claim 2, wherein the first substance is mixed with a bulking agent.

4. The method of claim 1, wherein the first substance is a liquid.

5. The method of claim 1, wherein the first substance includes a thickening agent, which thickens on exposure to moisture.

6. The method of claim 5, wherein the thickening agent comprises one or more of pectin, agar-agar, lignin, algin, gums and cellulose.

7. The method of claim 1, wherein the first substance is administered once daily.

8. The method of claim 1, wherein the first substance is administered twice daily.

9. The method of claim 1, wherein the delivery of the first substance is targeted to provide for one or both of nose-to-brain (N2B) and systemic delivery of the first substance.

10. The method of claim 9, wherein the delivery is targeted to provide for both nose-to-brain (N2B) and systemic delivery of the first substance, and the first substance is formulated to provide for greater N2B delivery than systemic delivery of the first substance.

11. The method of claim 9, wherein the delivery of the first substance is targeted to provide for both nose-to-brain (N2B) and systemic delivery, and the first substance is formulated to provide for greater systemic delivery than N2B delivery of the first substance.

12. The method of claim 1, wherein the first substance further comprises a decongestant.

13. The method of claim 1, wherein the first substance comprises less than about 10 IU of oxytocin.

14. The method of claim 1, wherein the first substance comprises less than about 5 IU of oxytocin.

15. The method of claim 1, wherein the first substance comprises from about 1 IU to about 10 IU of oxytocin.

16. The method of claim 1, wherein the first substance comprises from about 3 IU to about 10 IU of oxytocin.

17. The method of claim 1, wherein the first substance comprises from about 3 IU to about 5 IU of oxytocin.

18. The method of claim 1, wherein the oxytocin of the first substance is a first active ingredient and wherein the first substance includes a second active ingredient.

19. A method of treating autism or schizophrenia, consisting of:
   a first step and, separately, a second step;
   wherein the first step includes delivering a first substance to the upper posterior, olfactory region of a nasal airway of a subject, which includes the olfactory bulb and the trigeminal nerve of the subject, wherein the first substance comprises between 1 IU and 5 IU of oxytocin; and
   wherein the second step includes delivering a second substance to promote transfer of the first substance, wherein the second substance is a liquid and delivered after the first substance.

* * * * *

UNITED STATES PATENT AND TRADEMARK OFFICE
CERTIFICATE OF CORRECTION

PATENT NO. : 11,291,626 B2
APPLICATION NO. : 13/823071
DATED : April 5, 2022
INVENTOR(S) : Per Gisle Djupesland It is certified that error appears in the above-identified patent and that said Letters Patent is hereby corrected as shown below:

On the Title Page

Please add the following under the "Prior Publication Data" section:
--(30) Foreign Application Priority Data
September 14, 2010 (GB) ........ 1015371.6--.

Signed and Sealed this
Thirteenth Day of December, 2022

Katherine Kelly Vidal
*Director of the United States Patent and Trademark Office*